(12) United States Patent
Moreau

(10) Patent No.: US 10,324,095 B2
(45) Date of Patent: *Jun. 18, 2019

(54) METHODS FOR DIAGNOSING OSTEOARTHRITIS

(71) Applicant: VALORISATION HSJ, LIMITED PARTNERSHIP, Montreal (CA)

(72) Inventor: Alain Moreau, Montreal (CA)

(73) Assignee: VALORISATION HSJ, LIMITED PARTNERSHIP, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/158,689

(22) Filed: May 19, 2016

(65) Prior Publication Data

US 2016/0299155 A1 Oct. 13, 2016

Related U.S. Application Data

(63) Continuation of application No. 14/568,444, filed on Dec. 12, 2014, now abandoned, which is a continuation of application No. 12/447,152, filed as application No. PCT/CA2007/001901 on Oct. 25, 2007, now abandoned.

(60) Provisional application No. 60/854,077, filed on Oct. 25, 2006.

(51) Int. Cl.
| | |
|---|---|
| *C12N 5/10* | (2006.01) |
| *C07K 16/00* | (2006.01) |
| *A61K 39/395* | (2006.01) |
| *G01N 33/68* | (2006.01) |
| *C07K 14/47* | (2006.01) |
| *C12Q 1/6883* | (2018.01) |

(52) U.S. Cl.
CPC ..... *G01N 33/6893* (2013.01); *C07K 14/4703* (2013.01); *C12Q 1/6883* (2013.01); *C12Q 2600/136* (2013.01); *C12Q 2600/156* (2013.01); *C12Q 2600/158* (2013.01); *G01N 2333/47* (2013.01); *G01N 2333/4704* (2013.01); *G01N 2333/4706* (2013.01); *G01N 2800/105* (2013.01); *G01N 2800/50* (2013.01)

(58) Field of Classification Search
CPC ............ G01N 33/6893; C07K 14/4703; C12Q 1/6883

See application file for complete search history.

(56) References Cited

U.S. PATENT DOCUMENTS

| | | | |
|---|---|---|---|
| 5,401,635 A | 3/1995 | Nakamura et al. | |
| 5,463,026 A * | 10/1995 | Nakamura | C07K 14/4703 435/6.14 |
| 6,127,158 A | 10/2000 | Jentsch | |
| 2003/0154032 A1 | 8/2003 | Pittman et al. | |
| 2006/0094056 A1* | 5/2006 | Chappell | G01N 33/564 435/7.1 |
| 2010/0028882 A1 | 2/2010 | Moreau | |
| 2014/0329252 A1 | 11/2014 | Moreau | |
| 2015/0153362 A1 | 6/2015 | Moreau | |
| 2016/0223570 A1 | 8/2016 | Moreau | |

FOREIGN PATENT DOCUMENTS

| | | |
|---|---|---|
| WO | 2006089268 A2 | 8/2006 |
| WO | 2007044566 A2 | 4/2007 |
| WO | 2008049225 A1 | 5/2008 |
| WO | 2013053085 A1 | 4/2013 |

OTHER PUBLICATIONS

Fusaro et al., (JBC. Nov. 28, 2003;278(48):47853-61. Epub Sep. 18, 2003).*
ATCC Product Sheet for Ramos (RA 1 ATCC CRL-1596) (last accessed Sep. 14, 2017).*
Koike et al., (FEBS Letters 2005. 579:6733-6736; ePub Nov. 21, 2005).*
Nijtmans et al., (EMBO J. 2000. 19(11);2444-2451).*
National Cancer Institute (US National Institutes of Health) Cell Line Metadata Database (discover.nci.nih.gov/cellminer/metadata.do) Last Accessed Sep. 15, 2017). (pp. 1-4).*
Arden et al., (Best Pract Res Clin Rheumatol. Feb. 2006;20(1):3-25).*
Abecasis GR, Cookson WO., 2000. GOLD—graphical overview of linkage disequilibrium. Bioinformatics 16:182-3.
Altman,R. et al. Development of criteria for the classification and reporting of osteoarthritis. Classification of osteoarthritis of the knee. Diagnostic and Therapeutic Criteria Committee of the American Rheumatism Association. Arthritis Rheum. 29, 1039-1049 (1986).
Bacher S, Achatz G, Schmitz ML, Lamers MC. 2002. Prohibitin and prohibitone are contained in high-molecular weight complexes and interact with alpha-actinin and annexin A2. Biochimie; 84:1205-1218.

(Continued)

*Primary Examiner* — Michael D Pak
(74) *Attorney, Agent, or Firm* — Julie Gauvreau

(57) ABSTRACT

A method of predicting the risk of developing osteoarthritis (OA) comprising: (a) measuring the nuclear cellular level of prohibitin (PHB-1) in nucleated cells present in a blood sample from a subject having or suspected of having OA; and (b) comparing said nuclear cellular level to that corresponding to a control sample; and (c) identifying the subject as being at risk of developing OA when the nuclear cellular level of said PHB-1 in said blood sample is higher than in the control sample; and a composition for determining the risk of developing osteoarthritis (OA), said composition comprising: a cell sample from a subject; and a non-naturally occurring molecule for detecting nuclear accumulation of PHB1.

13 Claims, 22 Drawing Sheets

Specification includes a Sequence Listing.

(56) References Cited

OTHER PUBLICATIONS

Brasaemle DL et al. 2004. Proteomic Analysis of Proteins Associated with Lipid Droplets of Basal and Lipolytically Stimulated 3T3-L1 Adipocytes J Biol Chem; 279(45):46835-46842.
Bremner,R. et al. 1995. Direct transcriptional repression by pRB and its reversal by specific cyclins. Mol. Cell Biol. 15, 3256-3265.
Camper-Kirby D, Welch S, Walker A et al. Myocardial Akt activation and gender: increased nuclear activity in females versus males. Circ Res 2001; 88(10):1020-1027.
Campisi,J. 2001. Cellular senescence as a tumor-suppressor mechanism. Trends Cell Biol. 11, S27-S31.
Deeks,J.J. & Altman,D.G. 1999. Sensitivity and specificity and their confidence intervals cannot exceed 100%. BMJ 318, 193-194.
Dell'Orco,R.T., McClung,J.K., Jupe,E.R., & Liu,X.T. Prohibitin and the senescent phenotype. Exp. Gerontol. 31, 245-252 (1996).
Ding G. and Cantor C.R., 2004. Quantitative analysis of nucleic acids—the last few years of progress. J Biochem Biol 37, 1-10.
Doucet R, 2010. Rôle de la Prohibitine et de la sumoylation dans la pathogenèse de l'ostéoarthrose. Masters Thesis. Programme de biologie moléculaire, Faculté de médecine, Université de Montréal.
Drouin,J., Lamolet,B., Lamonerie,T., Lanctot,C., & Tremblay,J.J. 1998. The PTX family of homeodomain transcription factors during pituitary developments. Mol. Cell Endocrinol. 140, 31-36.
Drouin,J., Lanctôt,C., & Tremblay,J.J. 1998. La famille Ptx des facteurs de transcription à homéodomaine. Médecine/Sciences 14, 335-339.
Farré D, Roset R, Huerta M, Adsuara JE, Roselló L, Albà MM, Messeguer X. Identification of patterns in biological sequences at the ALGGEN server: PROMO and MALGEN. Nucleic Acids Res, 31, 13, 3651-3653, 2003.
Felson DT, Zhang Y. An update on the epidemiology of knee and hip osteoarthritis with a view to prevention. Arthritis Rheum 1998;41:1343-55.
Fusaro G, Dasgupta P, Rastogi S, Joshi B, Chellappan S. Prohibitin induces the transcriptional activity of p53 and is exported from the nucleus upon apoptotic signaling. J Biol Chem 2003; 278(48):47853-47861.
Gamble SC, Odontiadis M, Waxman J et al. Androgens target prohibitin to regulate proliferation of prostate cancer cells. Oncogene 2004; 23(17):2996-3004.
Gill G. 2005. Something about SUMO inhibits transcription Curr. Opin. Genet. Dev.; 15:536-541 (ABSTRACT).
Hamel, P.A., Gill, R.M., Phillips, R.A., & Gallie, B.L. 1992. Transcriptional repression of the E2-containing promoters EllaE, c-myc, and RB1 by the product of the RB1 gene. Mol. Cell Biol. 12, 3431-3438.
Hoh J., Jin S., Parrado T., Edington J., Levine A. J., Ott J. 2002. The p53MH algorithm and its application in detecting p53-responsive genes. PNAS Jun. 25, 99(13): 8467-8472.
Kasashima K, Ohta E, Kagawa Y, Endo H, 2006. Mitochondrial Functions and Estrogen Receptor-dependent Nuclear Translocation of Pleiotropic Human Prohibitin 2. The Journal of Biological Chemistry 281(47): 36401-36410.
Kolonin et al. 2006. Reversal of obesity by targeted ablation of adipose tissue. Nature Medicine 10(6): 625-632.
Kuramori C, Azuma M, Kume K, Kaneko Y, Inoue A, Yamaguchi Y, Kabe Y, Hosoya T, Kizaki M, Suematsu M, Handa H, 2009. Capsaicin binds to prohibitin 2 and displaces it from the mitochondria to the nucleus. Biochemical and Biophysical Research Communications 379:519-525.
Kurtev V, Margueron R, Kroboth K, Ogris E, Cavailles V, Seiser C. Transcriptional regulation by the repressor of estrogen receptor activity via recruitment of histone deacetylases. J Biol Chem 2004; 279(23):24834-24843.
Lam, E.W. & Watson, R.J. 1993. An E2F-binding site mediates cell-cycle regulated repression of mouse B-myb transcription. EMBO J 12, 2705-2713.
Lanctôt, C., Lamolet, B., & Drouin, J. 1997. The bicoid-related homeoprotein Ptx1 defines the most anterior domain of the embryo and differentiates posterior from anterior lateral mesoderm. Development 124, 2807-2817.
Lanctôt, C., Moreau, A., Chamberland, M., Tremblay, M.L., & Drouin, J. 1999. Hindlimb patterning and mandible development require the Ptx1 gene. Development 126, 1805-1810.
Lawrence RC, Hochberg MC, Kelsey JL, McDuffie FC, Medsger TA Jr, Felts WR, et al. Estimates of the prevalence of selected arthritic and musculoskeletal diseases in the United States. J Rheumatol 1989;16:427-41.
Lopez M.F., Pluskal M.G., 2003. Protein micro- and macroarrays: digitizing the proteome. J Chromatography B 787, 19-27.
Loughlin,J. 2001. Genetic epidemiology of primary osteoarthritis. Genetic epidemiology of primary osteoarthritis. Curr. Opin. Rheumatol. 13, 111-116.
Loughlin,J. Polymorphism in signal transduction is a major route through which osteoarthritis susceptibility is acting. Curr. Opin. Rheumatol. 17, 629-633 (2005).
Lyons P., 2003. Advances in spotted microarray ressources for expression profiling. Briefings in Functionnal Genomics and Proteomics 2, 21-30.
Mankin,H.J., Dorfman,H., Lippiello,L., & Zarins,A. Biochemical and metabolic abnormalities in articular cartilage from osteoarthritic human hips. II. Correlation of morphology with biochemical and metabolic data. J. Bone Joint Surg. Am. 53, 523-537 (1971).
Mankin H J, Dorfman H, Lippiello L & Zarins A. Biochemical and metabolic abnormalities in articular cartilage from osteo-arthritic human hips. II. Correlation of morphology with biochemical and metabolic data. I. Bone Joint Surg. Amer. vol. 53-A:523-37, 1971. "This Week's Citation Classic CC/No. 18, 1987.".
Marcil A, Dumontler E, Chamberland M, Camper SA, Drouin J, 2013. Pitx1 and Pitx2 are required for development of hindlimb buds. Development 130, 45-55.
Martin,J.A. & Buckwalter,J.A. The role of chondrocyte senescence in the pathogenesis of osteoarthritis and in limiting cartilage repair. J Bone Joint Surg Am 85-A Suppl 2, 106-110 (2003).
McClung,J.K., Jupe,E.R., Liu,X.T., & Dell'Orco,R.T. Prohibitin: potential role in senescence, development, and tumor suppression. Exp. Gerontol. 30, 99-124 (1995).
Messeguer, Ruth Escudero, Domènec Farré, Oscar Nuñez, Javier Martínez, M.Mar Albà. 2002. PROMO: detection of known transcription regulatory elements using species-tailored searches. Bioinformatics, 18(2): 333-334.
Mielenz D et al. 2005. Lipid Rafts Associate with Intracellular B Cell Receptors and Exhibit a B Cell Stage-Specific Protein Composition J Immunol; 174(6):3508-3517.
Miller, 1988. Chapter 30. Oligonucleotide Inhibitors of Gene Expression in Living Cells: New opportunities in Drug Design. Ann. Reports Med. Chem. 23:295.
Mishra S, Murphy LC, Nyomba BL, Murphy LJ. Prohibitin: a potential target for new therapeutics. Trends Mol Med 2005; 11(4):192-197.
Mishra S., Murphy L.C., The Prohibitins: emerging roles in diverse functions. J Cell Mol Med. 10(2): 353-63 (2006).
Montano MM, Ekena K, age-Mourroux R, Chang W, Martini P, Katzenellenbogen BS. An estrogen receptor-selective coregulator that potentiates the effectiveness of antiestrogens and represses the activity of estrogens. Proc Natl Acad Sci U S A 1999; 96(12):6947-6952.
Moreau, A., Yotov, W.V., Glorieux, F.H., & St Arnaud, R. Bone-specific expression of the alpha chain of the nascent polypeptide-associated complex, a coactivator potentiating c-Jun-mediated transcription. Mol. Cell Biol. 18, 1312-1321 (1998).
Morvan et al., 1986. a-DNA I. Synthesis, characteri7.ation by high field 1H-NMR, and base-pairing properties of the unnatural hexadeoxyribonucleotide a-[d(CpCpTpTpCpC)] with its complement /3-[d(GpGpApApGpG)] Nucleic Acids Res., 14(12):5019-5035.
Muller,H. et al. E2Fs regulate the expression of genes involved in differentiation, development, proliferation, and apoptosis. Genes Dev. 15, 267-285 (2001).
NCBI, PHB prohibitin [ *Homo sapiens* (human)] Gene ID: 5245, updated on Mar. 19, 2014.

(56) References Cited

OTHER PUBLICATIONS

Nijtmans LGJ, de Jong L, Artal Sanz M, Coates PJ, Berden JA, Willem Back J, Muijsers AO, van der Spek H, Grivell LA. Prohibitions act as a membrane-bound chaperone for the stabilization of mitochondrial proteinsEMBO J. Jun. 1, 2000; 19(11): 2444-2451.
Nijtmans LG, Anal SM, Grivell LA, Coates PJ. The mitochondrial PHB complex: roles in mitochondrial respiratory complex assembly, ageing and degenerative disease. Cell Mol Life Sci 2002; 59(1):143-155.
Ott, J. 2002. Predicting the range of linkage disequilibrium. Proc. Natl Acad. Sci. USA, 97, 2-3.
Peach,C.A., Carr,A.J., & Loughlin,J. Recent advances in the genetic investigation of osteoarthritis. Trends Mol. Med. 11, 186-191 (2005).
Rajalingam K, Wunder C, Brinkmann V et al. Prohibitin is required for Ras-induced Raf-MEK-ERK activation and epithelial cell migration. Nat Cell Biol 2005; 7(8):837-843.
Rasmussen RK, Ji H, Eddes JS et al. Two-dimensional electrophoretic analysis of mixed lineage kinase 2 N-terminal domain binding proteins. Electrophoresis 1998; 19(5):809-817.
Rastogi S, Joshi B, Dasgupta P, Morris M, Wright K, Chellappan S. Prohibitin facilitates cellular senescence by recruiting specific corepressors to inhibit E2F target genes. Mol Cell Biol 2006b; 26(11):4161-4171.
Rastogi S, Joshi B, Fusaro G, Chellappan S. Camptothecin induces nuclear export of prohibitin preferentially in transformed cells through a CRM-1-dependent mechanism. J Biol Chem 2006a; 281(5):2951-2959.
Reginato,A.M. & Olsen,B.R. The role of structural genes in the pathogenesis of osteoarthritic disorders. Arthritis Res. 4, 337-345 (2002).
Reich NC, STAT Dynamics. Cytokine Growth Factor Rev. 2007; 18(5-6): 511-518.
Roy-Beaudry,M. et al. Endothelin 1 promotes osteoarthritic cartilage degradation via matrix metalloprotease 1 and matrix metalloprotease 13 induction. Arthritis Rheum. 48, 2855-2864 (2003).
Scheel J., Von Brevern M.C., Horlein A., Fisher A., Schneider A., Bach A. 2002. Yellow pages to the transcriptome. Pharmacogenomics 3, 791-807.
Spector,T.D. & MacGregor,A.J. Risk factors for osteoarthritis: genetics. Osteoarthritis. Cartilage. 12 Suppl A, S39-S44 (2004).
Sun L, Liu L, Yang XJ, Wu Z. Akt binds prohibitin 2 and relieves its repression of MyoD and muscle differentiation. J Cell Sci 2004; 117(Pt 14):3021-3029.
Takahashi,Y., Rayman,J.B., & Dynlacht,B.D. Analysis of promoter binding by the E2F and pRB families in vivo: distinct E2F proteins mediate activation and repression. Genes Dev. 14, 804-816 (2000).
Tommasi,S. & Pfeifer,G.P. Constitutive protection of E2F recognition sequences in the human thymidine kinase promoter during cell cycle progression. J. Biol. Chem. 272, 30483-30490 (1997).
Trotman LC, et al. Ubiquitination regulates PTEN nuclear import and tumor suppression. Cell. 2007; 128(1): 141-156.
Wang S, Nath N, Adlam M, Chellappan S. Prohibitin, a potential tumor suppressor, interacts with RB and regulates E2F function. Oncogene 1999; 18(23):3501-3510.
Wang S, Nath N, Fusaro G, Chellappan S. Rb and prohibitin target distinct regions of E2F1 for repression and respond to different upstream signals. Mol Cell Biol 1999; 19(11):7447-7460.
Wang S, Fusaro G, Padmanabhan J, Chellappan SP. Prohibitin co-localizes with Rb in the nucleus and recruits N-CoR and HDAC1 for transcriptional repression. Oncogene 2002; 21(55):8388-8396.
Wang S, Zhang B, Faller DV. Prohibitin requires Brg-1 and Brm for the repression of E2F and cell growth. EMBO J 2002; 21(12):3019-3028.
Wang S, Zhang B, Faller DV. BRG1/BRM and prohibitin are required for growth suppression by estrogen antagonists. EMBO J 2004; 23(11):2293-2303.
Wood, W.I. et al. 1985. Base composition-independent hybridization in tetramethylammonium chloride: A method for bligonucleotide screening of highly complex gene library. Proc. Natl. Acad. Sci. USA 82. 1585-1588.
Xue Y, Zhou F, Fu C, Xu Y, Yao X. SUMOsp: a web server for sumoylation site prediction. Nucl Acids Res 34: W254-W257, 2006.
Zheng,N., Fraenkel,E., Pabo,C.O., & Pavletich,N.P. Structural basis of DNA recognition by the heterodimeric cell 140cycle transcription factor E2F-DP. Genes Dev. 13, 666-674 (1999).
Australian Examinaton report in AU2007308315 dated Sep. 24, 2010.
Australian Notice of Acceptance in AU2007308315 dated Jun. 9, 2011.
CIPO Notice of Allowance in CA2703124 dated Oct. 25, 2016.
CIPO Office Action in CA2703124 dated Mar. 4, 2014.
CIPO Office Action in CA2703124 dated Jan. 28, 2015.
CIPO Office Action in CA2703124 dated Jan. 5, 2016.
EPO European Extended Search Report in EP07816051 dated Jan. 29, 2010.
EPO Notice of Allowance in EP07816051 dated Mar. 24, 2011.
EPO Office Action in EP07816051 dated Apr. 6, 2010.
EPO Office Action in EP07816051 dated Nov. 22, 2011.
PCT International Preliminary Report on Patentability in PCT2007001901 dated May 7, 2009.
PCT International Search Report in PCT2007001901 dated Feb. 15, 2008.
PCT International Preliminary Report on Patentability in PCT2012050723 dated Apr. 24, 2014.
PCT International Search Report in PCT2012050723 dated Jan. 17, 2013.
U.S. Non Final Rejection in U.S. Appl. No. 12/447,152 dated May 13, 2011.
U.S. Non Final Rejection in U.S. Appl. No. 12/447,152 dated Jan. 12, 2012.
U.S. Non Final Rejection in U.S. Appl. No. 12/447,152 dated Mar. 27, 2014.
U.S. Non Final Rejection in U.S. Appl. No. 12/447,152 dated Aug. 14, 2014.
U.S. Non Final Rejection in U.S. Appl. No. 14/351,398 dated Sep. 15, 2015.
U.S. Non Final Rejection in U.S. Appl. No. 14/568,444 dated May 13, 2016.
U.S. Restriction Requirement in U.S. Appl. No. 12/447,152 dated Jun. 11, 2010.
U.S. Restriction Requirement in U.S. Appl. No. 14/351,398 dated Mar. 30, 2015.
Devauchelle V, Marion S, Cagnard N, Mistou S, Falgarone G, Breban M, Letourneur F, Pitaval A, Alibert O, Lucchesi C, Anract P, Hamadouche M, Ayral X, Dougados M, Gidrol X, Fournier C, Chiocchia G. DNA microarray allows molecular profiling of rheumatoid arthritis and identification of pathophysiological targets. Genes and Immunity (2004) 5, 597-608.
Gearhart MD, Corcoran CM, Wamstad JA, Bardwe VJ. Polycomb Group and SCF Ubiquitin Ligases Are Found in a Novel BCOR Complex That Is Recruited to BCL6 Targets. Molecular and Cellular Biology, 2006, 26(18): 6880-6889.
Weldingh K, Rosenkrands I, Jacobsen S, Rasmussen Pb, Elhay Mj, Andersen P. Two-Dimensional Electrophoresis for Analysis of Mycobacterium tuberculosis Culture Filtrate and Purification and Characterization of Six Novel Proteins. Infection and Immunity, 1998, 66(8): 3492-3500.
Burdall S.E et al. Breast cancer cell lines: friend or foe? 2003 Breast Cancer Res, 5:89-95.
Aigner et al. Aging theories of primary osteoarthritis: from epidemiology to molecular biology. 2004 Rejuvenation Res., 7(2):134-45.
Guide to labeling your primary antibody, 2010, Innova Biosciences (www.innovabiosciences.com).
Ronen et al. Expression of a novel marker, Ubc9, in squamous cell carcinoma of the head and neck. 2009 Head Neck, 31(7):845-55. doi: 10.1002/hed.21048.
Body mass index, 2018, Wikipedia. (https://en.wikipedia.org/wiki/Body_mass_index).
USPTO Final Rejection in U.S. Appl. No. 15/041,701 dated Jul. 26, 2018.
Haringman et al. Chemokine and chemokine receptor expression in paired peripheral blood mononuclear cells and synovial tissue of

(56) References Cited

OTHER PUBLICATIONS patients with rheumatoid arthritis, osteoarthritis, an reactive arthritis. 2006 Ann. Rheum. Dis., 65:294-300.
Tatham et al. Role of an N-Terminal Site of Ubc9 in SUMO-1, -2, and -3 Binding and Conjugation. 2003 Biochemistry, 42:9959-9969.
Western blot, 2018, https://en.wikipedia.org/wiki/Western blot.
U.S. Non Final Rejection in U.S. Appl. No. 15/041,701, dated Jan. 11, 2018.

* cited by examiner

Pitx1 +/+

Pitx1 +/-

|  |  | E2F core |  | CHR |  |  |
|---|---|---|---|---|---|---|
| DNA Polα | -126 | CGTT | TGGCGCCC---- | T | GTGAT | -143 | Act |
| p107 | -18 | ATTT | CGCGCGC---- | T | TTGGC | -1 | Rep |
| Cdc2 | -27 | TTTA | GCGCGGT-- | GAGT | TTGAA | -8 | Rep |
| Adeno E2a | -69 | GTTT | CGCGCT- | TAAAT | TTGAG | -49 | Act |
| E2F-1 | -16 | GATT | GGCGCG- | TAAAA | GTGGC | +5 | Rep |
| H2A | -51 | TTTT | CGCGCCAA- | TA | GTGTT | -31 | Act |
| DHFR | -2 | AATT | CGCGCC-- | AAAC | TTGGG | +18 | Act |
| HsOrc1 | +4 | AACT | CGCGCC---- | AA | TCGGC | -14 | Rep |
| c-Myc | -56 | TTTT | CCCGCCAAGCCT | CTGAG | -77 | Act |
| CycA | -41 | ATAG | TCGCGG-- | GATAC | TTGAA | -22 | Rep |
| Cdc25 | -21 | GGGC | TGGCGGA-- | AGGT | TTGAA | -2 | Rep |
| TK | -87 | GACC | TGGCGGG-- | AGAT | TTGGC | -106 | Act |
| B-Myb | -51 | CACT | TGGCGGG-- | AGATA | GGAA | -32 | Rep |
| hPitx1 | -3734 | TCAC | TGGCGGC-- | AGTC | CTGCT | -3715 | Act/Rep |

FIG. 3

FIG. 4A WT probe
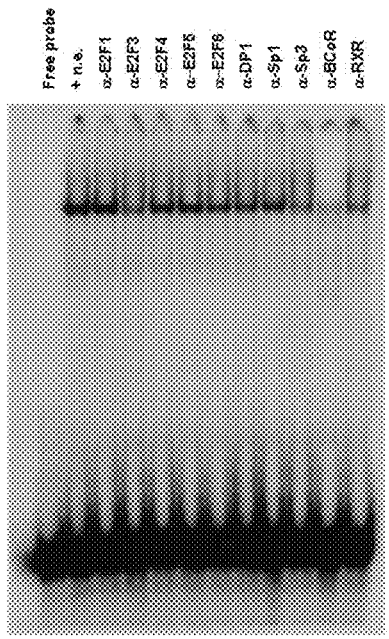
FIG. 4B mutant probe
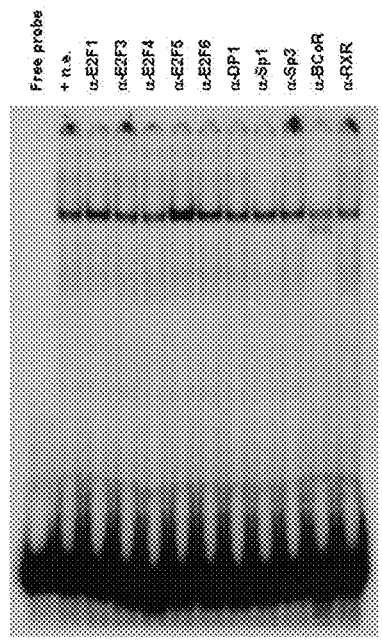
FIG. 4C
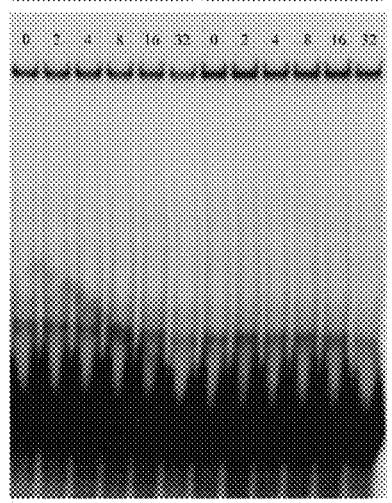
FIG. 4D
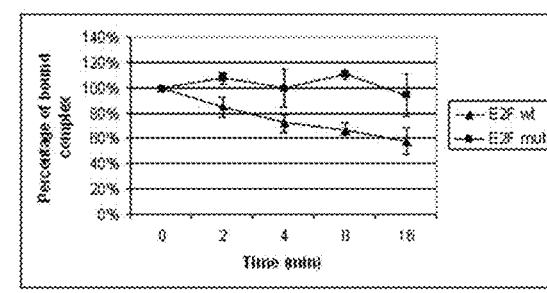

FIG. 6A  Normal cartilage
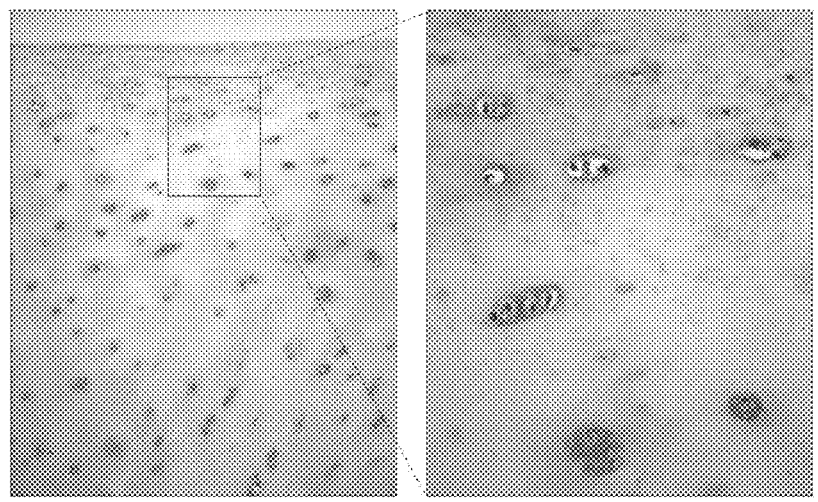
FIG. 6B  OA cartilage
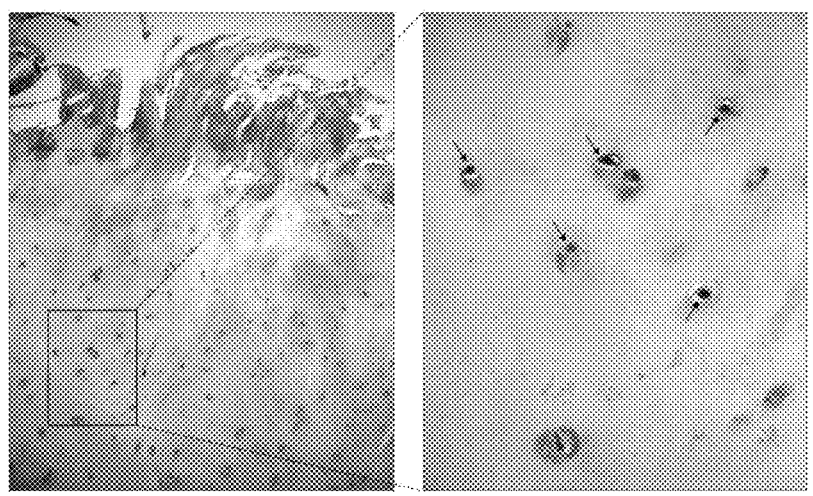
FIG. 6C
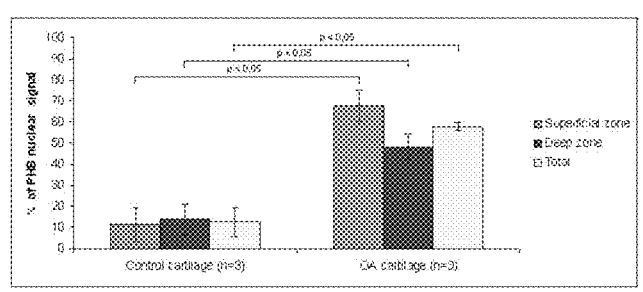

Table S2. Identification of peptides corresponding to nuclear factors interacting with the mutant E2F site found in human Pitx1 promoter in OA articular chondrocytes.

| Group (#) | Spectra (#) | Distinct Peptides (#) | Distinct Summed MS/MS Search Score | % AA Coverage | Mean Peptide Spectral Intensity | Species | Database Accession # | Protein Name |
|---|---|---|---|---|---|---|---|---|
| 1 | 1 | 1 | 9.35 | 2 | 1.41e+009 | Homo sapiens | 26149302 | BCL-6 interacting corepressor isoform 2 |
| 1 | 1 | 1 | 9.35 | 1 | 1.41e+009 | Homo sapiens | 21071037 | BCL-6 interacting corepressor isoform 1 |
| 1 | 1 | 1 | 9.35 | 1 | 1.41e+009 | HUMAN | 57012586 | BCoR protein (BCL-6 corepressor) |

| # | Filename | z | Score | MH+ Matched (Da) | Spectrum Intensity | Sequence |
|---|---|---|---|---|---|---|
| 1 | 1_GelShift.0273.0437.3 | 3 | 9.35 | 2781.563 | 1.41e+009 | (R)VPSAKAVTSGLPGDTALLLPPSPRPSPR(V) |

| Group (#) | Spectra (#) | Distinct Peptides (#) | Distinct Summed MS/MS Search Score | % AA Coverage | Mean Peptide Spectral Intensity | Species | Database Accession # | Protein Name |
|---|---|---|---|---|---|---|---|---|
| 1 | 5 | 5 | 65.87 | 21 | 3.73e+006 | Homo sapiens | 46360168 | prohibitin |
| 1 | 5 | 5 | 65.87 | 21 | 3.73e+006 | Homo sapiens | 48458373 | PHB |

| # | Filename | z | Score | MH+ Matched (Da) | Spectrum Intensity | Sequence |
|---|---|---|---|---|---|---|
| 1 | 180306000010.0625.0635.2 | 2 | 16.01 | 1149.590 | 4.59e+006 | (R)FDAGELITQR(E) |
| 2 | 180306000010.0990.0993.2 | 2 | 14.96 | 1855.033 | 5.36e+006 | (R)NITYLPAGQSVLLQLPQ(-) |
| 3 | 180306000010.0813.0817.0 | 2 | 13.49 | 1185.659 | 3.12e+006 | (K)DLQNIVNTLR(I) |
| 4 | 180306000010.0925.0929.0 | 3 | 13.44 | 2098.166 | 4.00e+006 | (R)SRNITYLPAGQSVLLQLPQ(-) |
| 5 | 180306000010.1023.1023.0 | 2 | 8.00 | 1998.087 | 9.55e+005 | (K)AAELIANSLATAGDGLIELR(K) |

| Group (#) | Spectra (#) | Distinct Peptides (#) | Distinct Summed MS/MS Search Score | % AA Coverage | Mean Peptide Spectral Intensity | Species | Database Accession # | Protein Name |
|---|---|---|---|---|---|---|---|---|
| 1 | 5 | 5 | 42.96 | 26 | 1.76e+006 | Homo sapiens | 1673514 | B-cell receptor-associated protein |

| # | Filename | z | Score | MH+ Matched (Da) | Spectrum Intensity | Sequence |
|---|---|---|---|---|---|---|
| 1 | 180306000012.0390.0404.0 | 3 | 9.23 | 1502.856 | 1.34e+005 | (R)AAQNISKTIATSQNR(I) |
| 2 | 180306000012.0382.0325.2 | 2 | 9.15 | 1471.776 | 4.74e+005 | (R)QKIVQAEGEAEAAK(M) |
| 3 | 180306000012.0498.0504.0 | 2 | 8.99 | 994.485 | 5.02e+006 | (R)LGLDYEER(V) |
| 4 | 180306000012.0621.0626.0 | 2 | 8.16 | 899.569 | 2.24e+006 | (R)AQVSLLIR(R) |
| 5 | 180306000012.0890.0890.0 | 2 | 7.46 | 1210.741 | 9.03e+005 | (R)VLPSIVNEVLK(S) |

FIG. 7

FIG. 11A
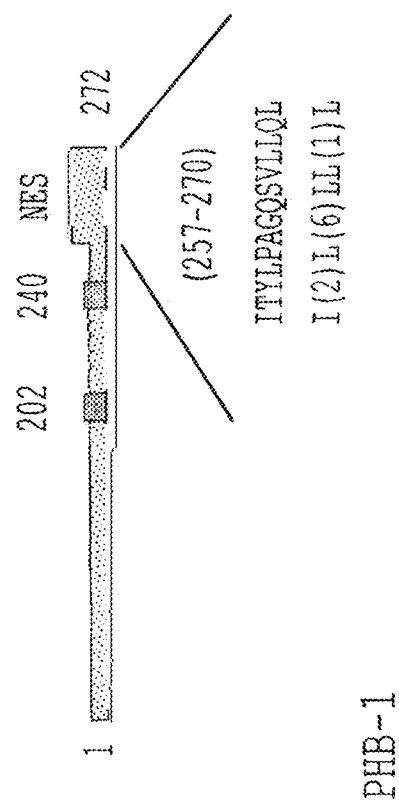
FIG. 11B
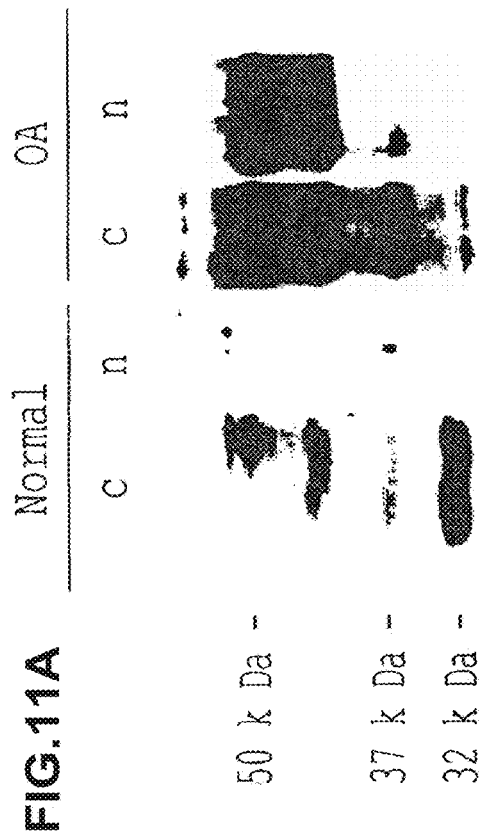
FIG. 11C
| Position | Flanking peptide | GPS Score | Cut-off | Matching Motifx? |
|---|---|---|---|---|
| 202 | RARFVVEKAEQQKKA | 4.00 | 18 | Matched |
| 240 | DGLIEIRKMLEAAEDI | 1.52 | 18 | Matched |

```
530        CCCAAATTGTCTATCTGTG▓▓▓▓▓▓▓▓▓▓▓▓▓▓▓▓▓GGGCCCTGAGCACCCTGTGTCCTGTGCA
           -10006
GCAGTCAGATATCTGGAGGGAGACTGAGGCACTGGCTGCAGAGCTTGTGATCATGAGAGAGACTCACTAGG
-9940
ACTACAGATGGGTAAACTGAGGCCTTCGAGGGGGCAGCTCCAGAAAGGCAGGGGCCATAATGTCTCACCTT
-9869
CATATTTCCCGTGCCAAGCTGTGGCCTTCTGCATTCATGGCAGATGAGTGGACAAAGGCTGATGGACTGAT
-9798
GGAGAAACAAAGGGATAGATGGAGCAGCTGGGCAGCTCAGCAAATGATGCTGCAATGATCTGCTTCCAACT
-9727
CACCTCAAATCCATCCTTCTCTCTCCAGGCAGAGTGGGCTTTTAAGATACACATCTGGCCAGGTCTCTCAC
-9656
TGTTCAAACCCTTCATCTGCTCCTTTTTGCCTTCAGGATAACATCCCACCCTCCTATCAAGGACTATGGAG
-9585                          (-9543)G
CCCTGTGGGATCTGGTTCCCACTTGATTCTCCAACTTCCTCTTCCCTATGCCCTGCCTTCTCATCTGTTC
-9514
CAGTGCTATTATGAAGCCACACGTTCTTCCTTTATTATCAAGCATACCACAGTTTATCTCACCTCAGAGGC
-9443
TTTGCACAGTATATTTTCCTAGGGAGGGGTCCCCAGGTGGTAGAAAAACGGTTACAGCCAACTCCTCCATG
-9372                                      (-9323)T
TCTCACTCAAGACCCTTCAACAGCAGGCTCCAGATTTCCTCTCCA▓▓▓▓▓▓▓▓▓▓▓▓▓▓▓▓▓▓▓▓▓AATGGA
-9301
TTTCTGTGTCTGCCTCCTTGACTCAACCCAAATGAACAAGAGCCATCTATCTCTGTATCTCTGCAATCACA
-9230
GGCACAAAATAGGTGCTCTCTACATTTTTTCCAACCTGAGAGGCCATTCTAGAAGGGT▓▓▓▓▓▓▓▓▓▓▓▓
-9159
▓▓▓▓▓CCAGTATTCCATGCAGATGCTGACAGGACTGCAATTAAAAAAATACTTGAGATGCCCAAATGCCCA
-9088
AATAGCTTCTCATTTTGCTTTGACTACCAATAATTGCACAGTGCAATAGAATAATGCTCAAATACATTAAC
-9017                                    (-8969)C
ATCTTACTTGATCCTAGGGGGTCCTCTCTACTTTTAAAGCCTCAAACTTCCTCCCTCTCACAGGTGAAAAG
-8946
GGGAGTACAAATACATTCCCTCCCTTGCTCTGCGGATCCATTCCTACAGGTAGTCAAGACTCTGAGCTTCC
-8875
CCTCTGACTTTCTGGCAGTGCTTCACCTCTCCCCACAGATGAGTGCAGGAACAATTCTAACAGACTTCAGA
-8804
CTCTTCCAACAGAGCCAATCCCTCCCCATCACGTTGGAGTGGACTTGCTACCCACACCATCAACAGGCCCC
-8733
TGAGAAACTTCACAGGGCAGGGGCTTCTTTGGTAAAACCAACCCTTTCCTTCCACCAGCTCAGAGAAGTTG
-8662
TTCCAGATAGATGCCAGGATTCTTGGAGGAGCATGGTGATTCTGGGGTGGAGCCTCTGACCCTGGCCAACC
-8591
AAAGGCCTGAGCCACTCTTCCCCCACAAAGTGATTGGCGCAGGAGTGGGCATGTAAGCTGGACCCAGCCAA
-8520
TCAGCATAACCAAATCCCTTGCCCACCCTGGGGAGGGTCCTATAGTTGTTGCCAAGAGAGGCTCACCCCTG
-8449
TTCTCAAGAAGCTT▓▓▓▓▓▓▓▓▓▓▓▓▓▓▓▓▓GTTTTAATCTATCATTACACAAATATTTAATTTCAAT
-8378
ACTGTTGCAATAAGAGCTATG▓▓▓▓▓▓▓▓▓▓▓▓▓▓▓▓▓▓▓▓TACTTTTACTTGGTGTTAAGATTTGAAGAA
-8307
GAAAAAAAAAAAACACTGCCTGAAGGATTGTTATGGCCTTCTATATAATAGTGGCTGCAGACATTTGCCCA
-8236
TTATGTTCAGCATGAACCCATGTGACAAATTCATCAAAGCGTTTTGCACTAGGGAGAAAAATTTGTATTAG
-8165

AGGAAGCACAGCAGTTTGGACTGAAAGACAAAGAAATTCAGCCAATTCTGCTGATCTTTTTTGATGGGGC
-8094
ACCTGGAAGCTGAAAGCTAAAGTGGTACTCAGGAACAGGGACTGCTACTTCTGTTCCTGGTGAATCCTGCC
-8023
CCAAAGCTCCTCTCTCTCTGATTCCTGATTCCACTGTGCCAGTGGGAATATATGCTCCCAAGATGTCAAA
-7952
ACTAAAGGGAAATTGCAAAAAATATATACATATATTTTTAGAGAGAAAATAAGATTATAAAAAATGTGTTT
-7881                    (-7842)+ACTG   +ACTG(-7839)
```

FIG. 15A

```
TGTACCCCCCAAGTTTCACTAAGAACTTCCTGACTTCCAGGCCCTGGTTGTGCCCCACGCACCAGCCTGCC
-7810              (-7784)C
CAGCTTTCCTGGACCAAACTTCCTAGCACCTAAGCAGGGGATGAGGGCAGATAAACTAAATCAGAAAAGGG
-7739
ATCTGTTCCTCCTAGACTCAACCAACATGACCACCGTGGGGAAGAAGAAACAAAAACAAGAGCAAACTCT
-7668
CTTAAAGAGCAGCCTGGCAGCTATCACCA▨▨▨▨▨▨▨▨▨▨▨▨▨▨▨▨CCACAGGACTCAGGACCAAACC
-7597
CCTCACCTTCACTATCCCATCCGTTTCCCAAGAAGCAGAAATACTTATTCTCACATTTCACAGATGGGGAA
-7526      (-7509)T
GCTGAGGCTAGGAGAGGTTATG▨▨▨▨▨▨▨▨▨▨▨▨▨▨▨▨ACTAGTAAAAGCCACTGACAAGATTCTGG
-7455
CTCAGGCCATCAGGTGCCAGAGGCAGCATTTTTTGGCACCACAGGCCCTGCCTGGGAACAAGAGCATGCAG
-7384
AAAATCTCACAAGAGATGGGAACAAAATTTGGAAAATTGCTAGCGTGCAGGGAGGGGGAAGGTGTGATTT
-7313
CCTGCTACAGACGCCAGAGTAAAAGCCACCCCAGGAGTGCCTGTGCAGCCCTCCATAGTAAGGTCCAGCGG
-7242
CTGCATTTATGCCCAAAGATGCCCCTGGTGCTTGGAGTGGAAGGAAGATTCCAGAGACAAGATTAGAAACT
-7171
TCTCAGCTTAGCAGCTCTAGGGCTGGACCCGCCAACAAGCCATTTTACACATAAAGCAGTCAATGGGAGGG
-7100
GGTAGACGTAGGGGGCTAAACTCCCCACAGCACAGGGTCCAAGTTGGTAGACTGCACTTTCTCCAGGCGCA
-7029
GGTCCGCTAGTGCCGGCATCGGGGACTCGTTATCTTAACTTGCGACCCTGGGTGCACAGAGCCCTGCACAC
-6958
ACCACTGGAGAGGGGTTCCTGCTGTCGAGGGTTGAGAGGAGGGTATGGAGTCCCTGGAACAGCACGACAGG
-6887
GTGCAGAGGCCACCTGGCAGGGCCTGAACACCGAGGCCTCTGTGAGCTTGGTCGGGCCGGCTTCCCGCTT
-6816
CGGAGGTTGGGGAGGGGGTCGTGGGTCTCTGCGTTCCCAGGCCAAGCGGCCCTGG▨▨▨▨▨▨▨▨▨▨▨
-6745
▨GCCGAGGTGCGCGGGTCGCGGCCTCTCCCGCAGCAGCTGTCGGCGAGAACCAGGCAGGAGGCGCCG
-6674
▨▨▨▨▨▨▨▨▨▨▨▨AGATTCAGGCCCGGCTGCCGCGCTGCCATCTCCCGGCACCTTGCGCCGGA
-6603
AACGGTCGCTCTGGAGCCCGTGGCCGTCGGCGGGCAGGCTTAGCCGCTCCAGTCCCTGAGAAAGGCAGGCC
-6532
ACAGCCCGACCTGCCCTGTGGTCCCATCCCATAATCCCAACAGCAAGCAGGCTCAGGCTGGGCACTTCGGG
-6461
GTACCAGGAGTAGGTTCGGCCAACTGGTTTCCACCATGAGGCTTCGCGCACAGGGTTATCTGGCCACGAGG
-6390                            (-6345)C              (-6322)G
CAACGCTGGGGAGCCCTGTGGCCTGAGGGTGGGCAAAGGACAGGCTCCCAGTTCCCTTGCGTCCAGCCCGT
-6319
CTCCCAGCGGCAGCCAGCCAGGAACGGCCTGCGGGGCCACAGGGGTGGAGGCGTCACCGTTCGCAGGCCCG
-6248
CAGCAGGATGGTCGCTGGGGGATGTGCAGGCATAGGGGTTGGACAAGGGGCCCCAGAAGTGTCTGTCCTGA
-6177
GGGGTTGGTGTGCCCTTTCCTCACCAGCCCAGCCCCTGAGGAGAGGGAAGAAGGCAATTCCCCCAACCAGG
-6106
GCAGGTCGGGCGGTTGCCCCACCCTAACACCCCCTACCCCCAAACACAGAAAACCTGGGGTCTGTCCTCAA
-6035
ACCTCCCTGGCTGCCACGCTCTGGGCAGCGGACTCTCCCTGCCAACACGCAAGACCAGCTCCCTCCCGCAG
-5964
GCTGAGCAGAAAGAAGAAAGGTCCAATCTCAAAACCCCAAACTCGACCACCAGCCCCCGTCTAAACGGAAG
-5893
TAGGGCCAGCCCCT▨▨▨▨▨▨▨▨▨▨▨GGGCCCAGGGAGAGAAAGTGCCCCAGGGCCAGGCTGG
-5822
GACCCG▨▨▨▨▨▨▨▨GCGGCAGGGCCCCTCCACGGAGGTCCAGGGCGCGCTCCCCGGCCTC
-5751
GAGGCCCGGCCGCCAGCCGCGCGGACCCCAGCCTACGCCCCGAGGGAGGCCAGGACCCCTAGCCGGCGGGA
-5680
CTGCGCGCCGCCCCTCTCCCCGCAGGTCCCGGCGAACACCTAGCTTCCCCTCCCCCACCCTTCCCGCCTC
-5609      (-5591)A
```

FIG. 15B

```
CCGGCCAGTGTCCCCGCCTTCCCCGCGGGGCGACGGGCGGCGGCGGCGGGAGGAGCGGGCCGAGCCGAGGAA
-5538
GCCCCGGCCTCGCGCGCTGGGATGTAGCGAACCAGCAGGGGCCGAAGAACCGTGCAGTGCCAGAGCCAGAG
-5467
CTGGATCCGGGGCCCCAGCCGGAGCCGAAACCTGAGCCAGAGTCCGCGGCGGGCGAGCCCGGAGCCCACGA
-5396                                                                (-5330)G
GCCGCAGACGCAGCGCTGCCCAGGTGGGGTAAGAGACGCTGGGCTAGGGGCGCAGGGTCTCCGCGGTGGAG
-5325
GGGCGCAGGGAGGTGGCGGCCGAGTCCTGCGCAGTTTGCTCCTGGCGTGTGTGGGTCCACCCGGCGGCCG
-5254                                                                (-5185)+G
GGACAGCGCAAGGCGCGGAAGGTCAGGAGCCTTCGAGGCAGCGCGAGGAGCTCGTTCCTGCGCCCAGGGCA
-5183
CAGTCATAGCCGCCGTCACCGGGTGCTACCTCACCCAACCGGCGGGATCAACCCTCTGCTTTGGCTCCGGG
-5112
CACCCTCAAGAGGGTAGCAGCCTCGGGGGCACGGGCCACGGCCCCGCGAAGGGCACAACCTGAGAAGCCCGT
-5041
GGCAGCCCCTCGCAGCGTCGGGTGACACAGGGCTCCCCCACCCCAGGAGAAGTGGGCAGGAGAGAGGGCC
-4970
GCCCGCTGCTCCCCGCTGCGTCCAGGGATGGAGGGCCCCACCACCCATGGAATTGCTGGCCCCTCTGCGTG
-4899      T(-4889)
GCCCGGGACTTCAGCCGTGGCT▓▓▓▓▓▓▓▓▓▓▓TCCTAAACGAAACCGCTTCGTTCGTTCGT
-4828
TCGTTCGTTCGTTCGGGCAGCAATGCC▓▓▓▓▓▓▓▓GGTCCGCGCCCTGGCTCTCTTCGC
-4757                       (-4719)A                    (-4692)T
CCCGGACCCCGACGTCCCGCCGCAGCGCTCGGAGGTGCCCCCAGCCCAAGGCAGCCTGCTCTCGCCGGCAC
-4686                                                  (-4626)G
AGGTCGGGCTTTTTCTTCCCAGGAGAGAAACCCCAATTCCCTTCGTAACGTCCAATAAAGACATTCCCGCG
-4615
GCTTCTCCCAGGTTTGGTTGTTGACGCAGGGTCCGGAGCACGCAGTCGCTTCTCAAGAACCGGGTCTCGG
-4544
ATTTCTGAAATTGACCAGCTTCGTAAATTGGAGCCTATTCTCCCGCGGCAAAGGCAGGGCCCCAAAGCCGG
-4473
GATCGCAGTAATGGGAACCCCAGGCTGGAATCCGGGTCCCAAGCTTTTCCGATTTAGGAATTCCCCGAATC
-4402
TACAAATATTTAGTCCACTTTTCTGAAAAACTAAATTCTGAAAAACACAAATTCTCTTGACATCCCTGTGA
-4331      T(-4329)
CCTCTGAAAGCCACCAGGGCCAGAGGGAGGAAATCCCAGGTTGCTGTCCACTGGGGGAGGATTCAGGTCTA
-4260          (-4238)C              (-4211)G
GGGTTCAGGTCTACGGTAGTCAGGGCAAAAGCTACAGGCAGCAGGGCAGCACAGGAGACTTGCTGTCCCC
-4189                                                              (-4120)G
GTGCCCTTTCCCGGGGCTGCTTTCGGCCTCCCGCATCTCTTCCAGGGAAAGGAAAAGAGGTGGGCTGGGGC
-4118
TTGGAGACCAGGCTGTCTGGACTCTAGGATGCAGAGGCCTCCAGACAGGCTCAGGGTGCTCTTCTCCCATG
-4047   G(-4039)
AAAGCAGCCGCTGGGAGGAGGAGGCTATGGTGCATCCATAAGTTGCCCCTCTGCTCCCCAGTTGTGCGACC
-3976      A(-3966)
AGCTGCTACCTCCTTCCTAGTCTTCTTCCCCACA▓▓▓▓▓▓▓▓▓▓CAGACAGCGTCCATGGA
-3905
CTTAGGTGAGAGATGGGCC▓▓▓▓▓▓▓CCAGCCGCTGACTGAGCGGCCCACGGCACAGA
-3834
GTCCTGAGTTCCATACTCCCATCTGTGCCTCACTGGCGGCAGTCCTGCTCAAATACATCCTGGCTCTCCCC
-3763                           (-3727)T
GGGACAGGCTGGGGATCCCCATTTGGCAGGAAGCCTCAGACTGGGGTCCCAGGAAGCCTAAAGGAGCCAGT
-3692
GAGGTCTTTCCAGCCCCTACCTGAGCACCCTCCTCCCCACTTACCCAGTAATTGCTGTATTCAAAGAAACG
-3621
GGAGCTTTTATTGGGGAGGGGGTGTTAGATCAGGCAGAAAGAGGTAGGTGGTCCAAACCTGCACTCCCAAA
-3550
ACAGGGTTTTCAAGTTTGAACTTCTCCACGGACTAAGAGGCTTAGGGCTGGAATGTCCCAGAGAGTCATGG
-3479                                                        (-3415)ACT
ATAGCCCTGGTGGCAGGCCATGGCACATTCCTTCCTTTTTCCTAAAATACCTTGATTCTGGGAGCAAGGAT
-3408
```

FIG. 15C

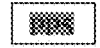

TAGGGCACGGTGCCCCCGTGGGTGGGTAGAAGGATGCCCCCCACTGAGAGCCTTCCAACCACCCTTCCCA
-3337
AATTACATTACTAAACCATTCTTGGGCACAGGGTGTTTTTAGTGAGCCAGGCTTCAGGAAGGGTCCTCATG
-3266
GTGACTACTTCAACCCCACAACAGCCCAAGCTCTTCTGCTCAGCCCAGCCAAGACCCTAAACTCCAAAATT
-3195
CTTGAAAATCAGAGAATCATTGCTGGCTTTGTGTGGTCACGGAGGGGTGGGGAACAGGGCACATGGTTCCA
-3124
GCTCCACTAAGCCCCCTTCCCTCCTCTCTTCGTGTCCCATCAG▓▓▓▓▓▓▓▓▓▓▓▓▓▓▓▓▓▓▓▓▓GCAGCAGG
-3053
CAGAGTCCGGTGTTGGACATGGGAACTGAGGCACAGTGCAGATCAAGCCTTAACCTTGAGGGAAACACAGG
-2982
TCACATAGCACAGCTGGGGGAACACAAAGCCTCTGCTTACTCCTGAAAGAGTGCTGTTTTCTGTCCTGTAT
-2911
GTGTGACGTGTCTGTGAGCGTGCAAGAAGCCCCT▓▓▓▓▓▓▓▓▓▓▓▓▓▓▓▓▓▓▓CAGTGAGTGTAGCTGGG
-2840   T(-2833)
GAAGAATTGAGAGCATGTCCAGGTCCCTTCCCCAGCCAACGCCCAAGATCAGGCCACAGCCTCCTCACAAT
-2769
CAATTGCCTCCTCACTCCTTGATCACTCAGTGCTGCCCAGGCCAGCAGAACAGACTCTGCCAGCAGGCCC
  G(-2697)
CACTAGCCCCAGCTCCTCTTTGGGTCTCAGGTCCCCTGAGGATATGGGGCTTCACCTGAAATGGTCTGAGG
-2627
GCTTTTCCTTCTACACAGCAGGCATCAAGATCACCAAATAAAGGGACTATTGTGCCTGCCTGGAGCCCTGC
-2556
CAGAGGTTTGGGCCCAGAGGGGCACACAGCAGGTGCTCAATAACTGCATTAAATGCACTAACAGTGAGGAA
-2485
ACACGCCCCTCAGACTAAGCAGTGAGTGCTGCTCACAGAATAGTCCCCATTGGGGGATGGCCCAAAGAGTC
  G(-2412)
ACTTTGGTCCCTCTGGGAAGTGAGAAGGCAAGTGAGAAGGCTGTGAGTCTTAACCTCCTCTAGAGGCCCAC
-2343
AGACAGACCATTCATTTCTAAGTCTCTACCCAGAGACGCACTGTGCTTCCCACCTTGGCCTGACATGTGGC
-2272
AGGGTTAGAACACACCTCCTATCCCCTGCCAGCCCGCGTTCATGCCAAGTAGCACATATATGCCTAAACTC
-2201
AGCACTTCCATAGTGCAGTGAATACATGTGTGTGTACAGCATCTCCGCATGGATGTACAGGATGTGTGTGT
-2130
GTGTGCGTGCCCCCATGC▓▓▓▓▓▓▓▓▓▓▓▓▓▓▓▓▓▓▓TTTTTGGTAAGACAGCTAAAAAAAGAATGG▓▓▓
-2059                                                         (-1999)G
▓▓▓▓▓▓▓▓▓▓▓▓▓▓▓AGCACGCTGCAACACCTGAATATCTCCTTGAAAGGAGGGATCTTCTACTGCAGG
-1988
AGACTCGTGGTAAAGGTGGCCAAGAAACATGGCAACGGTGGGGCTGAGGGCAAATGCTGGGCAACTGTGCT
-1917                                (-1882)A
TCCCCATGTTCCCCTCCCCGTAGCCAAGACTCATTTCATGGAGGGAGATCTCAGCTTGGAAGAAGGCAGGA
-1846
GTCACTGAGCCTCCCCAATCCAAACCCCTGAGAAGTGTCCTCCCTCTGGCCTCAGACCCTGCATCCTGTGG
-1775
TCACAGACCCACAGTGAGAAAGGACCAGGCCCTAAGGAGCTGTGCTGTCTCTCCACGGCCCAGAGCGGGGG
-1704                                                (-1648)A
ATGGGGATGGGGATGGGGATGGGGATGGGGATGGGGTAGGGGTGGGGGTGCTTTGGACTAACGT
-1633
GGAGGGAATGGAAGGCAGGCCTGGTTCCACCCTGCATGCCCGACCCTGGCCCCAGCAGCCCCACAAGGAG
-1562
CTCAGCTGACCCTGGGTGTCTCCCTGTGATGGGAAGGGGTAAGACGAGGACTCAAAGGCAGAACCTGCAGA
-1491
GTGCCCCAGACGCTGATACCTGCACAGTCAGTGCCACCCACCCAGGAGTTGAGCAGGCACTGGGTTTTGGG
-1420
GTGAGGACACTGGACACCTCCCTGCTTCTTTCCCAGGCAGACAATCCTGGCGCAGCTCCCTTGGGTTGCTG
     T(-1345)
TGTCTGGTGGAGCTGATCACAGGTGAGGGGCAGAGGGCAGTCTGGGGTCCGCCTATGGCCAGAGGAGCAGG
-1278
TCAGGGCGGCGCCTTGCCGCCCCAGCTGTGGC▓▓▓▓▓▓▓▓▓▓▓▓▓▓GGTCTCGGGGCCAGCTAAC
-1207   A(-1200)                    (-1149)C

FIG. 15D

```
AATTGTTGAGCAAAATCCTTCGACAAACTTCACCTACGTGC░░░░░░░░░░░░░░░░░░░░ACTCTTAGGA
-1136
GTGGGAGAGTAATGTCTTTGCCTGTGCCCAGTGAAGGCCCATTGGAGCTGCAGCTCAGCTACCACTGTGTG
-1065
GGAGAGAAGCTGGAAGACTGAGGGCTTCCTGGGCTGCTGGCCCAGGGTTGGGAGACAGCAGTCACCTGGCT
-994
TACCAGGCCTATGCCTGAAGCCCTGGGAAGCCAGGACGCAGGCCCACGCTGGGACAAAGCTACCCTGAAG
-923
GAGGGCAAAGGCTGCCAAGGCCAACCCCATGCCTGCCAAGGCCAGGCCTGGCCCATTTGGCCAAGGCCTAA
-852
GGTGTAAAACAAGGGGAGAGGTACAAGAGGCTGTGGGGTCTGGCTGGGATCCTTGGGGTCTTCCTTCTGCA
-781
TTCTCCAAACGCCTAGAGCCAGCAGAAACGTTTCGTCTGATTAGAAGCCATCATTTCTATCCCAATCCCGG
-710
AAAATTGACTGCGGTGCAGAGAGGGAGGCCTGAGAAGCAGCCGTAGGGGAGAAGGTCCAAGCTAATTAGGA
-639
GGCAGCATCCGGGGGCCCATTAGAGCGCAGGCTGCTGTCACTCAGCCGGGCTGAGTTCCCGGGAGAAGAGG
-568
CTGGAGAAGGAGGGGCAGGCGGCCCCTCGACGAGGACACCGCTGGGAGCTGCCGGAACGGGCCCCGGCCTC
-497                            (-460)G
TGCCCCCGCCCCGGCGCTGGCTCGAAGGCGCCCCGCTCGGTGCGATCCTGTTCGGCAAACATTCACTCATCC
-426
TGGGCTGTTCTCGCCAGGGCTGGGGACTTCGAGGCGGCCGAGACGGGAGTTGATTCTAGGCGAAACAAGTC
-355
ATTTGAGGCCTGAGGTGTGCACGAGCCGCCCGGGACTCGCAGGCCAGATG░░░░░░░░░░░░░░░░░░
-284
GGAGAACTCGGTGTGTCACCGGGGAAGGAGGGAGAGGCGCGGCGAGGCCGCGGGGGCCGGGAGGCGCGG
-213
GAAGGTGGCTGCGGAGGGGAGGGCGCGGGCGAGGCAGGGAGGGAGGGAGGGCGGCAGTGAGGGCGCGGCG
-142
GCGCGGCGGCTTGGGGCTGGATTCCGCCCGCGCTCCCTCGCTCGCTCGCTCCCTCCCCAGCCCCCTCCCA
-71                                                                  -1
```

AGTATGTGTGGTTGGGGAATTCATGTGGAGGTCAGAGTGGAAGCAGGTGTGAGAGGGTCCAGCAGAAGGAA
ACATGGCTGCCAAAGTGTTTGAGTCCATTGGCAAGTTTGGCCTGGCCTTAGCTGTTGCAGGAGGCGTGGTG
AACTCTGCCTTATATAATGTGGATGCTGGGCACAGAGCTGTCATCTTTGACCGATTCCGTGGAGTGCAGGA
CATTGTGGTAGGGGAAGGGACTCATTTTCTCATCCCGTGGGTACAGAAACCAATTATCTTTGACTGCCGTT
CTCGACCACGTAATGTGCCAGTCATCACTGGTAGCAAAGATTTACAGAATGTCAACATCACACTGCGCATC
CTCTTCCGGCCTGTCGCCAGCCAGCTTCCTCGCATCTTCACCAGCATCGGAGAGGACTATGATGAGCGTGT
GCTGCCGTCCATCACAACTGAGATCCTCAAGTCAGTGGTGGCTCGCTTTGATGCTGGAGAACTAATCACCC
AGAGAGAGCTGGTCTCCAGGCAGGTGAGCGACGACCTTACAGAGCGAGCCGCCACCTTTGGGCTCATCCTG
GATGACGTGTCCTTGACACATCTGACCTTCGGGAAGGAGTTCACAGAAGCGGTGGAAGCCAAACAGGTGGC
TCAGCAGGAAGCAGAGAGGGCCAGATTTGTGGTGGAAAAGGCTGAGCAACAGAAAAAGGCGGCCATCATCT
CTGCTGAGGGCGACTCCAAGGCAGCTGAGCTGATTGCCAACTCACTGGCCACTGCAGGGGATGGCCTGATC
GAGCTGCGCAAGCTGGAAGCTGCAGAGGACATCGCGTACCAGCTCTCACGCTCTCGGAACATCACCTACCT
GCCAGCGGGGCAGTCCGTGCTCCTCCAGCTGCCCCAGTGAGGGCCCACCCTGCCTGCACCTCCGCGGGCTG
ACTGGGCCACAGCCCCGATGATTCTTAACACAGCCTTCCTTCTGCTCCCACCCCAGAAATCACTGTGAAAT
TCATGATTGGCTTAAAGTGAAGGAAATAAAGGTAAAATCACTTCAGATCTCTAATTAGTCTATCAAATGA
AACTCTTTCATTCTTCTCACATCCATCTACTTTTTTATCCACCTCCCTACCAAAAATTGCCAAGTGCCTAT
GCAAACCAGCTTTAGGTCCCAATTCGGGGCCTGCTGGAGTTCCGGCCTGGGCACCAGCATTTGGCAGCACG
CAGGCGGGGCAGTATGTGATGGACTGGGGAGCACAGGTGTCTGCCTAGATCCACGTGTGGCCTCCGTCCTG
TCACTGATGGAAGGTTTGCGGATGAGGGCATGTGCGGCTGAACTGAGAAGGCAGGCCTCCGTCTTCCCAGC
GGTTCCTGTGCAGATGCTGCTGAAGAGAGGTGCCGGGGAGGGGCAGAGAGGAAGTGGTCTGTCTGTTACCA
TAAGTCTGATTCTCTTTAACTGTGTGACCAGCGGAAACAGGTGTGTGTGAACTGGGCACAGATTGAAGAAT
CTGCCCCTGTTGAGGTGGGTGGGCCTGACTGTTGCCCCCAGGGTCCTAAAACTTGGATGGACTTGTATAG
TGAGAGAGGAGGCCTGGACCGAGATGTGAGTCCTGTTGAAGACTTCCTCTCTACCCCCCACCTTGGTCCCT
CTCAGATACCCAGTGGAATTCCAACTTGAAGGATTGCATCCTGCTGGGGCTGAACATGCCTGCCAAAGACG
TGTCCGACCTACGTTCCTGGCCCCTCGTTCAGAGACTGCCCTTCTCACGGGCTCTATGCCTGCACTGGGA
AGGAAACAAATGTGTATAAACTGCTGTCAATAAATGACACCCAGACCTTCC

FIG. 16B

MAAKVFESIGKFGLALAVAGGVVNSALYNVDAGHRAVIFDRFRGVQDIVVGEGTHFLIPWVQKPIIFDCRS
RPRNVPVITGSKDLQNVNITLRILFRPVASQLPRIFTSIGEDYDERVLPSITTEILKSVVARFDAGELITQ
RELVSRQVSDDLTERAATFGLILDDVSLTHLTFGKEFTEAVEAKQVAQQEAERARFVVEKAEQQKKAAIIS
AEGDSKAAELIANSLATAGDGLIELRKLEAAEDIAYQLSRSRNITYLPAGQSVLLQLPQ

FIG. 17A

AAGTTCGGGTCCGTAGTGGGCTAAGGGGGAGGGTTTCAAAGGGAGCGCACTTCCGCTGCCCTTTCTTTCGC
CAGCCTTACGGGCCCGAACCCTCGTGTGAAGGGTGCAGTACCTAAGCCGGAGCGGGGTAGAGGCGGGCCGG
CACCCCCTTCTGACCTCCAGTGCCGCCGGCCTCAAGATCAGACATGGCCCAGAACTTGAAGGACTTGGCGG
GACGGCTGCCCGCCGGGCCCCGGGGCATGGGCACGGCCCTGAAGCTGTTGCTGGGGGCCGGCGCCGTGGCC
TACGGTGTGCGCGAATCTGTGTTCACCGTGGAAGGCGGGCACAGAGCCATCTTCTTCAATCGGATCGGTGG
AGTGCAGCAGGACACTATCCTGGCCGAGGGCCTTCACTTCAGGATCCCTTGGTTCCAGTACCCCATTATCT
ATGACATTCGGGCCAGACCTCGAAAAATCTCCTCCCCTACAGGCTCCAAAGACCTACAGATGGTGAATATC
TCCCTGCGAGTGTTGTCTCGACCCAATGCTCAGGAGCTTCCTAGCATGTACCAGCGCCTAGGGCTGGACTA
CGAGGAACGAGTGTTGCCGTCCATTGTCAACGAGGTGCTCAAGAGTGTGGTGGCCAAGTTCAATGCCTCAC
AGCTGATCACCCAGCGGGCCCAGGTATCCCTGTTGATCCGCCGGGAGCTGACAGAGAGGGCCAAGGACTTC
AGCCTCATCCTGGATGATGTGGCCATCACAGAGCTGAGCTTTAGCCGAGAGTACACAGCTGCTGTAGAAGC
CAAACAAGTGGCCCAGCAGGAGGCCCAGCGGGCCCAATTCTTGGTAGAAAAAGCAAAGCAGGAACAGCGGC
AGAAAATTGTGCAGGCCGAGGGTGAGGCCGAGGCTGCCAAGATGCTTGGAGAAGCACTGAGCAAGAACCCT
GGCTACATCAAACTTCGCAAGATTCGAGCAGCCCAGAATATCTCCAAGACGATCGCCACATCACAGAATCG
TATCTATCTCACAGCTGACAACCTTGTGCTGAACCTACAGGATGAAAGTTTCACCAGGGGAAGTGACAGCC
TCATCAAGGGTAAGAAATGAGCCTAGTCACCAAGAACTCCACCCCCAGAGGAAGTGGATCTGCTTCTCCAG
TTTTTGAGGAGCCAGCCAGGGGTCCAGCACAGCCCTACCCCGCCCCAGTATCATGCGATGGTCCCCCACAC
CGGTTCCCTGAACCCCTCTTGGATTAAGGAAGACTGAAGACTAGCCCCTTTTCTGGGAAATTACTTTCCTC
CTCCCTGTGTTAACTGGGGCTGTTGGGGACAGTGCGTGATTTCTCAGTGATTTCCTACAGTGTTGTTCCCT
CCCTCAAGGCTGGGAGGAGATAAACACCAACCCAGGAATTCTCAATAAATTTTTATTACTTAACCTG

FIG. 17B

MAQNLKDLAGRLPAGPRGMGTALKLLLGAGAVAYGVRESVFTVEGGHRAIFFNRIGGVQQDTILAEGLHFR
IPWFQYPIIYDIRARPRKISSPTGSKDLQMVNISLRVLSRPNAQELPSMYQRLGLDYEERVLPSIVNEVLK
SVVAKFNASQLITQRAQVSLLIRRELTERAKDFSLILDDVAITELSFSREYTAAVEAKQVAQQEAQRAQFL
VEKAKQEQRQKIVQAEGEAEAAKMLGEALSKNPGYIKLRKIRAAQNISKTIATSQNRIYLTADNLVLNLQD
ESFTRGSDSLIKGKK (SEQ ID NO :1)

AGTTCCATACTCCATCTGTGCCTCACTGGCGGCCAGTCCTGCTCAAATACATCCTGGCTCT

(SEQ ID NO :16)
5' ... TCACTGGCGGCAGTCCTGCT ... 3'
        ├1 ─ ├10 ─ ├20
3' ... AGTGACCGCCGTCAGGACGA ... 5'
(SEQ ID NO :33)

*AciI
*Fnu4HI
BsrI (marking top strand)
BsrI, *AciI (marking bottom strand)

Fig. 18B

(SEQ ID NO :2)
5' ... TCACTGGTGGCAGTCCTGCT ... 3'
        ├1 ─ ├10 ─ ├20
3' ... AGTGACCACCGTCAGGACGA ... 5'
(SEQ ID NO :34)

BsrI

Fig. 18C

SEQUENCE LISTING

<160> NUMBER OF SEQ ID NOS: 70

<210> SEQ ID NO 1
<211> LENGTH: 61
<212> TYPE: DNA
<213> ORGANISM: Homo sapiens

<400> SEQUENCE: 1
agttccatac tcccatctgt gcctcactgg cggcagtcct gctcaaatac atcctggctc    60
t    61

<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2
tcactggtgg cagtcctgct    20

<210> SEQ ID NO 3

```
<211> LENGTH: 18
<212> TYPE: DNA
<213> ORGANISM: Homo sapiens

<400> SEQUENCE: 3
cgtttggcgc cctgtgat                                                   18

<210> SEQ ID NO 4
<211> LENGTH: 18
<212> TYPE: DNA
<213> ORGANISM: Homo sapiens

<400> SEQUENCE: 4
attttcgcgc gctttggc                                                   18

<210> SEQ ID NO 5
<211> LENGTH: 20
<212> TYPE: DNA
<213> ORGANISM: Homo sapiens

<400> SEQUENCE: 5
tttagcgcgg tgagtttgaa                                                 20

<210> SEQ ID NO 6
<211> LENGTH: 21
<212> TYPE: DNA
<213> ORGANISM: Homo sapiens

<400> SEQUENCE: 6
gttttcgcgc ttaaatttga g                                               21

<210> SEQ ID NO 7
<211> LENGTH: 21
<212> TYPE: DNA
<213> ORGANISM: Homo sapiens

<400> SEQUENCE: 7
gatttggcgc gtaaaagtgg c                                               21

<210> SEQ ID NO 8
<211> LENGTH: 21
<212> TYPE: DNA
<213> ORGANISM: Homo sapiens

<400> SEQUENCE: 8 ttttcgcgc ccaatagtgt t                                                21

<210> SEQ ID NO 9
<211> LENGTH: 20
<212> TYPE: DNA
<213> ORGANISM: Homo sapiens

<400> SEQUENCE: 9
aatttcgcgc caaacttggg                                                 20

<210> SEQ ID NO 10
<211> LENGTH: 18
<212> TYPE: DNA
<213> ORGANISM: Homo sapiens

<400> SEQUENCE: 10
aacttcgcgc caatcggc                                                   18
```

```
<210> SEQ ID NO 11
<211> LENGTH: 22
<212> TYPE: DNA
<213> ORGANISM: Homo sapiens

<400> SEQUENCE: 11
tttttcccgc caagcctctg ag                                            22

<210> SEQ ID NO 12
<211> LENGTH: 20
<212> TYPE: DNA
<213> ORGANISM: Homo sapiens

<400> SEQUENCE: 12
atagtcgcgg gatacttgaa                                               20

<210> SEQ ID NO 13
<211> LENGTH: 20
<212> TYPE: DNA
<213> ORGANISM: Homo sapiens

<400> SEQUENCE: 13
gggctggcgg aaggtttgaa                                               20

<210> SEQ ID NO 14
<211> LENGTH: 20
<212> TYPE: DNA
<213> ORGANISM: Homo sapiens

<400> SEQUENCE: 14
gacctggcgg gagatttggc                                               20

<210> SEQ ID NO 15
<211> LENGTH: 20
<212> TYPE: DNA
<213> ORGANISM: Homo sapiens

<400> SEQUENCE: 15
cacttggcgg gagataggaa                                               20

<210> SEQ ID NO 16
<211> LENGTH: 20
<212> TYPE: DNA
<213> ORGANISM: Homo sapiens

<400> SEQUENCE: 16
tcactggcgg cagtcctgct                                               20

<210> SEQ ID NO 17
<211> LENGTH: 30
<212> TYPE: PRT
<213> ORGANISM: Homo sapiens

<400> SEQUENCE: 17

Arg Val Pro Ser Ala Lys Ala Val Thr Ser Gly Leu Pro Gly Asp Thr
1               5                   10                  15

Ala Leu Leu Leu Pro Pro Ser Pro Arg Pro Ser Pro Arg Val
            20                  25                  30

<210> SEQ ID NO 18
<211> LENGTH: 12
<212> TYPE: PRT
<213> ORGANISM: Homo sapiens
```

<400> SEQUENCE: 18

Arg Phe Asp Ala Gly Glu Leu Ile Thr Gln Arg Glu
1               5                   10

<210> SEQ ID NO 19
<211> LENGTH: 18
<212> TYPE: PRT
<213> ORGANISM: Homo sapiens

<400> SEQUENCE: 19

Arg Asn Ile Thr Tyr Leu Pro Ala Gly Gln Ser Val Leu Leu Gln Leu
1               5                   10                  15

Pro Gln

<210> SEQ ID NO 20
<211> LENGTH: 12
<212> TYPE: PRT
<213> ORGANISM: Homo sapiens

<400> SEQUENCE: 20

Lys Asp Leu Gln Asn Val Asn Ile Thr Leu Arg Ile
1               5                   10

<210> SEQ ID NO 21
<211> LENGTH: 20
<212> TYPE: PRT
<213> ORGANISM: Homo sapiens

<400> SEQUENCE: 21

Arg Ser Arg Asn Ile Thr Tyr Leu Pro Ala Gly Gln Ser Val Leu Leu
1               5                   10                  15

Gln Leu Pro Gln
            20

<210> SEQ ID NO 22
<211> LENGTH: 22
<212> TYPE: PRT
<213> ORGANISM: Homo sapiens

<400> SEQUENCE: 22

Lys Ala Ala Glu Leu Ile Ala Asn Ser Leu Ala Thr Ala Gly Asp Gly
1               5                   10                  15

Leu Ile Glu Leu Arg Lys
            20

<210> SEQ ID NO 23
<211> LENGTH: 17
<212> TYPE: PRT
<213> ORGANISM: Homo sapiens

<400> SEQUENCE: 23

Arg Ala Ala Gln Asn Ile Ser Lys Thr Ile Ala Thr Ser Gln Asn Arg
1               5                   10                  15

Ile

<210> SEQ ID NO 24
<211> LENGTH: 16
<212> TYPE: PRT
<213> ORGANISM: Homo sapiens

<400> SEQUENCE: 24

Arg Gln Lys Ile Val Gln Ala Glu Gly Glu Ala Glu Ala Ala Lys Met
1               5                   10                  15

<210> SEQ ID NO 25
<211> LENGTH: 10
<212> TYPE: PRT
<213> ORGANISM: Homo sapiens

<400> SEQUENCE: 25

Arg Leu Gly Leu Asp Tyr Glu Glu Arg Val
1               5                   10

<210> SEQ ID NO 26
<211> LENGTH: 10
<212> TYPE: PRT
<213> ORGANISM: Homo sapiens

<400> SEQUENCE: 26

Arg Ala Gln Val Ser Leu Leu Ile Arg Arg
1               5                   10

<210> SEQ ID NO 27
<211> LENGTH: 13
<212> TYPE: PRT
<213> ORGANISM: Homo sapiens

<400> SEQUENCE: 27

Arg Val Leu Pro Ser Ile Val Asn Glu Val Leu Lys Ser
1               5                   10

<210> SEQ ID NO 28
<211> LENGTH: 10006
<212> TYPE: DNA
<213> ORGANISM: Homo sapiens

<400> SEQUENCE: 28

```
cccaaattgt ctatctgtga tagtggctgt gccccttcgg gccctgagca ccctgtgtcc      60
tgtgcagcag tcagatatct ggagggagac tgaggcactg gctgcagagc ttgtgatcat     120
gagagagact cactaggact acagatgggt aaactgaggc cttcgagggg gcagctccag     180
aaaggcaggg gccataatgt ctcaccttca tatttcccgt gccaagctgt ggccttctgc     240
attcatggca gatgagtgga caaaggctga tggactgatg gagaaacaaa gggatagatg     300
gagcagctgg gcagctcagc aaatgatgct gcaatgatct gcttccaact cacctcaaat     360
ccatccttct ctctccaggc agagtgggct tttaagatac acatctggcc aggtctctca     420
ctgttcaaac ccttcatctg ctccttttg ccttcaggat aacatcccac cctcctatca     480
aggactatgg agccctgtgg gatctggttc ccacttgatt ctccaacttc ctcttcccct     540
atgccctgcc ttctcatctg ttccagtgct attatgaagc cacacgttct tcctttatta     600
tcaagcatac cacagtttat ctcacctcag aggctttgca cagtatattt tcctagggag     660
gggtccccag gtggtagaaa aacggttaca gccaactcct ccatgtgtca ctcaagaccc     720
ttcaacagca ggctgcagat ttcctctcca gcactgtgct ccaactgtgt aatggatttc     780
tgtgtctgcc tccttgactc aacccaaatg aacaagagcc atctatctct gtatctctgc     840
aatcacaggc acaaaatagg tgctctctac atttttcca acctgagagg ccattctaga     900
agggtctcag gccacggttc tgtccagtat tccatgcaga tgctgacagg actgcaatta     960
aaaaaatact tgagatgccc aaatgcccaa atagcttctc attttgcttt gactaccaat    1020
aattgcacag tgcaatagaa taatgctcaa atacattaac atcttacttg atcctagggg    1080
```

```
gtcctctcta cttttaaagc ctcaaacttc ctccctctca caggtgaaaa ggggagtaca    1140
aatacattcc ctcccttgct ctgcggatcc attcctacag gtagtcaaga ctctgagctt    1200
cccctctgac tttctggcag tgcttcacct ctccccacag atgagtgcag gaacaattct    1260
aacagacttc agactcttcc aacagagcca atccctcccc atcacgttgg agtggacttg    1320
ctacccacac catcaacagg cccctgagaa acttcacagg gcaggggctt ctttggtaaa    1380
accaaccctt tccttccacc agctcagaga agttgttcca gatagatgcc aggattcttg    1440
gaggagcatg gtgattctgg ggtggagcct ctgaccctgg ccaaccaaag gcctgagcca    1500
ctcttccccc acaaagtgat tggcgcagga gtgggcatgt aagctggacc cagccaatca    1560
gcataaccaa atcccttgcc caccctgggg agggtcctat agttgttgcc aagagaggct    1620
cacccctgtt ctcaagaagc ttacaactgg taggggcaac aggttttaat ctatcattac    1680
acaaatattt aatttcaata ctgttgcaat aagagctatg aaggaaaaga acactccccc    1740
tacttttact tggtgttaag atttgaagaa gaaaaaaaaa aaacactgcc tgaaggattg    1800
ttatggcctt ctatataata gtggctgcag acatttgccc attatgttca gcatgaaccc    1860
atgtgacaaa ttcatcaaag cgttttgcac tagggagaaa aatttgtatt agaggaagca    1920
cagcagtttg gactgaaaga caaagaaaat tcagccaatt ctgctgatct ttttttgatgg    1980 ggcacctgga agctgaaagc taaagtggta ctcaggaaca gggactgcta cttctgttcc    2040
tggtgaatcc tgccccaaac ctcctctctc tctgattcct gattccactg tgccagtggg    2100
aatatatgct ccccaagatg tcaaaactaa agggaaattg caaaaaatat atacatatat    2160
ttttagagag aaaataagat tataaaaaat gtgttttgta cccccaagt ttcactaaga    2220 acttcctgac ttccaggccc tggttgtgcc ccacgcacca gcctgccag ctttcctgga    2280 ccaaacttcc tagcacctaa gcaggggatg agggcagata aactaaatca gaaaagggat    2340
ctgttcctcc tagactcaac caacatgacc accgtgggga agaagaaac aaaaacaaga    2400 gcaaactctc ttaaagagca gcctggcagc tatcaccatt agcattcagc ccctctgtcc    2460
acaggactca ggaccaaacc cctcaccttc actatcccat ccgtttccca agaagcagaa    2520
atacttattc tcacatttca cagatgggga agctgaggct aggagaggtt atgttatttg    2580
ccaaagccac acaactagta aaagccactg acaagattct ggctcaggcc atcaggtgcc    2640
agaggcagca ttttttggca ccacaggccc tgcctgggaa caagagcatg cagaaaatct    2700
cacaagagat gggaacaaaa tttggaaaat tgctagcgtg cagggagggg ggaaggtgtg    2760
atttcctgct acagacgcca gagtaaaagc caccccagga gtgcctgtgc agccctccat    2820
agtaaggtcc agcggctgca tttatgccca agatgccccc tggtgcttgg agtggaagga    2880
agattccaga gacaagatta gaaacttctc agcttagcag ctctagggct ggacccgcca    2940
acaagccatt ttacacataa agcagtcaat gggagggggt gacgtaggg ggctaaactc    3000 cccacagcac agggtccaag ttggtagact gcactttctc caggcgcagg tccgctagtg    3060
ccggcatcgg ggactcgtta tcttaacttg cgaccctggg tgcacagagc cctgcacaca    3120
ccactggaga ggggttcctg ctgtcgaggg ttgagaggag ggtatggagt ccctggaaca    3180
gcacgacagg gtgcagaggc cacctggcag ggcctgaaca ccgaggcctc tgtgagcttg    3240
ggtcgggccg gcttcccgct tcggaggttg gggaggggt cgtgggtctc tgcgttccca    3300
ggccaagcgg ccctggaggc acggactagc aggacgccga ggtggcgcgg gtcgcggcct    3360
ctcccgcagc agctgtcggc gagaaccagg caggaggcg ccgctgctga ctgcatctca    3420
tgaaagattc aggcccggct gccgcgctgc catctcccgg caccttgcgc cggaaacggt    3480
```

```
cgctctggag cccgtggccg tcggcgggca ggcttagccg ctccagtccc tgagaaaggc    3540
aggccacagc ccgacctgcc ctgtggtccc atcccataat cccaacagca agcaggctca    3600
ggctgggcac ttcggggtac caggagtagg ttcggccaac tggtttccac catgaggctt    3660
cgcgcacagg gttatctggc cacgaggcaa cgctggggag ccctgtggcc tgagggtggg    3720
caaaggacag gctcccagtt cccttgcgtc cagcccgtct cccagcggca gccagccagg    3780
aacggcctgc ggggccacag gggtggaggc gtcaccgttc gcaggcccgc agcaggatgg    3840
tcgctggggg atgtgcaggc ataggggttg acaaggggc cccagaagtg tctgtcctga    3900 gggggttggtg tgccctttcc tcaccagccc agccctgag gagagggaag aaggcaattc    3960
ccccaaccag ggcaggtcgg gcggttgccc caccctaaca cccctaccc ccaaacacag    4020 aaaacctggg gtctgtcctc aaacctccct ggctgccacg ctctgggcag cggactctcc    4080
ctgccaacac gcaagaccag ctccctcccg caggctgagc agaaagaaga aaggtccaat    4140
ctcaaaaccc caaactcgac caccagcccc cgtctaaacg gaagtagggc cagcccctca    4200
cgagtcaggt gggaaactgg gcccagggag agaaagtgcc ccagggccag gctgggaccc    4260
gctctggctt cgtccgcatg cggcagggcc cctccacgga ggtcccaggg cgcgctcccc    4320
ggcctcgagg cccggccgcc agccgcgcgg accccagcct acgccccgag ggaggccagg    4380 accctagcc ggcgggactg cgccgccgcc ctctccccgc aggtcccggc gaacacctag    4440
cttcccctcc ccccacccctt cccgcctccc ggccagtgtc cccgccttcc ccgcgggcga    4500
cgggcggcgg cggcgggagg agcgggccga gccgaggaag ccccggcctc gcgcgctggg    4560
atgtagcgaa ccagcagggg ccgaagaacc gtgcagtgcc agagccagag ctggatccgg    4620
ggccccagcc ggagccgaaa cctgagccag agtccgcggc gggcgagccc ggagcccacg    4680
agccgcagac gcagcgctgc ccaggtgggg taagagacgc tgggctaggg gcgcagggtc    4740
tccgcggtgg aggggcgcag ggaggtggcg gccgagtcct gcgcagtttg ctcctggcgt    4800
gtgtgggtcc accggcggc gcgggacagc gcaaggcgcg gaaggtcagg agccttcgag    4860
gcagcgcgag gagctcgttc ctgcgcccag ggcacagtca tagccgccgt caccgggtgc    4920
tacctcaccc aaccggcggg atcaaccctc tgctttggct ccgggcacct caagagggta    4980
gcagcctcgg gggcacgggc cacggccccg cgaagggcac aacctgagaa gcccgtggca    5040 gccctcgca gcgtcgggtg acacaggct ccccccacccc caggagaagt gggcaggaga    5100
gagggccgcc cgctgctccc cgctgcgtcc agggatggag ggccccacca cccatggaat    5160
tgctggcccc tctgcgtggc ccgggacttc agccgtggct tcgcgtcaag agggtatttt    5220
tcctaaacga aaccgcttcg ttcgttcgtt cgttcgttcg ttcgggcagc aatgccgcag    5280
aaaagcagca gacgtcggtc cgcgcccctgg ctctcttcgc cccggacccc gacgtcccgc    5340
cgcagcgctc ggaggtgccc ccagcccaag gcagcctgct ctcgccggca caggtcgggc    5400 ttttcttcc caggagagaa accccaattc ccttcgtaac gtccaataaa gacattcccg    5460
cggcttctcc caggtttggt tgttgacgca gggtcccgga gcacgcagtc gcttctcaag    5520
aaccgggtct cggatttctg aaattgacca gcttcgtaaa ttggagccta ttctcccgcg    5580
gcaaaggcag ggccccaaag ccgggatcgc agtaatggga accccaggct ggaatccggg    5640
tcccaagctt ttccgatttta ggaattcccc gaatctacaa atatttagtc cacttttctg    5700
aaaaactaaa ttctgaaaaa cacaaattct cttgacatcc ctgtgacctc tgaaagccac    5760
cagggccaga gggaggaaat cccaggttgc tgtccactgg gggaggattc aggtctaggg    5820
```

-continued

```
ttcaggtcta cggtagtcag ggcaaaagct acaggcagca ggggcagcac aggagacttg    5880
ctgtccccgt gcccttttcc ggggctgctt tcggcctccc gcatctcttc cagggaaagg    5940
aaaagaggtg ggctggggct tggagaccag gctgtctgga ctctaggatg cagaggcctc    6000
cagacaggct cagggtgctc ttctcccatg aaagcagccg ctgggaggag gaggctatgg    6060
tgcatccata agttgcccct ctgctcccca gttgtgcgac cagctgctac ctccttccta    6120
gtcttcttcc ccacagctca gccattctca ggaaccagac agcgtccatg gacttaggtg    6180
agagatgggc cgggtagagc catgggtcct accagccgct gactgagcgg cccacggcac    6240
agagtcctga gttccatact cccatctgtg cctcactggc ggcagtcctg ctcaaataca    6300
tcctggctct ccccgggaca ggctggggat ccccatttgg caggaagcct cagactgggg    6360
tcccaggaag cctaaaggag ccagtgaggt cttttccagcc cctacctgag caccctcctc    6420
cccacttacc cagtaattgc tgtattcaaa gaaacgggag cttttattgg ggaggggtg    6480 ttagatcagg cagaaagagg taggtggtcc aaacctgcac tcccaaaaca gggttttcaa    6540
gtttgaactt ctccacggac taagaggctt agggctggaa tgtcccagag agtcatggat    6600
agccctggtg gcaggccatg gcacattcct tccttttcc taaaataccct tgattctggg    6660 agcaaggatt agggcacggt gccccgtgg gtgggtagaa ggatgccccc ccactgagag    6720
ccttccaacc acccttccca aattacatta ctaaaccatt cttgggcaca gggtgttttt    6780
agtgagccag gctcaggaa gggtcctcat ggtgactact caacccccac aacagcccaa    6840
gctcttctgc tcagcccagc caagaccccta aactccaaaa ttcttgaaaa tcagagaatc    6900
attgctggct ttgtgtggtc acggaggggt ggggaacagg gcacatggtt ccagctccac    6960 taagcccccct tccctcctct cttcgtgtcc catcagcaag tgagctggat gctgaagcag    7020
caggcagagt ccggtgttgg acatgggaac tgaggcacag tgcagatcaa gccttaacct    7080
tgagggaaac acaggtcaca tagcacagct gggggaacac aaagcctctg cttactcctg    7140
aaagagtgct gttttctgtc ctgtatgtgt gacgtgtctg tgagcgtgca agaagcccct    7200
atcttgactg ggacaatggc cagtgagtgt agctgggaa gaattgagag catgtccagg    7260
tcccttcccc agccaacgcc caagatcagg ccacagcctc ctcacaatca attgcctcct    7320
cactccttga tcactcagtg ctgcccaggc ccagcagaac agactctgcc agcaggcccc    7380
actagcccca gctcctcttt gggtctcagg tcccctgagg atatgggct tcacctgaaa    7440 tggtctgagg gcttttcctt ctacacagca ggcatcaaga tcaccaaata aagggactat    7500
tgtgcctgcc tggagccctg ccagaggttt gggcccagag gggcacacag caggtgctca    7560
ataactgcat taaatgcact aacagtgagg aaacacgccc ctcagactaa gcagtgagtg    7620
ctgctcacag aatagtcccc attggggat ggcccaaaga gtcactttgg tccctctggg    7680
aagtgagaag gcaagtgaga aggctgtgag tcttaacctc ctctagaggc ccacagacag    7740
accattcatt tctaagtctc tacccagaga cgcactgtgc ttcccacctt ggcctgacat    7800
gtggcagggt tagaacacac ctcctatccc ctgccagccc gcgttcatgc caagtagcac    7860
atatatgcct aaactcagca cttccatagt gcagtgaata catgtgtgtg tacagcatct    7920
ccgcatggat gtacaggatg tgtgtgtgtg tgcgtgcccc catgctgtct gcattcaggc    7980
tgttcttttt ggtaagacag ctaaaaaaag aatggtctgt gaagggacac tccctagcac    8040
gctgcaacac ctgaatatct ccttgaaagg agggatcttc tactgcagga gactcgtggt    8100
aaaggtggcc aagaaacatg gcaacggtgg ggctgagggc aaatgctggg caactgtgct    8160
tccccatgtt cccctccccg tagccaagac tcatttcatg gagggagatc tcagcttgga    8220
```

```
agaaggcagg agtcactgag cctccccaat ccaaacccct gagaagtgtc ctccctctgg      8280
cctcagaccc tgcatcctgt ggtcacagac ccacagtgag aaaggaccag gccctaagga      8340
gctgtgctgt ctctccacgg cccagagcgg gggatgggga tgggatggg atggggatg       8400 gggatgggga tggggtagg ggtggggtg ctttggacta acgtggaggg aatggaaggc       8460
aggcctggtt ccaccctgca tgcccgaccc tggccccagc agccccaca aggagctcag      8520 ctgaccctgg gtgtctccct gtgatgggaa ggggtaagac gaggactcaa aggcagaacc     8580
tgcagagtgc cccagacgct gatacctgca cagtcagtgc cacccaccca ggagttgagg     8640
aggcactggg ttttggggtg aggacactgg acacctccct gcttctttcc caggcagaca    8700
atcctggcgc agctcccttg ggttgctgtg tctggtggag ctgatcacag gtgaggggca    8760
gagggcagtc tggggtccgc ctatggccag aggagcaggt cagggcggcg ccttgccgcc    8820
ccagctgtgg cctgtttgct caagacgctg aggtctcggg gccagctaac aattgttgag    8880
caaaatcctt cgacaaactt cacctacgtg caaggactcg aggagggaat cactcttagg    8940
agtgggagag taatgtcttt gcctgtgccc agtgaaggcc cattggagct gcagctcagc    9000
taccactgtg tgggagagaa gctggaagac tgagggcttc ctgggctgct ggcccagggt    9060
tgggagacag cagtcacctg gcttaccagg cctatgcctg aagccctggg aagccaggac    9120
gcaggcccca ggctgggaca aagctaccct gaaggagggc aaaggctgcc aaggccaacc    9180
ccatgcctgc caaggccagg cctggcccat ttggccaagg cctaaggtgt aaaacaaggg    9240
gagaggtaca agaggctgtg gggtctggct gggatccttg gggtcttcct tctgcattct    9300
ccaaacgcct agagccagca gaaacgtttc gtctgattag aagccatcat ttctatccca    9360
atcccggaaa attgactgcg gtgcagagag ggaggcctga gaagcagccg taggggagaa    9420
ggtccaagct aattaggagg cagcatccgg gggcccatta gagcgcaggc tgctgtcact    9480
cagccgggct gagttcccgg gagaagaggc tggagaagga gggcaggcg gcccctcgac    9540 gaggacaccg ctgggagctg ccggaacggg ccccgggctc tgccccgcc ccggcgctgg    9600 ctcgaaggcg cccgctcggt gcgatcctgt tcggcaaaca ttcactcatc ctgggctgtt    9660
ctcgccaggg ctggggactt cgaggcggcc gagacgggag ttgattctag gcgaaacaag    9720
tcatttgagg cctgaggtgt gcacgagccg cccgggactc gcaggccaga tgcgtttctt    9780
ttgtgaggcc gagggagaac tcggtgtgtc accggggaag gagggagagg cgcggcgagg    9840 ccgcggggggg cggggaggcg gcgggaaggt ggctgcggag ggggagggcg cgggcgaggc    9900
agggagggag ggaggcggc agtgagggcg cggcggcgcg ggcggcttgg ggctggattc     9960
cgcccgcgct ccctcgctcg ctcgctccct ccccagcccc ctccca                   10006
```

<210> SEQ ID NO 29  
<211> LENGTH: 1826  
<212> TYPE: DNA  
<213> ORGANISM: Homo sapiens

<400> SEQUENCE: 29

```
agtatgtgtg gttggggaat tcatgtggag gtcagagtgg aagcaggtgt gagagggtcc       60
agcagaagga aacatggctg ccaaagtgtt tgagtccatt ggcaagtttg gcctggcctt      120
agctgttgca ggaggcgtgg tgaactctgc cttatataat gtggatgctg ggcacagagc      180
tgtcatcttt gaccgattcc gtggagtgca ggacattgtg gtaggggaag ggactcattt      240
tctcatcccg tgggtacaga aaccaattat ctttgactgc cgttctcgac cacgtaatgt      300
```

```
gccagtcatc actggtagca aagatttaca gaatgtcaac atcacactgc gcatcctctt    360
ccggcctgtc gccagccagc ttcctcgcat cttcaccagc atcggagagg actatgatga    420
gcgtgtgctg ccgtccatca caactgagat cctcaagtca gtggtggctc gctttgatgc    480
tggagaacta atcacccaga gagagctggt ctccaggcag gtgagcgacg accttacaga    540
gcgagccgcc acctttgggc tcatcctgga tgacgtgtcc ttgacacatc tgaccttcgg    600
gaaggagttc acagaagcgg tggaagccaa acaggtggct cagcaggaag cagagagggc    660
cagatttgtg gtggaaaagg ctgagcaaca gaaaaaggcg gccatcatct ctgctgaggg    720
cgactccaag gcagctgagc tgattgccaa ctcactggcc actgcagggg atggcctgat    780
cgagctgcgc aagctggaag ctgcagagga catcgcgtac cagctctcac gctctcggaa    840
catcacctac ctgccagcgg ggcagtccgt gctcctccag ctgccccagt gagggcccac    900
cctgcctgca cctccgcggg ctgactgggc cacagccccg atgattctta acacagcctt    960
ccttctgctc ccaccccaga aatcactgtg aaatttcatg attggcttaa agtgaaggaa   1020
ataaaggtaa aatcacttca gatctctaat tagtctatca aatgaaactc tttcattctt   1080
ctcacatcca tctacttttt tatccacctc cctaccaaaa attgccaagt gcctatgcaa   1140
accagcttta ggtcccaatt cggggcctgc tggagttccg gcctgggcac cagcatttgg   1200
cagcacgcag gcggggcagt atgtgatgga ctggggagca caggtgtctg cctagatcca   1260
cgtgtggcct ccgtcctgtc actgatgaa ggtttgcgga tgaggcatg tgcggctgaa    1320
ctgagaaggc aggcctccgt cttcccagcg gttcctgtgc agatgctgct gaagagaggt   1380
gccggggagg ggcagagagg aagtggtctg tctgttacca taagtctgat tctctttaac   1440
tgtgtgacca gcggaaacag gtgtgtgtga actgggcaca gattgaagaa tctgcccctg   1500
ttgaggtggg tgggcctgac tgttgccccc cagggtccta aaacttggat ggacttgtat   1560
agtgagagag gaggcctgga ccgagatgtg agtcctgttg aagacttcct ctctacccct   1620
caccttggtc cctctcagat acccagtgga attccaactt gaaggattgc atcctgctgg   1680
ggctgaacat gcctgccaaa gacgtgtccg acctacgttc ctggccccct cgttcagaga   1740
ctgcccttct cacgggctct atgcctgcac tgggaaggaa acaaatgtgt ataaactgct   1800
gtcaataaat gacacccaga ccttcc                                        1826
```

<210> SEQ ID NO 30
<211> LENGTH: 272
<212> TYPE: PRT
<213> ORGANISM: Homo sapiens

<400> SEQUENCE: 30

```
Met Ala Ala Lys Val Phe Glu Ser Ile Gly Lys Phe Gly Leu Ala Leu
1               5                   10                  15

Ala Val Ala Gly Gly Val Val Asn Ser Ala Leu Tyr Asn Val Asp Ala
            20                  25                  30

Gly His Arg Ala Val Ile Phe Asp Arg Phe Arg Gly Val Gln Asp Ile
        35                  40                  45

Val Val Gly Glu Gly Thr His Phe Leu Ile Pro Trp Val Gln Lys Pro
    50                  55                  60

Ile Ile Phe Asp Cys Arg Ser Arg Pro Arg Asn Val Pro Val Ile Thr
65                  70                  75                  80

Gly Ser Lys Asp Leu Gln Asn Val Asn Ile Thr Leu Arg Ile Leu Phe
                85                  90                  95

Arg Pro Val Ala Ser Gln Leu Pro Arg Ile Phe Thr Ser Ile Gly Glu
```

```
            100                 105                 110
Asp Tyr Asp Glu Arg Val Leu Pro Ser Ile Thr Thr Glu Ile Leu Lys
        115                 120                 125

Ser Val Ala Arg Phe Asp Ala Gly Glu Leu Ile Thr Gln Arg Glu
130                 135                 140

Leu Val Ser Arg Gln Val Ser Asp Asp Leu Thr Glu Arg Ala Ala Thr
145                 150                 155                 160

Phe Gly Leu Ile Leu Asp Asp Val Ser Leu Thr His Leu Thr Phe Gly
                165                 170                 175

Lys Glu Phe Thr Glu Ala Val Glu Ala Lys Gln Val Ala Gln Gln Glu
                180                 185                 190

Ala Glu Arg Ala Arg Phe Val Val Glu Lys Ala Glu Gln Gln Lys Lys
            195                 200                 205

Ala Ala Ile Ile Ser Ala Glu Gly Asp Ser Lys Ala Ala Glu Leu Ile
            210                 215                 220

Ala Asn Ser Leu Ala Thr Ala Gly Asp Gly Leu Ile Glu Leu Arg Lys
225                 230                 235                 240

Leu Glu Ala Ala Glu Asp Ile Ala Tyr Gln Leu Ser Arg Ser Arg Asn
                245                 250                 255

Ile Thr Tyr Leu Pro Ala Gly Gln Ser Val Leu Leu Gln Leu Pro Gln
                260                 265                 270

<210> SEQ ID NO 31
<211> LENGTH: 1416
<212> TYPE: DNA
<213> ORGANISM: Homo sapiens

<400> SEQUENCE: 31
aagttcgggt ccgtagtggg ctaagggga gggtttcaaa gggagcgcac ttccgctgcc      60 cttctttcg ccagccttac gggcccgaac cctcgtgtga agggtgcagt acctaagccg     120
gagcggggta gaggcgggcc ggcacccct tctgacctcc agtgccgccg gcctcaagat     180
cagacatggc ccagaacttg aaggacttgg cgggacggct gcccgccggg cccgggca     240 tgggcacggc cctgaagctg ttgctggggg ccggcgccgt ggcctacggt gtgcgcgaat    300
ctgtgttcac cgtggaaggc gggcacagag ccatcttctt caatcggatc ggtggagtgc    360
agcaggacac tatcctggcc gagggccttc acttcaggat cccttggttc agtaccccca    420
ttatctatga cattcgggcc agacctcgaa aaatctcctc ccctacaggc tccaaagacc    480
tacagatggt gaatatctcc ctgcgagtgt tgtctcgacc caatgctcag gagcttccta    540
gcatgtacca gcgcctaggg ctggactacg aggaacgagt gttgccgtcc attgtcaacg    600
aggtgctcaa gagtgtggtg gccaagttca atgcctcaca gctgatcacc agcgggccc    660 aggtatccct gttgatccgc cgggagctga cagagagggc caaggacttc agcctcatcc    720
tggatgatgt ggccatcaca gagctgagct tagccgaga gtacacagct gctgtagaag    780
ccaaacaagt ggcccagcag gaggcccagc gggcccaatt cttggtagaa aaagcaaagc    840
aggaacagcg gcagaaaatt gtgcaggccg agggtgaggc cgaggctgcc aagatgcttg    900
gagaagcact gagcaagaac cctggctaca tcaaacttcg caagattcga gcagcccaga    960
atatctccaa gacgatcgcc acatcacaga atcgtatcta tctcacagct gacaaccttg   1020
tgctgaacct acaggatgaa agtttcacca ggggaagtga cagcctcatc aagggtaaga   1080
aatgagccta gtcaccaaga actccacccc cagaggaagt ggatctgctt ctccagtttt   1140
tgaggagcca gccaggggtc cagcacagcc ctacccccgcc ccagtatcat gcgatggtcc   1200
```

```
cccacaccgg ttccctgaac ccctcttgga ttaaggaaga ctgaagacta gccccttttc    1260
tgggaaatta ctttcctcct ccctgtgtta actggggctg ttggggacag tgcgtgattt    1320
ctcagtgatt tcctacagtg ttgttccctc cctcaaggct gggaggagat aaacaccaac    1380
ccaggaattc tcaataaatt tttattactt aacctg                              1416
```

<210> SEQ ID NO 32
<211> LENGTH: 299
<212> TYPE: PRT
<213> ORGANISM: Homo sapiens

<400> SEQUENCE: 32

```
Met Ala Gln Asn Leu Lys Asp Leu Ala Gly Arg Leu Pro Ala Gly Pro
1               5                   10                  15

Arg Gly Met Gly Thr Ala Leu Lys Leu Leu Leu Gly Ala Gly Ala Val
            20                  25                  30

Ala Tyr Gly Val Arg Glu Ser Val Phe Thr Val Glu Gly Gly His Arg
        35                  40                  45

Ala Ile Phe Phe Asn Arg Ile Gly Gly Val Gln Gln Asp Thr Ile Leu
    50                  55                  60

Ala Glu Gly Leu His Phe Arg Ile Pro Trp Phe Gln Tyr Pro Ile Ile
65                  70                  75                  80

Tyr Asp Ile Arg Ala Arg Pro Arg Lys Ile Ser Ser Pro Thr Gly Ser
                85                  90                  95

Lys Asp Leu Gln Met Val Asn Ile Ser Leu Arg Val Leu Ser Arg Pro
            100                 105                 110

Asn Ala Gln Glu Leu Pro Ser Met Tyr Gln Arg Leu Gly Leu Asp Tyr
        115                 120                 125

Glu Glu Arg Val Leu Pro Ser Ile Val Asn Glu Val Leu Lys Ser Val
    130                 135                 140

Val Ala Lys Phe Asn Ala Ser Gln Leu Ile Thr Gln Arg Ala Gln Val
145                 150                 155                 160

Ser Leu Leu Ile Arg Arg Glu Leu Thr Glu Arg Ala Lys Asp Phe Ser
                165                 170                 175

Leu Ile Leu Asp Asp Val Ala Ile Thr Glu Leu Ser Phe Ser Arg Glu
            180                 185                 190

Tyr Thr Ala Ala Val Glu Ala Lys Gln Val Ala Gln Gln Glu Ala Gln
        195                 200                 205

Arg Ala Gln Phe Leu Val Glu Lys Ala Lys Gln Glu Gln Arg Gln Lys
    210                 215                 220

Ile Val Gln Ala Glu Gly Glu Ala Glu Ala Ala Lys Met Leu Gly Glu
225                 230                 235                 240

Ala Leu Ser Lys Asn Pro Gly Tyr Ile Lys Leu Arg Lys Ile Arg Ala
                245                 250                 255

Ala Gln Asn Ile Ser Lys Thr Ile Ala Thr Ser Gln Asn Arg Ile Tyr
            260                 265                 270

Leu Thr Ala Asp Asn Leu Val Leu Asn Leu Gln Asp Glu Ser Phe Thr
        275                 280                 285

Arg Gly Ser Asp Ser Leu Ile Lys Gly Lys Lys
    290                 295
```

<210> SEQ ID NO 33
<211> LENGTH: 20
<212> TYPE: DNA
<213> ORGANISM: Homo sapiens

<400> SEQUENCE: 33
agtgaccgcc gtcaggacga					20

<210> SEQ ID NO 34
<211> LENGTH: 20
<212> TYPE: DNA
<213> ORGANISM: Homo sapiens

<400> SEQUENCE: 34
agtgaccacc gtcaggacga					20

<210> SEQ ID NO 35
<211> LENGTH: 20
<212> TYPE: DNA
<213> ORGANISM: Artificial sequence
<220> FEATURE:
<223> OTHER INFORMATION: Primer

<400> SEQUENCE: 35
cccacctcca tggacgcctt					20

<210> SEQ ID NO 36
<211> LENGTH: 22
<212> TYPE: DNA
<213> ORGANISM: Artificial sequence
<220> FEATURE:
<223> OTHER INFORMATION: Primer

<400> SEQUENCE: 36
gtcagctgtt gtactggcac gc				22

<210> SEQ ID NO 37
<211> LENGTH: 18
<212> TYPE: DNA
<213> ORGANISM: Artificial sequence
<220> FEATURE:
<223> OTHER INFORMATION: Primer

<400> SEQUENCE: 37
ggaaatcgtg cgtgacat					18

<210> SEQ ID NO 38
<211> LENGTH: 23
<212> TYPE: DNA
<213> ORGANISM: Artificial sequence
<220> FEATURE:
<223> OTHER INFORMATION: Primer

<400> SEQUENCE: 38
tcatgatgga gttgaatgta gtt				23

<210> SEQ ID NO 39
<211> LENGTH: 20
<212> TYPE: DNA
<213> ORGANISM: Artificial sequence
<220> FEATURE:
<223> OTHER INFORMATION: Primer

<400> SEQUENCE: 39
gcccagaact tgaaggactt					20

<210> SEQ ID NO 40
<211> LENGTH: 20
<212> TYPE: DNA

```
<213> ORGANISM: Artificial sequence
<220> FEATURE:
<223> OTHER INFORMATION: Primer

<400> SEQUENCE: 40
tcttgctcag tgcttctcca                                               20

<210> SEQ ID NO 41
<211> LENGTH: 20
<212> TYPE: DNA
<213> ORGANISM: Artificial sequence
<220> FEATURE:
<223> OTHER INFORMATION: Primer

<400> SEQUENCE: 41
agtatgtgtg gttggggaat                                               20

<210> SEQ ID NO 42
<211> LENGTH: 20
<212> TYPE: DNA
<213> ORGANISM: Artificial sequence
<220> FEATURE:
<223> OTHER INFORMATION: Primer

<400> SEQUENCE: 42
gctcgctctg taaggtcgtc                                               20

<210> SEQ ID NO 43
<211> LENGTH: 18
<212> TYPE: DNA
<213> ORGANISM: Artificial sequence
<220> FEATURE:
<223> OTHER INFORMATION: Primer

<400> SEQUENCE: 43
aaagagccgg atcgcagg                                                 18

<210> SEQ ID NO 44
<211> LENGTH: 21
<212> TYPE: DNA
<213> ORGANISM: Artificial sequence
<220> FEATURE:
<223> OTHER INFORMATION: Primer

<400> SEQUENCE: 44
caccattgat gttgagaggg c                                             21

<210> SEQ ID NO 45
<211> LENGTH: 20
<212> TYPE: DNA
<213> ORGANISM: Artificial sequence
<220> FEATURE:
<223> OTHER INFORMATION: Primer

<400> SEQUENCE: 45
ctgtttgctc aagacgctga                                               20

<210> SEQ ID NO 46
<211> LENGTH: 20
<212> TYPE: DNA
<213> ORGANISM: Artificial sequence
<220> FEATURE:
<223> OTHER INFORMATION: Primer

<400> SEQUENCE: 46
ctcggcctca caaagaaac                                                20
```

<210> SEQ ID NO 47
<211> LENGTH: 20
<212> TYPE: DNA
<213> ORGANISM: Artificial sequence
<220> FEATURE:
<223> OTHER INFORMATION: Primer

<400> SEQUENCE: 47
tgtctgcatt caggctgttc                                               20

<210> SEQ ID NO 48
<211> LENGTH: 20
<212> TYPE: DNA
<213> ORGANISM: Artificial sequence
<220> FEATURE:
<223> OTHER INFORMATION: Primer

<400> SEQUENCE: 48
gattccctcc tcgagtcctt                                               20

<210> SEQ ID NO 49
<211> LENGTH: 20
<212> TYPE: DNA
<213> ORGANISM: Artificial sequence
<220> FEATURE:
<223> OTHER INFORMATION: Primer

<400> SEQUENCE: 49
caagtgagct ggatgctgaa                                               20

<210> SEQ ID NO 50
<211> LENGTH: 20
<212> TYPE: DNA
<213> ORGANISM: Artificial sequence
<220> FEATURE:
<223> OTHER INFORMATION: Primer

<400> SEQUENCE: 50
agggagtgtc ccttcacaga                                               20

<210> SEQ ID NO 51
<211> LENGTH: 20
<212> TYPE: DNA
<213> ORGANISM: Artificial sequence
<220> FEATURE:
<223> OTHER INFORMATION: Primer

<400> SEQUENCE: 51
gctcagccat tctcaggaac                                               20

<210> SEQ ID NO 52
<211> LENGTH: 20
<212> TYPE: DNA
<213> ORGANISM: Artificial sequence
<220> FEATURE:
<223> OTHER INFORMATION: Primer

<400> SEQUENCE: 52
gccattgtcc cagtcaagat                                               20

<210> SEQ ID NO 53
<211> LENGTH: 20
<212> TYPE: DNA
<213> ORGANISM: Artificial sequence
<220> FEATURE:

<223> OTHER INFORMATION: Primer

<400> SEQUENCE: 53
tcgcgtcaag agggtatttt                                          20

<210> SEQ ID NO 54
<211> LENGTH: 20
<212> TYPE: DNA
<213> ORGANISM: Artificial sequence
<220> FEATURE:
<223> OTHER INFORMATION: Primer

<400> SEQUENCE: 54
taggacccat ggctctaccc                                          20

<210> SEQ ID NO 55
<211> LENGTH: 20
<212> TYPE: DNA
<213> ORGANISM: Artificial sequence
<220> FEATURE:
<223> OTHER INFORMATION: Primer

<400> SEQUENCE: 55
cacgagtcag gtgggaaact                                          20

<210> SEQ ID NO 56
<211> LENGTH: 20
<212> TYPE: DNA
<213> ORGANISM: Artificial sequence
<220> FEATURE:
<223> OTHER INFORMATION: Primer

<400> SEQUENCE: 56
gacgtctgct gcttttctgc                                          20

<210> SEQ ID NO 57
<211> LENGTH: 19
<212> TYPE: DNA
<213> ORGANISM: Artificial sequence
<220> FEATURE:
<223> OTHER INFORMATION: Primer

<400> SEQUENCE: 57
aggcacggac tagcaggac                                           19

<210> SEQ ID NO 58
<211> LENGTH: 18
<212> TYPE: DNA
<213> ORGANISM: Artificial sequence
<220> FEATURE:
<223> OTHER INFORMATION: Primer

<400> SEQUENCE: 58
atgcggacga agccagag                                            18

<210> SEQ ID NO 59
<211> LENGTH: 20
<212> TYPE: DNA
<213> ORGANISM: Artificial sequence
<220> FEATURE:
<223> OTHER INFORMATION: Primer

<400> SEQUENCE: 59
ttagcattca gcccctctgt                                          20

```
<210> SEQ ID NO 60
<211> LENGTH: 21
<212> TYPE: DNA
<213> ORGANISM: Artificial sequence
<220> FEATURE:
<223> OTHER INFORMATION: Primer

<400> SEQUENCE: 60
ttcatgagat gcagtcagca g                                        21

<210> SEQ ID NO 61
<211> LENGTH: 20
<212> TYPE: DNA
<213> ORGANISM: Artificial sequence
<220> FEATURE:
<223> OTHER INFORMATION: Primer

<400> SEQUENCE: 61
acaactggta ggggcaacag                                          20

<210> SEQ ID NO 62
<211> LENGTH: 20
<212> TYPE: DNA
<213> ORGANISM: Artificial sequence
<220> FEATURE:
<223> OTHER INFORMATION: Primer

<400> SEQUENCE: 62
tgtgtggctt tggcaaataa                                          20

<210> SEQ ID NO 63
<211> LENGTH: 20
<212> TYPE: DNA
<213> ORGANISM: Artificial sequence
<220> FEATURE:
<223> OTHER INFORMATION: Primer

<400> SEQUENCE: 63
gcactgtgct ccaactgtgt                                          20

<210> SEQ ID NO 64
<211> LENGTH: 20
<212> TYPE: DNA
<213> ORGANISM: Artificial sequence
<220> FEATURE:
<223> OTHER INFORMATION: Primer

<400> SEQUENCE: 64
gggggagtgt tcttttcctt                                          20

<210> SEQ ID NO 65
<211> LENGTH: 30
<212> TYPE: DNA
<213> ORGANISM: Artificial sequence
<220> FEATURE:
<223> OTHER INFORMATION: Probe

<400> SEQUENCE: 65
ctgtgcctca ctggcggcag tcctgctcaa                               30

<210> SEQ ID NO 66
<211> LENGTH: 30
<212> TYPE: DNA
<213> ORGANISM: Artificial sequence
<220> FEATURE:
<223> OTHER INFORMATION: Probe
```

```
<400> SEQUENCE: 66
ctgtgcctca ctggtggcag tcctgctcaa                                              30

<210> SEQ ID NO 67
<211> LENGTH: 20
<212> TYPE: DNA
<213> ORGANISM: Artificial sequence
<220> FEATURE:
<223> OTHER INFORMATION: Primer

<400> SEQUENCE: 67
ccacctacct ctttctgcct                                                         20

<210> SEQ ID NO 68
<211> LENGTH: 14
<212> TYPE: PRT
<213> ORGANISM: Homo sapiens

<400> SEQUENCE: 68

Ile Thr Tyr Leu Pro Ala Gly Gln Ser Val Leu Leu Gln Leu
1               5                   10

<210> SEQ ID NO 69
<211> LENGTH: 15
<212> TYPE: PRT
<213> ORGANISM: Homo sapiens

<400> SEQUENCE: 69

Arg Ala Arg Phe Val Val Glu Lys Ala Glu Gln Gln Lys Lys Ala
1               5                   10                  15

<210> SEQ ID NO 70
<211> LENGTH: 15
<212> TYPE: PRT
<213> ORGANISM: Homo sapiens

<400> SEQUENCE: 70

Asp Gly Leu Ile Glu Leu Arg Lys Leu Glu Ala Ala Glu Asp Ile
1               5                   10                  15
```

METHODS FOR DIAGNOSING OSTEOARTHRITIS

CROSS REFERENCE TO RELATED APPLICATIONS

This application is a continuation of U.S. patent application Ser. No. 14/568,444 which is a continuation of U.S. patent application Ser. No. 12/447,152, which is a National Entry Application of PCT Application Serial No. PCT/CA2007/001901 filed on Oct. 25, 2007 and published in English under PCT Article 21(2), which itself claims priority on U.S. Provisional Application Ser. No. 60/854,077 filed on 25 Oct. 2006. All documents above are incorporated herein in their entirety by reference.

FIELD OF THE INVENTION

The present invention relates to methods and compositions of prognosing osteoarthritis, methods of selecting compounds and kits therefore.

REFERENCE TO SEQUENCE LISTING

Pursuant to 37 C.F.R. 1.821(c), a sequence listing is submitted herewith as an ASCII compliant text file named 12810_584_ST25, that was created on May 18, 2016 and having a size of 34 kilobytes. The content of the aforementioned file is hereby incorporated by reference in its entirety.

BACKGROUND OF THE INVENTION

The etiology of (OA), the most common form of arthritis, remains unclear notwithstanding the multiplicity of factors that have been considered in primary OA (1, 2). At present, it has become increasingly evident that the majority of OA genetic susceptibility loci cannot be attributed only to structural genes or genes regulating bone mass (3-5). These studies have also highlighted the great heterogeneity and differences in the degree of OA heritability between different joint sites (e.g. hand versus knee) and gender. This is also reflected by the multiplicity of loci identified in OA linkage studies and their discrepancies. Moreover, the functional importance of these susceptibility loci has yet to be confirmed and illustrates our incomplete knowledge of the biology of OA.

Pitx1 (previously called Ptx1) is a homeodomain transcription factor detected initially throughout pituitary development. The Pitx-family contains three related members, Pitx1, Pitx2 and Pitx3, which are members of the paired class of homeodomain proteins. The three Pitx factors have similar transcription properties (6-8). The pitx1 gene is highly expressed in mouse hind limb long bones during development (5) and accumulation of high levels of Pitx1 proteins were detected by immunohistochemistry on hind limb long bone sections mainly in the periarticular region, along the perichondrium (including at the hip and knee joints) and also in the nuclei of proliferative chondrocytes (8). Pitx1 expression was also detected in craniofacial structures such as the mandible and at the temporo-mandibular joints. Mice that are homozygous for the pitx1 deletion are born with the expected Mendelian ratio, but they die soon after birth and phenotypic analysis of pitx1 mutant newborn mice shows striking craniofacial and hind limb skeletal abnormalities (9). Interestingly, heterozygous mice harboring only one mutated allele were phenotypically normal at birth, but a majority of aging pitx1+/± heterozygous mice exhibited gradual degenerative changes of knee joints, showing OA-like lesions at seven months of age. Comparison of histological analysis performed on seven-month old wild-type (FIG. 1A) and pitx1+/− mouse (FIG. 1B) femurs further confirmed an abnormal thickening of the subchondral, trabecular and cortical bone, a feature commonly found in OA. At higher magnification, histological sections stained with the Goldner method revealed a fibrillation and a marked calcification affecting only the articular cartilage of pitx1 heterozygous mice (FIG. 1D). These abnormalities were reminiscent of clinical changes usually observed in OA patients.

The prohibitins, prohibitin (also known as PHB-1 or BAP32) and prohibitone (also known as PHB-2, B-cell receptor associated protein or BAP37, REA for Repressor of estrogen receptor) are highly conserved proteins in eukaryotic cells that are present in multiple cellular compartments (30-32). PHB-1 is localized to the mitochondria where it might have a role in the maintenance of mitochondrial function as well as in the nucleus where it facilitates cellular senescence by recruiting specific co-repressors to inhibit E2F target genes (19-21). The role of PHB-1 in cell-cycle regulation is also demonstrated by its physical interaction with the retinoblastoma tumor-suppressor protein families (22, 23) and through a direct interaction with the highly conserved marked box region of E2Fs (24) preventing E2Fs interaction with their cognate sequence. Nonetheless, the function of PHB-1 in the nucleus is still controversial although its nuclear localization has been found in a variety of cell lines (24).

To the Applicant's knowledge, there is no molecular test for assessment of the risk of progression and severity of OA.

The present description refers to a number of documents, the content of which is herein incorporated by reference in their entirety.

SUMMARY OF THE INVENTION

In accordance with an aspect of the present invention, there is provided a method of selecting a compound, said method comprising the steps of (a) contacting a test compound with at least one cell having a mutation within the E2F-like site of the pitx1 promoter; and (b) determining pitx1 transcription and/or expression level; wherein the test compound is selected if pitx1 transcription and/or expression level is increased in the presence of the test compound as compared to that in the absence thereof. In a specific embodiment, the mutation is a mutation corresponding to −3727 C→T within the E2F-like site of the pitx1 promoter. In another specific embodiment, the selected compound is potentially useful in the treatment of primary osteoarthritis in a joint where Pitx1 is normally expressed. In another specific embodiment, the joint where Pitx1 is normally expressed is selected from the group consisting of knee joint, hip joint and temporo-mandibular joint. In another specific embodiment, the joint where Pitx1 is normally expressed is knee joint. In another specific embodiment, the joint where Pitx1 is normally expressed is hip joint. In another specific embodiment, the joint where Pitx1 is normally expressed is temporo-mandibular joint.

In accordance with another aspect of the present invention, there is provided a method comprising: (a) providing a DNA sample from a subject; and (b) comparing the binding of a pitx1 repressor protein selected from the group consisting of prohibitin (PHB-1), prohibitone (PHB-2) and B cell lymphoma-6 transcriptional repressor interacting co-repressor (BCoR), to an E2F-like site of the pitx1 promoter in the DNA sample from the subject, with that in a control DNA sample, wherein an increased binding of the pitx1 repressor protein to the E2F-like site of the pitx1 promoter in the subject DNA sample as compared to that in the control DNA sample, is indicative that the subject has or is at risk for developing osteoarthritis. In a specific embodiment, said repressor protein is PHB-1. In another specific embodiment, said repressor protein is PHB-2. In another specific embodiment, said repressor protein is BCoR. In another specific embodiment, said subject was not clinically diagnosed with osteoarthritis.

In accordance with another aspect of the present invention, there is provided an isolated nucleic acid molecule of no more than 300 nucleotides comprising (a) a sequence of at least 20 contiguous nucleotides of AGTTCCATACTC-CCATCTGTGCCTCACTGGCGGCAGTCCTGCT-CAAATACATCCTGGCTCT (SEQ ID NO: 1) including nucleotide at position 31 wherein C is replaced by T; or (b) the complement of the sequence in (a). In a specific embodiment, the sequence in (a) is of at least 30 contiguous nucleotides of AGTTCCATACTCCCATCTGTGCCT-CACTGGCGGCAGTCCTGCTCAAATACATCCTG-GCTCT (SEQ ID NO: 1).

In accordance with another aspect of the present invention, there is provided an array of nucleic acid molecules attached to a solid support, the array comprising an oligonucleotide hybridizable to the nucleic acid molecule of the present invention, under conditions in which the oligonucleotide will not substantially hybridize to a nucleic acid molecule consisting of AGTTCCATACTCCCATCTGTGC-CTCACTGG CGGCAGTCCTGCTCAAATACATCCTGGCTCT (SEQ ID NO: 1) or its complement.

In accordance with another aspect of the present invention, there is provided a single-stranded DNA probe of no more than 300 nucleotides hybridizable under high stringency conditions to (a) a nucleic acid molecule consisting of AGTTCCATACTCCCATCTGTGCCTCACTGG CGGCAGTCCTGCTCAAATACATCCTGGCTCT (SEQ ID NO: 1) including nucleotide at position 31 wherein C is replaced by T; or to (b) the complement of the nucleic acid molecule in (a) but not to or to a lesser extent to a nucleic acid molecule consisting of AGTTCCATACTCCCATCT-GTGCCTCACTGG CGGCAGTCCTGCTCAAATACATCCTGGCTCT (SEQ ID NO: 1) or to its complement. In a specific embodiment, the probe is detectably labeled.

In accordance with another aspect of the present invention, there is provided a kit comprising the probe of the present invention and instructions to use the probe to diagnose osteoarthritis in a subject.

In accordance with another aspect of the present invention, there is provided a kit comprising the probe of the present invention and instructions to use the probe to predict whether a subject is at risk of developing osteoarthritis.

In a specific embodiment of the kits of the present invention, the kits further comprise a container for a DNA sample from the subject. In another specific embodiment, the kits further comprise an antibody specific to a pitx1 repressor protein.

In accordance with another aspect of the present invention, there is provided a method comprising: determining the cellular localization of a pitx1 repressor protein selected from the group consisting of prohibitin (PHB-1) and prohibitone (PHB-2) in a subject cell sample selected from the group consisting of an articular chondrocytes sample, a growth plate chondrocytes sample, an osteoblasts sample, a skeletal myoblasts sample and a synoviocytes sample. In a specific embodiment, said method further comprises determining whether the repressor protein nuclear concentration is higher in the subject cell sample as compared to that in a control cell sample; wherein a higher repressor protein nuclear concentration in the subject cell sample is indicative that the subject is at risk of developing osteoarthritis.

In accordance with another aspect of the present invention, there is provided a method comprising: (a) identifying a subject suspected of having osteoarthritis (OA); and (b) detecting the blood concentration of a pitx1 repressor protein in a blood sample of the subject.

In accordance with another aspect of the present invention, there is provided a method comprising: (a) identifying a subject suspected of having osteoarthritis (OA); and (b) detecting the synovial fluid concentration of a pitx1 repressor protein in a synovial fluid sample of the subject.

In a specific embodiment of the methods, the osteoarthritis is selected from the group consisting of knee joint arthritis, hip joint arthritis and temporo-mandibular joints arthritis. In another specific embodiment, the osteoarthritis is knee joint arthritis. In another specific embodiment, the osteoarthritis is hip joint arthritis.

In accordance with another aspect of the present invention, there is provided a method of selecting a compound, said method comprising (a) contacting a test compound with a cell sample selected from the group consisting of an articular chondrocytes sample, a growth plate chondrocytes sample, an osteoblasts sample, a skeletal myoblasts sample and a synoviocytes sample; and (b) determining a pitx1 repressor protein nuclear localization in the cell sample; wherein the test compound is selected if the pitx1 repressor protein nuclear localization in the cell sample is decreased in the presence of the candidate compound as compared to in the absence thereof. In a specific embodiment, the selected test compound is potentially useful in preventing accumulation or retention of a pitx1 repressor protein in cell nuclei or in promoting a pitx1 repressor protein nuclear export. In another specific embodiment, the selected test compound is potentially useful in the treatment of primary osteoarthritis. In another specific embodiment, the pitx1 repressor protein is PHB-1. In another specific embodiment, the pitx1 repressor protein is PHB-2. In another specific embodiment, the pitx1 repressor protein is BCoR.

In accordance with another aspect of the present invention, there is provided a method of selecting a compound, said method comprising the steps of (a) contacting a test compound with a cell sample selected from the group consisting of an articular chondrocytes sample, a growth plate chondrocytes sample, an osteoblasts sample, a skeletal myoblasts sample and a synoviocytes sample; and (b) measuring the binding of a pitx1 repressor protein or complex on pitx1's E2F-like site in the cell sample, wherein the test compound is selected if the binding of the pitx1 repressor protein or complex on pitx1's E2F-like site in the cell sample is decreased in the presence of the test compound as compared to in the absence thereof. In a specific embodiment, the selected test compound is potentially useful in the treatment of primary osteoarthritis. In another specific embodiment, the pitx1 repressor protein or complex comprises PHB-1. In another specific embodiment, the pitx1 repressor protein or complex comprises PHB-2. In another specific embodiment, the pitx1 repressor protein or complex comprises BCoR. In another specific embodiment, said cell sample is from a subject having osteoarthritis. In another specific embodiment, said cell sample is an articular chondrocytes sample. In another specific embodiment, said articular chondrocytes sample is from a subject having osteoarthritis in a knee joint.

In accordance with another aspect of the present invention, there is provided a method of identifying a mutation contributing to osteoarthritis, comprising comparing the nucleotide sequence of a gene selected from the group consisting of PHB-1 gene and PHB-2 gene, or of any gene encoding a protein causing the nuclear accumulation or retention of PHB-1 or PHB-2 in articular chondrocytes of a subject having osteoarthritis with that of the corresponding gene in a control subject. In a specific embodiment, said gene is the PHB-1 gene. In another specific embodiment, said gene is the PHB-2 gene. In another specific embodiment, said mutation is one affecting PHB-1 or PHB-2 DNA-binding and/or its cellular localization.

In accordance with another aspect of the present invention, there is provided a method for diagnosing osteoarthritis comprising detecting in a subject the presence of a mutation directly or indirectly causing the nuclear accumulation or retention of PHB-1 or PHB-2 in cells where PHB-1, PHB-2 or Pitx1 is normally expressed, wherein the presence of the mutation is an indication that the subject has or is at risk of developing osteoarthritis. In a specific embodiment, said method comprises detecting a mutation in CRM-1.

In accordance with another aspect of the present invention, there is provided a method for diagnosing osteoarthritis comprising detecting in a subject, the presence of at least one post-translational modification directly or indirectly causing the nuclear accumulation or retention of PHB-1 or PHB-2 in cells where PHB-1, PHB-2 or Pitx1 is normally expressed, wherein the presence of the at least one post-translational modification is an indication that the subject has osteoarthritis.

In accordance with another aspect of the present invention, there is provided a kit comprising an antibody specific to PHB-1 or to PHB-2 and an antibody specific to BCoR. In a specific embodiment, the kit further comprises instructions to use the antibodies to predicting whether a subject is at risk for developing osteoarthritis.

In accordance with another aspect of the present invention, there is provided a purified repressor complex comprising BCoR and at least one of PHB-1 and PHB-2. In a specific embodiment, the repressor complex comprises BCoR and PHB-1. In another specific embodiment, the repressor complex comprises BCoR and PHB-2. In another specific embodiment, the repressor complex comprises BCoR, PHB-1 and PHB-2.

In accordance with another aspect of the present invention, there is provided a method of using the repressor complex of the purified repressor complex of the instant disclosure, for binding to a E2F-site. In a specific embodiment, the E2F-site is that of pitx1 promoter.

In accordance with another aspect of the present invention, there is provided a method comprising: determining the cellular localization of a pitx1 repressor protein or complex selected from the group consisting of prohibitin (PHB-1), prohibitone (PHB-2), B cell lymphoma-6 transcriptional repressor interacting co-repressor (BCoR), PHB-1-containing complex, PHB-2-containing complex and BCoR-containing complex, in a subject cell sample selected from the group consisting of an articular chondrocytes sample, a growth plate chondrocytes sample, an osteoblasts sample, a skeletal myoblasts sample and a synoviocytes sample.

In a specific embodiment, the method further comprises determining whether the repressor protein or complex nuclear concentration is higher in the subject cell sample as compared to that in a control cell sample; wherein a higher repressor protein or complex nuclear concentration in the subject cell sample is indicative that the subject is at risk of developing osteoarthritis.

In accordance with another aspect of the present invention, there is provided a method comprising: (a) identifying a subject suspected of having osteoarthritis (OA); and (b) detecting the blood concentration of a pitx1 repressor protein or complex in a blood sample of the subject.

In accordance with another aspect of the present invention, there is provided a method comprising: (a) identifying a subject suspected of having osteoarthritis (OA); and (b) detecting the synovial fluid concentration of a pitx1 repressor protein or complex in a synovial fluid sample of the subject.

In a specific embodiment, the osteoarthritis is selected from the group consisting of knee joint arthritis, hip joint arthritis and temporo-mandibular joints arthritis. In another specific embodiment, the osteoarthritis is knee joint arthritis. In another specific embodiment, the osteoarthritis is hip joint arthritis.

In accordance with another aspect of the present invention, there is provided a method of selecting a compound, said method comprising (a) contacting a test compound with a cell sample selected from the group consisting of an articular chondrocytes sample, a growth plate chondrocytes sample, an osteoblasts sample, a skeletal myoblasts sample and a synoviocytes sample; and (b) determining a pitx1 repressor protein or complex nuclear localization in the cell sample; wherein the test compound is selected if the pitx1 repressor protein or complex nuclear localization in the cell sample is decreased in the presence of the candidate compound as compared to in the absence thereof.

In accordance with another aspect of the present invention, there is provided a method of selecting a compound, said method comprising (a) contacting a test compound with a cell sample selected from the group consisting of an articular chondrocytes sample, a growth plate chondrocytes sample, an osteoblasts sample, a skeletal myoblasts sample and a synoviocytes sample; and (b) assessing the sumoylation of a pitx1 repressor protein or complex in the cell sample; wherein the test compound is selected if the sumoylation of the pitx1 repressor protein or complex in the cell sample is increased in the presence of the candidate compound as compared to in the absence thereof.

In a specific embodiment, the selected test compound is potentially useful in preventing accumulation or retention of the pitx1 repressor protein or complex in cell nuclei or in promoting the pitx1 repressor protein or complex nuclear export.

In accordance with another aspect of the present invention, there is provided a method of selecting a compound, said method comprising the steps of (a) contacting a test compound with a cell sample selected from the group consisting of an articular chondrocytes sample, a growth plate chondrocytes sample, an osteoblasts sample, a skeletal myoblasts sample and a synoviocytes sample; and (b) measuring the binding of a pitx1 repressor protein or complex on pitx1's E2F-like site in the cell sample, wherein the test compound is selected if the binding of the pitx1 repressor protein or complex on pitx1's E2F-like site in the cell sample is decreased in the presence of the test compound as compared to in the absence thereof.

In a specific embodiment, the selected test compound is potentially useful in the treatment of primary osteoarthritis. In another specific embodiment, the pitx1 repressor protein or complex comprises prohibitin (PHB-1). In another specific embodiment, the pitx1 repressor protein or complex comprises prohibitone (PHB-2). In another specific embodiment, the pitx1 repressor protein or complex comprises B cell lymphoma-6 transcriptional repressor interacting co-repressor (BCoR). In another specific embodiment, the pitx1 repressor protein is prohibitin (PHB-1). In another specific embodiment, the pitx1 repressor protein is prohibitone (PHB-2). In another specific embodiment, the pitx1 repressor protein is B cell lymphoma-6 transcriptional repressor interacting co-repressor (BCoR). In another specific embodiment, said cell sample is from a subject having osteoarthritis. In another specific embodiment, said cell sample is an articular chondrocytes sample. In another specific embodiment, said articular chondrocytes sample is from a subject having osteoarthritis in a knee joint.

In accordance with another aspect of the present invention, there is provided a method of identifying a mutation contributing to osteoarthritis, comprising comparing the nucleotide sequence of a gene selected from the group consisting of prohibitin (PHB-1) gene, prohibitone (PHB-2) gene, B cell lymphoma-6 transcriptional repressor interacting co-repressor (BCoR) gene or of any gene encoding a protein causing the nuclear accumulation or retention of PHB-1, PHB-2 or BCoR in articular chondrocytes of a subject having osteoarthritis with that of the corresponding gene in a control subject.

In a specific embodiment, said gene is the PHB-1 gene. In another specific embodiment, said gene is the PHB-2 gene. In another specific embodiment, said mutation is one affecting PHB-1 or PHB-2 DNA-binding and/or its cellular localization.

In accordance with another aspect of the present invention, there is provided a method for predicting the risk of developing osteoarthritis comprising detecting in a subject the presence of a mutation directly or indirectly causing the nuclear accumulation or retention of prohibitin (PHB-1), prohibitone (PHB-2) or B cell lymphoma-6 transcriptional repressor interacting co-repressor (BCoR) in cells where PHB-1, PHB-2, BCoR or Pitx1 is normally expressed, wherein the presence of the mutation is an indication that the subject has or is at risk of developing osteoarthritis.

In a specific embodiment, said method comprises detecting a mutation in CRM-1.

In accordance with another aspect of the present invention, there is provided a method of identifying a post-translational modification contributing to osteoarthritis, comprising comparing the post-translational modification of a protein selected from the group consisting of prohibitin (PHB-1) and prohibitone (PHB-2), B cell lymphoma-6 transcriptional repressor interacting co-repressor (BCoR) or of any protein causing the nuclear accumulation or retention of PHB-1, PHB-2 or BCoR in articular chondrocytes of a subject having osteoarthritis with that of the corresponding gene in a control subject.

In accordance with another aspect of the present invention, there is provided a method for predicting the risk of developing osteoarthritis comprising detecting in a subject, the presence of at least one post-translational modification directly or indirectly causing the nuclear accumulation or retention of prohibitin (PHB-1), prohibitone (PHB-2) or B cell lymphoma-6 transcriptional repressor interacting co-repressor (BCoR) in cells where PHB-1, PHB-2 or Pitx1 is normally expressed, wherein the presence of the at least one post-translational modification is an indication that the subject has or is at risk of developing osteoarthritis.

In accordance with another aspect of the present invention, there is provided a kit comprising an antibody specific to prohibitin (PHB-1) or to prohibitone (PHB-2) and an antibody specific to B cell lymphoma-6 transcriptional repressor interacting co-repressor (BCoR).

In a specific embodiment, the kit of further comprises instructions to use the antibodies to predict whether a subject is at risk for developing osteoarthritis.

In accordance with another aspect of the present invention, there is provided a purified repressor complex comprising B cell lymphoma-6 transcriptional repressor interacting co-repressor (BCoR) and at least one of prohibitin (PHB-1) and prohibitone (PHB-2).

In a specific embodiment, the repressor complex comprises BCoR and PHB-1. In another specific embodiment, the repressor complex comprises BCoR and PHB-2. In another specific embodiment, the repressor complex comprises BCoR, PHB-1 and PHB-2.

In accordance with another aspect of the present invention, there is provided a method of using the repressor complex of the present invention, for binding to a E2F-site. In a specific embodiment, the E2F-site is that of pitx1 promoter.

The articles "a," "an" and "the" are used herein to refer to one or to more than one (i.e., to at least one) of the grammatical object of the article.

The term "including" and "comprising" are used herein to mean, and re used interchangeably with, the phrases "including but not limited to" and "comprising but not limited to".

The terms "such as" are used herein to mean, and is used interchangeably with, the phrase "such as but not limited to".

As used herein the term "osteoarthritis" refers to a form of arthritis involving the deterioration of the cartilage that cushions the ends of bones within joints. It is also called degenerative arthritis, degenerative joint disease or hypertrophic arthritis. This term includes early onset of osteoarthritis. Worldwide, osteoarthritis is the most common joint disorder. In western countries, radiographic evidence of this disease is present in the majority of persons by 65 years of age and in about 80 percent of persons more than 75 years of age (33). Approximately 11 percent of persons more than 64 years of age have symptomatic osteoarthritis of the knee (34).

As used herein the terms "early onset of osteoarthritis" refer to a form of osteoarthritis that either is first diagnosed at 40 years of age or earlier or that leads to knee joint replacement of the subject before he is 55 years old.

As used herein the terms "risk of developing osteoarthritis" refers to a predisposition of a subject of presenting primary OA symptoms and/or more severe primary OA symptoms at a future time. Similarly, the "risk of developing osteoarthritis in a joint where Pitx1 is normally expressed" refers to a risk for a subject of presenting primary OA symptoms, and/or more severe primary OA symptoms at a future time in a joint where Pitx1 is normally expressed.

As used herein the terms "primary OA" when used to qualify knee/hip joint OA refers to knee/hip joint OA due to a disease or degeneration for instance as opposed to secondary knee/hip joint OA resulting from trauma, joint overuse, obesity, etc.

As used herein the term "subject" is meant to refer to any mammal including human, mice, rat, dog, cat, pig, monkey, horse, etc. In a particular embodiment, it refers to a human. In another particular embodiment, it refers to a horse and more specifically a racing horse.

As used herein the terms "control DNA sample" are meant to refer to a genomic DNA that does not come from a subject known to suffer from osteoarthritis (OA) (control subject). In reference to either cartilage sections or articular chondrocytes obtained from OA versus control subjects, these controls subjects are age-matched individuals unaffected by OA as tested at the time of autopsy or at the time of biopsy when knee joints or hip joints are obtained after a trauma.

As used herein the terms "predisposition for developing a disease or condition" refers to a predisposition of a subject of presenting symptoms of the disease or condition and/or more severe symptoms of the disease or conditions at a future time.

As used herein the terms "control sample" are meant to refer to a sample that does not come from a subject known to suffer from the disease or disorder or from the subject under scrutiny but before the subject had the disease or disorder. In methods of diagnosing a predisposition of a subject to develop a disease or disorder, the sample may also come from the subject under scrutiny at an earlier stage of the disease or disorder.

As used herein the terms "subject DNA sample" are meant to refer to any biological sample from the subject from whom genomic DNA can be extracted, namely any subject tissue or cell type including saliva and blood.

As used herein the terms "cell sample" are meant to refer to a sample containing any type of cell wherein, in a subject affected by OA, PHB-1, PHB-2 and/or BCoR (also known as BCL-6 interacting corepressor, wherein BCL-6 stands for B cell lymphoma-6 transcriptional repressor) pathologically accumulates in the cell nuclei. Without being so limited, it includes articular chondrocytes, growth plate chondrocytes, osteoblasts, skeletal myoblasts and synoviocytes. As used herein the terms "articular chondrocyte" are meant to refer to chondrocytes found in joints.

As used herein the terms "not clinically diagnosed with osteoarthritis" are meant to refer to a subject that was never diagnosed with OA using a clinical method such as an imaging method like X-ray, and magnetic resonance imaging (MRI). In particular, for diagnosing hip OA, a current clinical method recommended by the American College of Rheumatology includes hip pain and at least 2 of the following 3 features: ESR<20 mm/hour; radiographic femoral or acetabular osteophytes; and radiographic joint space narrowing (superior, axial, and/or medial). In particular, for diagnosing knee OA, there are three methods currently recommended by the American College of Rheumatology 1) Clinical and laboratory method: knee pain and at least 5 of the following 9 features: age >50 years, stiffness <30 minutes, crepitus, bony tenderness, bony enlargement, no palpable warmth, ESR <40 mm/hour, RF <1:40; and SF OA; 2) Clinical and radiographic: knee pain, and at least 2 of the following 3 features, Age >50 years; stiffness <30 minutes; crepitus; +osteophytes; and 3) Clinical: knee pain and at least 3 of the following 6 features: age >50 years, stiffness <30 minutes, crepitus, bony tenderness, bony enlargement, no palpable warmth.

As used herein the terminology "purified", "isolated", "purification" or "isolation" in the expressions "purified polypeptide", "isolated polypeptide", "isolated protein", "purified complexes", "isolated complexes" or "tandem affinity purification" means altered "by the hand of man" from its natural state (i.e. if it occurs in nature, it has been changed or removed from its original environment) or it has been synthesized in a non-natural environment (e.g., artificially synthesized). These terms do not require absolute purity (such as a homogeneous preparation) but instead represents an indication that it is relatively more pure than in the natural environment. For example, a protein/peptide naturally present in a living organism is not "purified" or "isolated", but the same protein separated (about 90-95% pure at least) from the coexisting materials of its natural state is "purified" or "isolated" as this term is employed herein.

As used herein, the term "antibody" or refers to an antibody that specifically binds to (interacts with) a protein of the present invention and displays no substantial binding to other naturally occurring proteins other than the ones sharing the same antigenic determinants. The term antibody or immunoglobulin is used in the broadest sense, and covers monoclonal antibodies (including full length monoclonal antibodies), polyclonal antibodies, multispecific antibodies, and antibody fragments so long as they exhibit the desired biological activity. Antibody fragments comprise a portion of a full length antibody, generally an antigen binding or variable region thereof. Examples of antibody fragments include Fab, Fab', F(ab')2, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, VH regions (VH, VH-VH), anticalins, PepBodies™, antibody-T-cell epitope fusions (Troybodies) or Peptibodies. Additionally, any secondary antibodies, either monoclonal or polyclonal, directed to the first antibodies would also be included within the scope of this invention.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody A Laboratory Manual, CSH Laboratories). The term antibody encompasses herein polyclonal, monoclonal antibodies and antibody variants such as single-chain antibodies, humanized antibodies, chimeric antibodies and immunologically active fragments of antibodies (e.g. Fab and Fab' fragments) which inhibit or neutralize their respective interaction domains in Hyphen and/or are specific thereto.

Diagnostic or Prognostic Methods

A method for diagnosing or screening for the presence of a disease or disorder or a predisposition for developing the disease or disorder in a subject, which disease or disorder is characterized by an aberrant amount, activity, protein composition, intracellular localization and/or formation of a complex, comprising the steps of: (1) comparing the amount of, activity of, protein composition of, intracellular localization of, and/or formation of said complex in a sample from the subject with that in a control sample, wherein a difference in said amount, activity, protein composition of, intracellular localization and/or formation of said complex as compared to that in the control sample is indicative that the subject has the disease or disorder or a predisposition for developing the disease or condition.

In a specific embodiment, the control sample is selected from a sample from the subject at an earlier stage of the disease or disorder or before the subject had the disease. In another embodiment, the control sample is from a different subject that does not have the disease or disorder or predisposition to develop the disease or condition.

As used herein the terms "corresponding to" in the expression "a mutation corresponding to −3727 C→T" are meant to reflect the fact that the C→T mutation occurring in the E2F-like site of the human pitx1 promoter may be found in certain subjects at a position that is upstream or downstream from the position −3727. Indeed, because of polymorphism in the pitx1 promoter within the population, the C→T mutation may be at a position other than 3727 nucleotides upstream of the transcription point of pitx1. For instance if, as compared to subjects wherein the C→T mutation occurs at position −3727, a subject has a deletion of one nucleotide between the transcription point of pitx1 and the position where the mutation in the E2F-like site of the human pitx1 promoter occurs, then the position of the mutation will be −3726 in that subject. Similarly as compared to subjects wherein the C→T mutation occurs at position →3727, a subject that possesses an additional nucleotide in the region of interest, the position of the mutation will be →3728 in that subject. The method of the present invention thus encompasses determining whether there is a C→T mutation in the E2F-like site of the pitx1 promoter at a position that corresponds to that found at position −3727 C→T in the subjects tested in the Examples presented herein. Also as used herein, the terms "corresponding to" in the expression "a mutation corresponding to −3727 C→T" is meant to encompass a G→A mutation found in the strand complementary to that containing the −3727 C-T mutation.

Other mutations encompass by the present invention include any other mutation within or adjacent the core binding site of the E2F-like site found in human pitx1 promoter that could prevent the binding of E2Fs or enhance the recruitment and/or stabilization of a repressor complex reducing or abrogating Pitx1 gene expression.

As used herein, the terms "joint where Pitx1 is normally expressed" are meant to refer to, without being so limited, knee joint and hip joint.

The present invention encompasses methods for identifying a mutation corresponding to −3727 C→T within an E2F-like site in one strand of subject pitx1 promoter. Such methods include, without being so limited, Wave nucleic acid fragment analysis (dHPLC) and direct sequencing on PCR fragments amplified from genomic DNA isolated from subjects.

The present invention also relates to methods for the determination of the level of expression of transcripts or translation product of a single gene such as pitx1. The present invention therefore encompasses any known method for such determination including real time PCR and competitive PCR, Northern blots, nuclease protection, plaque hybridization and slot blots.

The present invention also concerns isolated nucleic acid molecules including probes. In specific embodiments, the isolated nucleic acid molecules have no more than 300, or no more than 200, or no more than 100, or no more than 90, or no more than 80, or no more than 70, or no more than 60, or no more than 50, or no more than 40 or no more than 30 nucleotides. In specific embodiments, the isolated nucleic acid molecules have at least 20, or at least 30, or at least 40 nucleotides. In other specific embodiments, the isolated nucleic acid molecules have at least 20 and no more than 300 nucleotides. In other specific embodiments, the isolated nucleic acid molecules have at least 20 and no more than 200 nucleotides. In other specific embodiments, the isolated nucleic acid molecules have at least 20 and no more than 100 nucleotides. In other specific embodiments, the isolated nucleic acid molecules have at least 20 and no more than 90 nucleotides. In other specific embodiments, the isolated nucleic acid molecules have at least 20 and no more than 80 nucleotides. In other specific embodiments, the isolated nucleic acid molecules have at least 20 and no more than 70 nucleotides. In other specific embodiments, the isolated nucleic acid molecules have at least 20 and no more than 60 nucleotides. In other specific embodiments, the isolated nucleic acid molecules have at least 20 and no more than 50 nucleotides. In other specific embodiments, the isolated nucleic acid molecules have at least 20 and no more than 40 nucleotides. In other specific embodiments, the isolated nucleic acid molecules have at least 20 and no more than 30 nucleotides. In other specific embodiments, the isolated nucleic acid molecules have at least 30 and no more than 300 nucleotides. In other specific embodiments, the isolated nucleic acid molecules have at least 30 and no more than 200 nucleotides. In other specific embodiments, the isolated nucleic acid molecules have at least 30 and no more than 100 nucleotides. In other specific embodiments, the isolated nucleic acid molecules have at least 30 and no more than 90 nucleotides. In other specific embodiments, the isolated nucleic acid molecules have at least 30 and no more than 80 nucleotides. In other specific embodiments, the isolated nucleic acid molecules have at least 30 and no more than 70 nucleotides. In other specific embodiments, the isolated nucleic acid molecules have at least 30 and no more than 60 nucleotides. In other specific embodiments, the isolated nucleic acid molecules have at least 30 and no more than 50 nucleotides. In other specific embodiments, the isolated nucleic acid molecules have at least 30 and no more than 40 nucleotides.

Probes of the invention can be utilized with naturally occurring sugar-phosphate backbones as well as modified backbones including phosphorothioates, dithionates, alkyl phosphonates and α-nucleotides and the like. Modified sugar-phosphate backbones are generally known (62,63). Probes of the invention can be constructed of either ribonucleic acid (RNA) or deoxyribonucleic acid (DNA), and preferably of DNA.

The types of detection methods in which probes can be used include Southern blots (DNA detection), dot or slot blots (DNA, RNA), and Northern blots (RNA detection). Although less preferred, labeled proteins could also be used to detect a particular nucleic acid sequence to which it binds. Other detection methods include kits containing probes on a dipstick setup and the like.

As used herein the terms "detectably labeled" refer to a marking of a probe in accordance with the presence invention that will allow the detection of the mutation of the present invention. Although the present invention is not specifically dependent on the use of a label for the detection of a particular nucleic acid sequence, such a label might be beneficial, by increasing the sensitivity of the detection. Furthermore, it enables automation. Probes can be labeled according to numerous well known methods (64). Non-limiting examples of labels include 3H, 14C, 32P, and 35S. Non-limiting examples of detectable markers include ligands, fluorophores, chemiluminescent agents, enzymes, and antibodies. Other detectable markers for use with probes, which can enable an increase in sensitivity of the method of the invention, include biotin and radionucleotides. It will become evident to the person of ordinary skill that the choice of a particular label dictates the manner in which it is bound to the probe.

As commonly known, radioactive nucleotides can be incorporated into probes of the invention by several methods. Non-limiting examples thereof include kinasing the 5' ends of the probes using gamma 32P ATP and polynucleotide kinase, using the Klenow fragment of Pol I of *E. coli* in the presence of radioactive dNTP (e.g. uniformly labeled DNA probe using random oligonucleotide primers in lowmelt gels), using the SP6/T7 system to transcribe a DNA segment in the presence of one or more radioactive NTP, and the like.

The present invention also relates to methods of selecting compounds. As used herein the term "compound" is meant to encompass natural, synthetic or semi-synthetic compounds, including without being so limited chemicals, macromolecules, cell or tissue extracts (from plants or animals), nucleic acid molecules, peptides, antibodies and proteins.

The present invention also relates to arrays. As used herein, an "array" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports.

As used herein "array of nucleic acid molecules" is an intentionally created collection of nucleic acids which can be prepared either synthetically or biosynthetically in a variety of different formats (e.g., libraries of soluble molecules; and libraries of oligonucleotides tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleotide sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

As used herein "solid support", "support", and "substrate" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations.

Any known nucleic acid arrays can be used in accordance with the present invention. For instance, such arrays include those based on short or longer oligonucleotide probes as well as cDNAs or polymerase chain reaction (PCR) products (52). Other methods include serial analysis of gene expression (SAGE), differential display, (53) as well as subtractive hybridization methods (54), differential screening (DS), RNA arbitrarily primer (RAP)-PCR, restriction endonucleolytic analysis of differentially expressed sequences (READS), amplified restriction fragment-length polymorphisms (AFLP).

"Stringent hybridization conditions" and "stringent hybridization wash conditions" in the context of nucleic acid hybridization experiments such as Southern and Northern hybridization are sequence dependent, and are different under different environmental parameters. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, 1984; $T_m$ 81.5° C.+16.6 (log M) +0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point I for the specific sequence and its complement at a defined ionic strength and pH. However, severely stringent conditions can utilize a hybridization and/or wash at 1, 2, 3, or 4° C. lower than the thermal melting point I; moderately stringent conditions can utilize a hybridization and/or wash at 6, 7, 8, 9, or 10° C. lower than the thermal melting point I; low stringency conditions can utilize a hybridization and/or wash at 11, 12, 13, 14, 15, or 20° C. lower than the thermal melting point I. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, 1993. Generally, highly stringent hybridization and wash conditions are selected to be about 5° C. lower than the thermal melting point $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see 64 for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long robes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

Washing with a solution containing tetramethylammonium chloride (TeMAC) could allow the detection of a single mismatch using oligonucleotide hybridyzation since such mismatch could generate a 10° C. difference in the annealing temperature. The formulation to determine the washing temperature is Tm (° C.)=]−682 ($L^{-1}$)+97 where L represents the length of the oligonucleotide that will be used for the hybridization. When the oligonucleotide of the present invention has a length of 20 nucleotides: 5'-TCACTGG$\underline{T}$GGCAGTCCTGCT-3' (SEQ ID NO: 2), underscore indicating the mutation, the hybridization is performed 5° C. below the Tm which is calculated using the formula above at 62.9° C. In principle, a single mismatch will generate a 10° C. drop in the annealing so that a temperature of 57° C. should only detect mutants harbouring the T mutation. Such conditions are high stringency conditions appropriate to identify a single nucleotide mutation in the 20 nucleotides probes of the present invention (56).

As used herein the terms "repressor protein" when used in relation to the E2F-like site of the pitx1 promoter region refer to any protein that alone and/or in combination with other proteins lowers or represses expression of Pitx1. Without being so limited, they include BCoR, PHB-1, PHB-2, combination thereof and any interacting partner of PHB-1, PHB-2 and/or BCoR including those disclosed in Table 1 above. As used herein the term "BCoR repressing activity on pitx1" or "PHB-1 repressing activity on pitx1" or "PHB-2 repressing activity on pitx1" is thus meant to refer to the activity of any of these proteins leading to decreased expression of Pitx1.

As used herein the terms "repressor complex" when used in relation to the E2F-like site of the pitx1 promoter region refers to a combination of repressor proteins that lowers or represses expression of Pitx1.

The present invention also encompasses arrays to detect and/or quantify the nuclear localization of proteins including PHB-1, PHB-2 and/or BCoR. Such arrays include protein micro- or macroarrays, gel technologies including high-resolution 2D-gel methodologies, possibly coupled with mass spectrometry (55), imaging system at the cellular level such as microscopy combined with a fluorescent labeling system.

The present invention also includes the use of tissue biopsy to determine the nuclear accumulation of PHB-1, PHB-2 and BCoR within articular chondrocytes, growth plate chondrocytes, osteoblasts, skeletal myoblasts and synoviocytes. For instance, cartilage biopsy could be performed during arthroscopy procedure to assess OA or its progression by immunofluorescence microscopy to determine the nuclear localization of PHB-1, PHB-2 and/or BCoR. This method could be useful for instance when arthroscopy procedure is required to establish a clinical diagnostic. Alternatively, a muscle biopsy in lower limbs could be used to test whether or not PHB-1 and/or PHB-2 are accumulated in the nuclei of myoblasts. This method would advantageously be less invasive than a regular arthroscopy. The determination of the cellular localization or concentration of a pitx1 repressor protein is typically performed either by a) preparing a nuclear extract of a subject sample and determining concentration of a pitx1 repressor protein; or by (b) determining the localization of the pitx1 repressor protein by immunohistochemistry.

In accordance with the present invention, an increased pitx1 repressor protein nuclear localization in a subject may be the sign of an increased binding/affinity of the repressor protein to the pitx1's E2F-like site, of an increased nuclear entry/import of the repressor protein or a decreased nuclear export of the repressor protein. The present invention also relates to methods of selecting a compound. Hence, a compound tested with specific embodiments of methods of selecting compounds of the present invention that results in a decreased pitx1 repressor protein nuclear localization may be a compound that decreases binding/affinity of the repressor protein to the pitx1's E2F-like site, that decreases nuclear entry/import of the repressor protein or that increases nuclear export of the repressor protein.

The present invention also encompasses methods for identifying specific mutation(s) directly or indirectly affecting the function of PHB-1 and/or PHB-2. Without being so limited, mutations of interest include any mutation affecting the transport of these proteins outside the nucleus, or modifying the interactions between PHB-1 and/or PHB-2.

As used herein, the terms "mutation directly or indirectly causing the nuclear accumulation or retention of PHB-1, PHB-2 or BcoR in cells where PHB-1, PHB-2, BCoR or Pitx1 is normally expressed" are meant to refer to, without being so limited, a mutation within the NES (nuclear export sequences) of PHB-1, PHB-2 or BCoR; a mutation modulating the formation of homomeric and heteromeric complexes between PHB-1, BCoR and/or PHB-2 resulting in the masking of their respective NES or reducing their accessibility to exportin-1 (also know as CRM-1); a mutation affecting the expression and/or function of exportin-1; a mutation affecting the formation of a ternary complex with CRM-1/exportin 1 and GTP-bound form of Ran in the nucleus; a mutation affecting TGF-β signaling including a mutation affecting binding of TGF-β with asporin, a cartilage extracellular protein elevated in OA cartilage; a mutation affecting the PHB-1 or PHB-2 recruitment of Brg-1/Brm to E2F-responsive promoters; a mutation affecting JNK1's ability to promote PHB-1's association with Brg-1 or Brn on E2F-responsive promoters; a mutation affecting Akt's binding to PHB-1-PHB-2 or Akt's ability to enter the nucleus. It also refers to any mutations in molecules interacting with PHB-1, BCoR and/or PHB-2, which could prevent the nuclear export of PHB-1 and/or PHB-2. The list of known interacting partners of PHB-1 and PHB-2 is indicated in Table 1 but it is not limited to the molecules indicated in this Table 1.

TABLE 1

LIST OF PROTEINS INTERACTING WITH PHB-1 AND/OR PHB-2

| PHB-1 | PHB-2 |
|---|---|
| AR(37) | Akt (38) |
| Brg-1 (39) | ER (40) |
| Brm(39) | HDAC1(41) |
| CRM-1(42) | HDAC5(41) |
| E2F1(43) | NR2F1 (41) |
| ER (44) | NR2F2 (41) |
| HDAC1 (45) | PHB-1 (46) |
| HP1 (47) | |
| JNK1(47) | |
| MLK2(48) | |
| N-CoR (45) | |
| p53(49) | |
| PHB-2 (46) | |
| Raf (50) | |
| Rb (51) | |

As used herein the terms "post-translational modification directly or indirectly causing the nuclear accumulation or retention of PHB-1, PHB-2 or BCoR in cells where PHB-1, PHB-2, BCoR or Pitx1 is normally expressed" includes, without being so limited, a post-translational modification including phosphorylation with kinases such as JNK1, tyrosine kinases such as MTOR, PAK, EGFR and/or JAK, ubiquitinylation or sumoylation modulating the formation of homomeric and heteromeric complexes between PHB-1, PHB-2 and/or BCoR resulting in the masking of their respective NES or reducing their accessibility to exportin-1.

The present invention relates to a kit for diagnosing OA and/or predicting whether a subject is at risk of developing OA comprising an isolated nucleic acid, a protein or a ligand such as an antibody in accordance with the present invention. For example, a compartmentalized kit in accordance with the present invention includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the subject sample (DNA genomic nucleic acid, cell sample or blood samples), a container which contains in some kits of the present invention, the probes used in the methods of the present invention, containers which contain enzymes, containers which contain wash reagents, and containers which contain the reagents used to detect the extension products. The present invention also relates to a kit comprising the antibodies which are specific to pitx1 repressors. Kits of the present invention may also contain instructions to use these probes and or antibodies to diagnose OA or predict whether a subject is at risk of developing OA.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 1B is ×5 and FIG. 1C and FIG. 1D) is ×20;

(FIG. 1A) Reverse transcription-polymerase chain reaction for pitx1 gene expression in human articular chondrocytes derived from knee cartilage of control subjects (N, n=4) and patients with osteoarthritis (OA, n=7). Pitx1 specific mRNA transcripts were detected in all control tissues (N1-N4). Loss of the pitx1 gene expression was observed in all examined OA samples (OA1-OA7) and β-actin expression was used as internal control. Immunodetection of Pitx1 proteins in human control (FIG. 1B) and OA (FIG. 1C) cartilage tissues was performed using a specific antibody against human Pitx1 protein. In control cartilage sections (n=8), specific immunoreactivity was demonstrated by intense brown staining in nucleus of chondrocytes of the superficial and deep zones (arrow). In OA cartilage (n=8), only a few cells stained specifically for Pitx1. These were located mainly in the superficial layer (arrow). The specificity of staining was evaluated by omission of the primary antibody and by substitution of the primary antibody with non-immune IgG (Nordic Immunology, Tilburg, The Netherlands) following the same experimental protocol. No staining was observed. (Original magnification ×20). (FIG. 1D) Cell scores for Pitx1-positive chondrocytes, indicating significant differences between OA and normal (control) cartilage and between the deep zones for each cartilage type, by Mann-Whitney U test. Values are the mean+SEM of 8 normal and 8 OA specimens;

FIG. 3 shows an alignment of the human pitx1 E2F-like DNA-binding site with known E2F sites found in mammalian cell cycle regulation promoters. Alignment of different E2F binding sites (E2F core) and conserved adjacent cyclin homology region (CHR) found in promoter of genes involved in the regulation of cell cycle. The presented E2F sites are DNA Polα (SEQ ID NO: 3); p107 (SEQ ID NO: 4); Cdc2 (SEQ ID NO: 5); Adeno E2a (SEQ ID NO: 6); E2F-1 (SEQ ID NO: 7); H2A (SEQ ID NO: 8); DHFR (SEQ ID NO: 9); HsOrc1 (SEQ ID NO: 10); c-Myc (SEQ ID NO: 11); CycA (SEQ ID NO: 12); Cdc25 (SEQ ID NO: 13); TK (SEQ ID NO: 14); B-Myb (SEQ ID NO: 15); Hpitx1 (SEQ ID NO: 16). Positions are indicated and numbered in function of the transcriptional start site while Act and Rep indicate an activating and a repressing site respectively. Note that E2F element found in human pitx1 promoter is more distal than usual cell cycle genes;

FIGS. 4A-D show an electrophoretic mobility shift assay (EMSA) of nuclear extracts prepared with OA articular chondrocytes. Representative EMSA using the wild type probe (FIG. 4A) or the mutant probe (FIG. 4B). Note that attempts to supershift the bound complexes were performed with different antibodies and addition of anti-BCoR antibodies disrupted partially the main complex and generated an additional band suggesting the presence of BCoR in the bound complex. (FIG. 4C) Representative off-rate autoradiograph showing the effect of addition of unlabeled double-stranded oligonucleotide corresponding to E2F-like site found in human pitx1 promoter as a competitor on the E2F complex binding to radiolabeled wild-type E2F site (wild-type probe) versus mutant E2F site found in OA patients (mutant probe). Competitor double-stranded oligonucleotide (70-fold molar excess) was added (t=0), and aliquots of gel mobility shift reaction mixtures were removed at the indicated times after the addition. (FIG. 4D) The dissociation rate of wild-type E2F and the mutant (OA) site were compared by directly counting the radioactivity of each bound E2F complex by cutting the corresponding bands on the dried gel. The half-life of binding for off-rate experiments was computed by plotting the disappearance of 50% when compared to the initial binding of E2F complex. The graph depicts the average half-life value for the E2F complex;

(FIG. 5A) Co-immunoprecipitation were performed with anti-PHB-1, anti-PHB-2 (as internal control) and anti-E2F1 in OA and normal nuclear extracts obtained from primary human articular chondrocytes cultures. Western blot performed with anti-PHB-2 shows that PHB-2 interacts physically with PHB-1 and E2F1 only in OA nuclear extracts. (FIG. 5B) Chromatin immunoprecipitation (ChIP) assays were performed and showed that PHB-1 and BCoR co-localise in vivo with the distal E2F site identified in the human pitx1 promoter. Amplification of a 372 bp PCR fragment was obtained with input (positive control) and after immunoprecipitation with anti-PHB-1 and anti-BCoR antibodies. Immunoprecipitation with anti-E2F1 did not generate a positive PCR amplification indicating that E2F1 does not co-localise on the pitx1 promoter with PHB-1 and BCoR in spite of the fact that PHB-2 can interact in solution with E2F1 in OA nuclear extracts. The second lane represents a negative control generated by omission of the primary antibody during the immunoprecipitation (−Ab);

FIGS. 6A-C show immunodetection of PHB-1 proteins in human articular cartilage. FIGS. 6A and 6B represent cartilage section obtained from control and OA subjects respectively immunostained with anti-human PHB-1 protein (cat #RB-292-PO, Lab Vision Corp., Fremont Calif., USA). Nuclear signal for PHB-1 was increased significantly in superficial and deep zones (arrow) only in OA cartilage (10× and 40× magnifications). A non specific immunostaining was detected also with the ECM in both groups (normal and OA). (FIG. 6C) Cell scores for PHB-1-nuclear chondrocytes, indicating significant differences between OA and normal (control) cartilage and between the zones for each cartilage type, by Mann-Whitney U test. Values are the mean±SEM of normal (n=3) and OA (n=3) specimens;

FIG. 7 (Table S2) shows peptides (SEQ ID NOs: 17-27) sequencing results identifying PHB-1, PHB-2 and BCoR as part of the repressing complex that binds to the pitx1 E2F-like site;

FIGS. 11A-C. FIG. 11A shows a western blot of PHB-1 expressed in cytoplasm (c) and nucleus (n) of normal and OA human articular chondrocytes. FIG. 11B shows two putative sumoylation sites at proximity of a nuclear export sequence (SEQ ID NO: 68) found in human PHB-1 protein. FIG. 11C shows the two putative sumoylation sites at positions 202 (SEQ ID NO: 69) and 204 (SEQ ID NO: 70);

FIGS. 15A-E show the sequence of a 10 kb pitx1 promoter region (SEQ ID NO: 28) and polymorphisms in that pitx1 promoter region between human subjects. The primers used to cover the different amplicons to cover the 10 kb regions are provided in Table 2 below;

FIGS. 16A-B shows human PHB-1 mRNA nucleotide (obtained from gi|6031190|ref|NM_002634.2) (SEQ ID NO: 29) in FIG. 16A, and amino acid sequence (obtained from gi|4505773|ref|NP002625.1) (SEQ ID NO: 30) in FIG. 16B;

FIGS. 17A-B shows human PHB-2 mRNA nucleotide (obtained from >gi|31543548|ref|NM_007273.3) (SEQ ID NO: 31) (FIG. 17A) and amino acid sequence (obtained from gi|6005854|ref|NP_009204.1)(SEQ ID NO: 32) (FIG. 17B); and FIGS. 18A-C show a sequence comprising 30 bp upstream and 30 bp downstream of the C to T mutation found in the human pitx1 promoter (SEQ ID NO: 1) (FIG. 18A); a nucleotide fragment showing restriction sites surrounding wild-type pitx1 E2F-like site (SEQ ID NO: 16) and (SEQ ID NO: 33) (FIG. 18B); and a nucleotide fragment showing restriction sites surrounding OA mutated human pitx1 E2F-like site (SEQ ID NO: 2) and (SEQ ID NO: 34) (FIG. 18C).

DESCRIPTION OF ILLUSTRATIVE EMBODIMENTS

Figure 1A:
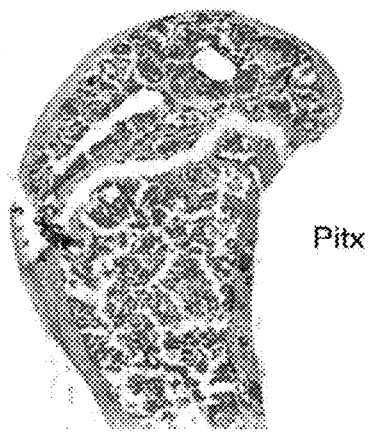
FIGS. 1A-D show a bone histology from a distal end of right femur of 7-month old normal mouse (wt) and pitx1+/− (ht). Goldner staining shows in bone and calcified tissues as green and cartilage and bone marrow cells as red. A representative section of subchondral, cortical and trabecular bone thickening observed in pitx1+/− mice (FIG. 1B) as compared to wild-type ones (FIG. 1A) At higher magnification, a substantial increase in fibrillation and calcification is observed in the articular cartilage of heterozygous mice (FIG. 1D) as compared to wild-type ones (FIG. 1D). Note that original magnification of FIG. 1A
Figure 1C:
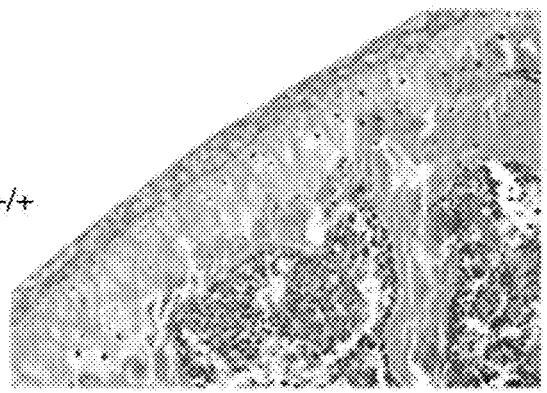
Figure 1B:
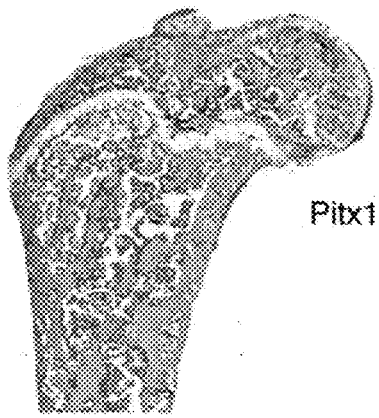
Figure 1D:
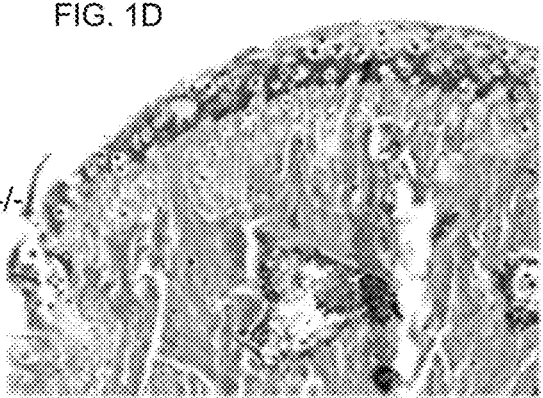

The Applicant observed a correlation between accumulation of PHB-1, PHB-2 and BCoR in the nuclei of articular chondrocytes and OA.

The present invention is illustrated in further details by the following non-limiting examples.
Mice Pitx1+/− mice were prepared as previously reported (65).
Human Specimens Human tissues were collected with the consent of patients. The Institutional Ethics Committee Board of Sainte Justine and Notre Dame Hospitals in Montreal, Canada approved the study protocol. All OA (n=58), RA (n=39) and control subjects (n=18) were evaluated by a certified rheumatologist based on the American College of Rheumatology Diagnostic Subcommittee for OA criteria (25). Of those, 93 patients (43 OA, 39 RA and 11 healthy controls) were used for the genetic study. Other patients (OA and controls) were used either for EMSA analysis, expression analysis or immunohistochemistry studies using cartilage sections.

Articular Chondrocyte Cultures

Cartilage was sectioned from the tibial plateaus, rinsed, finely chopped and cells released by enzymatic digestion performed as previously described (26).

The cells were seeded in Falcon culture flasks at high density ($10^8$ cells per 175 $cm^2$ flask) and grown to confluence in Dulbecco's Modified Eagle's Medium (DMEM; Gibco BRL, Burlington, Ontario, Canada) containing 10% heated-inactivated foetal calf serum (FCS; Hyclone, Logan, Utah) and 1% penicillin/streptomycin (Gibco BRL). Only first passage cultured cells were used. Expression analysis was performed using RNA prepared from articular cartilage isolated from OA patients and age- and gender-matched control subjects.

Total RNA Isolation and RT-PCR

Total RNA was prepared by phenol/chloroform extraction. For RT-PCR, 2 µg of total RNA was reversed transcribed using ThermoScript™ reverse transcriptase (Invitrogen), and the equivalent of 0.1 µg of reverse-transcribed RNA used for PCR reactions. These were carried out in a final volume of 25 µl containing 200 micromolar dNTPs, 1.5 mM MgCl2, 10 pM of each primer, and 1 U Pfx DNA-polymerase (Invitrogen). PCR reactions were performed using the following primers and conditions: human pitx1 (960-bp PCR product), forward primer 5'-CCCACCTC-CATGGACGCCTT-3' (SEQ ID NO: 35); reverse primer 5'-GTCAGCTGTTGTACTGGCACGC-3' (SEQ ID NO: 36) (35 cycles: 94° C./45 seconds, 65° C./45 seconds, 68° C./1 minute), human β-actin (233-bp PCR product), forward primer 5'-GGAAATCGTGCGTGACAT-3' (SEQ ID NO: 37), reverse primer 5'-TCATGATGGAGTTGAATGT AGTT-3' (SEQ ID NO: 38) (32 cycles: 94° C./1 minute, 55° C./1 minute, 72° C./1 minute), human PHB2 (730-bp PCR product), forward primer 5'-GCCCAGAACTT-GAAGGACTT-3' (SEQ ID NO: 39); reverse primer 5'-TCT-TGCTCAGTGCTTCTCCA-3' (SEQ ID NO: 40) (30 cycles: 94° C./45 seconds, 66° C./45 seconds, 72° C./1 minute), human PHB-1 (546-bp PCR product), forward primer 5'-AGTATGTGTGGTTGGGGAAT-3' (SEQ ID NO: 41); reverse primer 5'-GCTCGCTCTGTAAGGTCGTC-3' (SEQ ID NO: 42) (30 cycles: 94° C./45 seconds, 65° C./45 seconds, 72° C./1 minute), and human BCoR (640-bp PCR product), forward primer 5'-*AAAGAGCCG-GATCGCAGG-3' (SEQ ID NO: 43); reverse primer 5'-CACCATTGATGTTGAGAGGGC-3' (SEQ ID NO: 44) (35 cycles: 94° C./45 seconds, 72° C./45 seconds, 72° C./1 minute). For quantitative and semi-quantitative analysis, all amplifications were normalized against that of the housekeeping gene β-actin. PCR amplified product were separated on 1.5% agarose gel (1.0% for semi-quantitative analysis) and visualized by ethidium bromide staining.

Pitx1 Promoter Sequencing

One hundred (100) ng of genomic DNA was mixed in a final volume of 25 µl containing 200 micromolar dNTPs, 1.5 mM MgCl$_2$, 10 pM of each primer (see Table 2 below for full list of primers used), and 1 U Pfx DNA-polymerase (Invitrogen). PCR reactions were performed using the following conditions (35 cycles: 94° C./30 seconds, 60° C./30 seconds, 68° C./1 minute 20 seconds) and primers:

TABLE 2

PITX PROMOTER PRIMERS

| PP1 (962 bp) | forward primer | 5'-CTGTTTGCTCAAGACGCTGA-3' (SEQ ID NO: 45) |
| --- | --- | --- |
| | reverse primer | 5'-CTCGGCCTCACAAAAGAAAC-3' (SEQ ID NO: 46) |

TABLE 2-continued

PITX PROMOTER PRIMERS

| PP2 (966 bp) | forward primer | 5'-TGTCTGCATTCAGGCTGTTC-3' (SEQ ID NO: 47) |
| --- | --- | --- |
| | reverse primer | 5'-GATTCCCTCCTCGAGTCCTT-3' (SEQ ID NO: 48) |
| PP3 (1039 bp) | forward primer | 5'-CAAGTGAGCTGGATGCTGAA-3' (SEQ ID NO: 49) |
| | reverse primer | 5'-AGGGAGTGTCCCTTCACAGA-3' (SEQ ID NO: 50) |
| PP4 (1085 bp) | forward primer | 5'-GCTCAGCCATTCTCAGGAAC-3'; (SEQ ID NO: 51) |
| | reverse primer | 5'-GCCATTGTCCCAGTCAAGAT-3' (SEQ ID NO: 52) |
| PP5 (1011 bp) | forward primer | 5'-TCGCGTCAAGAGGGTATTTT-3' (SEQ ID NO: 53) |
| | reverse primer | 5'-TAGGACCCATGGCTCTACCC-3' (SEQ ID NO: 54) |
| PP6 (1098 bp) | forward primer | 5'-CACGAGTCAGGTGGGAAACT-3' (SEQ ID NO: 55) |
| | reverse primer | 5'-GACGTCTGCTGCTTTTCTGC-3' (SEQ ID NO: 56) |
| PP7 (963 bp) | forward primer | 5'-AGGCACGGACTAGCAGGAC-3' (SEQ ID NO: 57) |
| | reverse primer | 5'-ATGCGGACGAAGCCAGAG-3' (SEQ ID NO: 58) |
| PP8 (986 bp) | forward primer | 5'-TTAGCATTCAGCCCCTCTGT-3' (SEQ ID NO: 59) |
| | reverse primer | 5'-TTCATGAGATGCAGTCAGCAG-3' (SEQ ID NO: 60) |
| PP9 (951 bp) | forward primer | 5'-ACAACTGGTAGGGGCAACAG-3' (SEQ ID NO: 61) |
| | reverse primer | 5'-TGTGTGGCTTTGGCAAATAA-3' (SEQ ID NO: 62) |
| PP10 (990 bp) | forward primer | 5'-GCACTGTGCTCCAACTGTGT-3' (SEQ ID NO: 63) |
| | reverse primer | 5'-GGGGGAGTGTTCTTTTCCTT-3' (SEQ ID NO: 64) |

Immunohistochemistry Assays

IHC assays for Pitx1 were performed using cartilage sections obtained from 8 OA patients (2 males and 6 females, 59±10 years, mean±SEM) undergoing total knee replacement, and from 8 donors without a known history of joint disorders. These tissues were obtained post-mortem from knee condyles within 24 h of death (2 males and six females aged 67±8 years, mean±SEM). For IHC assay with PHB-1 antibody, cartilage was obtained from 3 OA patients (61±8 years, mean±SEM) and 3 control patients (57±28 years, mean±SEM). Tissue specimens were embedded in paraffin, sectioned and examined by IHC for Pitx1 or PHB-1 (and counterstained with hematoxylin for PHB-1 experiments). OA severity was previously evaluated on adjacent sections using the Mankin's histological/histochemical scale (27).

Nuclear Protein Extraction and EMSA

For nuclear protein extraction, cells were rinced with cold 1×PBS and scraped in a buffer containing 10 mM hepes (pH 7.9), 1.5 mM MgCl$_2$, 10 mM KCl, 1% NP$_{40}$, 0.5 mM DTT, 1 mM PMSF, 10 □/ml of aprotinin, 10 □g/ml of leupeptin and 10 □g/ml of pepstatin. They were left on ice for 10-20 minute while mixed regularly using a vortex. After a 3 minute centrifugation at 3000 rpm, the pellet was resuspended in a buffer containing 20 mM hepes (pH 7.9), 25% glycerol, 420 mM NaCl, 1.5 mM MgCl2, 0.2 mM EDTA, 0.5 mM DTT, 2 mM PMSF, 10 □g/ml of aprotinin, 10 Ug/ml of leupeptin and 10 Ug/ml of pepstatin. After a 20 minute incubation on ice and a 2 minute centrifugation at 12500 rpm, the supernatant was collected.

For the analysis of E2F DNA complexes formed in the presence of OA articular chondrocytes, gel mobility shift reactions were performed essentially as previously described (28). Nuclear extracts (5 µg of proteins) were incubated for 30 min at a temperature of between about 20-25° C. in 20 µl of a solution containing 20 mM HEPES (pH 7.5), 40 mM KCl, 5% glycerol, 5 mM spermidine, and 100 ng of poly(dA-dT) and 4 µg of anti-BCoR antibodies (Abcam, ab5276) were added to specific samples (with a + sign). The following probes were then added and incubated for another 30 min at room T°: wild-type 5'-CTGTGCCT-CACTGGCGGCAGTCCTGCTCAA-3' (SEQ ID NO: 65); and mutant 5'-CTGTGCCTCACTGGTGGCAGTCCTGCT-CAA-3' (SEQ ID NO: 66). Samples were then separated on 7% native polyacrylamide gels (acrylamide:bis 29:1 in 0.5× Tris-borate EDTA). Gels were run at 180 V for 3 h with a recirculation pump for the buffer and a cooling tank.

In the presence of radiolabeled probe (14 ng/100,000 cpm) a cold competitor was added as indicated. For supershift analysis, the nuclear extracts were pre-incubated 30 min on ice then incubated in presence of 0.2 µg of E2Fs antibodies (Santa Cruz Biotechnology, Santa Cruz, Calif., USA; listed in Table 3 below) and incubated on ice for 1 h.

TABLE 3

LIST OF ANTIBODIES USED
Antibodies used for results presented in FIGS. 4A-D:

| | |
|---|---|
| E2F1 | (KH95, sc-251 X) Santa Cruz Biotechnology, Santa Cruz, CA, USA |
| E2F3 | (C-18, sc-878 X) Santa Cruz Biotechnology, Santa Cruz, CA, USA |
| E2F4 | (A20, sc-1082 X) Santa Cruz Biotechnology, Santa Cruz, CA, USA |
| E2F5 | (C-20, sc-1083) X Santa Cruz Biotechnology, Santa Cruz, CA, USA |
| E2F6 | (K-20, sc-8176 X) Santa Cruz Biotechnology, Santa Cruz, CA, USA |
| DP1 | (K-20, sc-610 X) Santa Cruz Biotechnology, Santa Cruz, CA, USA |
| Sp1 | (1C6, sc-420 X) Santa Cruz Biotechnology, Santa Cruz, CA, USA |
| Sp3 | (D-20, sc-644 X) Santa Cruz Biotechnology, Santa Cruz, CA, USA |
| BCoR | (ab5276) Abcam Inc., Camridge, MA, USA |
| RXR□ | (D-20, sc-553 X) Santa Cruz Biotechnology, Santa Cruz, CA, USA |
| Others not shown: | |
| E2F1 | (H-137, sc-22820 X) Santa Cruz Biotechnology, Santa Cruz, CA, USA |
| E2F2 | (L-20, sc-632 X) Santa Cruz Biotechnology, Santa Cruz, CA, USA |
| E2F3 | (N-20, sc-879 X) Santa Cruz Biotechnology, Santa Cruz, CA, USA |
| E2F8 | (H00079733-M01) Abnova Corporation, Taipei, Taiwan |
| DP-2 | (C-20, sc-829 X) Santa Cruz Biotechnology, Santa Cruz, CA, USA |
| Sp1 | (H-225, sc-14027 X) Santa Cruz Biotechnology, Santa Cruz, CA, USA |

The sequences of the oligonucleotide probes were: E2F-like (wild-type) 5'-CTGTGCCTCACTGGCGGCAGTCCT-GCTCAA-3' (SEQ ID NO: 65); and E2F-like mutant (OA) site, 5'-CTGTGCCTCACTGGTGGCAGTCCTGCTCAA-3' (SEQ ID NO: 66). Samples were then separated on 7% native polyacrylamide gels (acrylamide:bis 29:1 in 0.5× Tris-borate EDTA). Gels were run at 180 V for 3 h with a recirculation pump for the buffer and a cooling tank. For analysis of dissociation rate (off-rate), a 70-fold excess of unlabeled competitor oligonucleotide corresponding to the wild-type E2F site found in human pitx1 promoter was added after 30 min of incubation on ice with either labelled probe. Aliquots from the same binding mixture were taken at different times and frozen on dry ice to stop the reaction prior loading on gel.

Nuclear Complexes Precipitation by DNA Pull Down

Nuclear extracts (300 mg of protein) prepared from cultured human OA articular chondrocytes from knee joints were initially incubated in presence of 25 ml of streptavidin-magnetic beads slurry (BioClone Inc. San Diego, Calif., USA) in order to remove unspecific protein interactions. Following this, pre-cleared nuclear extracts were incubated with 5 mg of biotinylated ds probe (5'-CTGTGCCT-CACTGGTGGCAGTCCTG CTCAA-3' (SEQ ID NO: 66)) for 2 h at 4° C. with slow agitation in 1×EMSA binding buffer. 50 ml of streptavidin-magnetic beads slurry was added and after 1 h of incubation at 4° C. the bound complexes were recovered using a magnetic stand and several washes according to the manufacturer's specifications. The complexes were then detached from the beads in a boiling mixture of NuPAGE™ 4×LDS loading buffer (Invitrogen) and β-mercaptoethanol. After centrifugation, the supernatant was loaded on a SDS-PAGE gel and visualized by Coomassie blue staining.

Co-Immunoprecipitation

Nuclear and cytoplasmic extracts obtained from chondrocytes of normal or OA patients were incubated overnight with goat anti-PHB-1 antibodies (Santa Cruz, sc-18196). Immunoprecipitated proteins were collected using protein A-sepharose beads. 50 µg of proteins were loaded and run on SDS-PAGE. Proteins were then transferred to a nitrocellulose membrane at 100V for 70 minutes. For blotting, rabbit anti-PHB-1 antibodies (Santa Cruz, sc-28259) were used in a 15:10000 dilution.

Transfection

The Lipofectamine™ 2000 protocole from Invitrogen (www.invitrogen.com) was followed: All amounts and volumes are given on a per well basis. A DNA (µg) to Lipofectamine™ 2000 (µl) ratio of 1:2 to 1:3 was used. Cells were transfected at high cell density for high efficiency, high expression levels, and to minimize cytotoxicity. One day before transfection, 0.5-2×10$^5$ cells were plated in 500 µl of growth medium without antibiotics so that cells were 90-95% confluent at the time of transfection. For each transfection sample, complexes were prepared as follows: a. DNA was diluted in 50 µl of Opti-MEM® I Reduced Serum Medium without serum and mixed gently. Lipofectamine™ 2000 was gently mixed before used, then the appropriate amount was diluted in 50 µl of Opti-MEM® I Medium and incubated for 5 minutes at room temperature. After the 5 minute incubation, the diluted DNA was combined with diluted Lipofectamine™ 2000 (total volume=100 µl), mixed gently and incubated for 20 minutes at room temperature. The 100 µl of complexes were added to each well containing cells and medium. The plate was mixed gently by rocking back and forth. The cells were incubated at 37° C. in a $CO_2$ incubator for 18-48 hours prior to testing for transgene expression.

Peptide Sequencing Analysis

Bands containing proteins from the DNA pulldown assay and EMSA were cut, washed, sliced, dried and rehydrated in ammonium bicarbonate buffer. Proteins were digested with trypsin and extracted from the gel pieces using 50% acetonitrile and 0.1% formic acid. Samples were evaporated to dryness and resuspended in 3% acetonitrile-0.1% formic acid in a final volume of 20 μl.

Mass Spectroscopy Analysis

Samples (10 μl volume) were analyzed using a LC-MS/MS system consisting of Agilent™ 1100 Series nanoflow liquid chromatography system and 1100 Series LC MSD SL ion trap mass spectrometer (Agilent Technologies, Palo Alto, Calif., USA). Peptides were enriched on a Zorbax™ 300SB-C18 trap column (5 μm, 5×0.3 mm) and separated by reversed phase on a Zorbax™ 300SB-C18 analytical column (3.5 μm, 150×0.075 mm, Agilent) with a gradient of 5-90% acetonitrile in 0.1% formic acid at a flow rate of 300 nl/min. The column eluent was sprayed directly into the mass spectrometer. Spectra were interpreted using Spectrum Mill™ software (Agilent) and NCBI NR mammalian database.

Extraction Parameters with Spectrum Mill™ Software

Cysteine modification: carbamidomethylation; sequence tag length >1; mass range of precursor ions: 600.0 to 4000.0 Da; scan time range: 0 to 300 minutes; scans were merged for same precursor m/z: +/−15 seconds; +/−1.4 m/z.

Chromatin Immunoprecipitation Assays

ChIP experiment was carried out with the ChIP-IT™ kit (Active Motif, Carlsbad, Calif., USA) ChIP-ITT™ kit. Briefly, cells were cross-linked with 1% formaldehyde and collected in cell scraping solution. Nuclear extraction was then performed using lysis buffer and total DNA was sheared to an approximate length of 0.3-1.5 kb (Branson Sonifier™ 450). Chromatin was pre-cleared with Protein G beads and separated as follows: total input, negative control without antibody, and ChIP with either anti-PHB-1 (Santa Cruz), anti-BCoR (Abcam) or anti-E2F1 antibodies (Santa Cruz). After overnight incubation with the appropriate antibody, Protein G beads were added and several washes were carefully done. Chromatin was eluted from the beads using ChIP elution buffer. Cross-linking reversal was done by heating samples at 65° C. for 4 h, and DNA was purified using columns provided in the kit. PCR analysis was performed using the following primers and conditions: human pitx1 promoter harbouring the E2F site (372 bp PCR product), forward primer 5'-GCTCAGCCATTCTCAGGAAC-3' (SEQ ID NO: 51); reverse primer 5'-CCACCTAC-CTCTTTCTGCCT-3' (SEQ ID NO: 67) (35 cycles: 94° C./45 seconds, 68° C./45 seconds, 68° C./1 minute).

Statistical Analysis

The 95% confidence intervals for sensitivity, specificity, positive predictive value and negative predictive value presented in Table 4 were calculated according to Deeks and Altman (29). The association between the presence of mutation and diagnosis was assessed using the Fisher's Exact Test (two-tailed test). A p value <0.05 was considered statistically significant.

Example 1

Figure 2A:
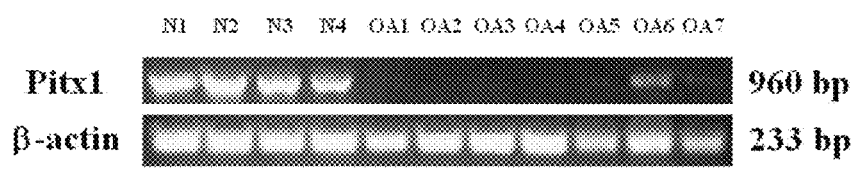
FIGS. 2A-D compare Pitx1 expression in articular chondrocytes from OA patients and matched control subjects.
Figure 2B:
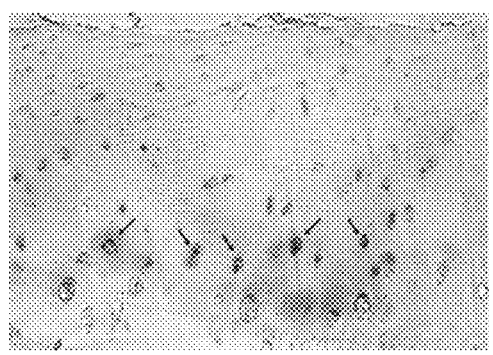
Figure 2C:
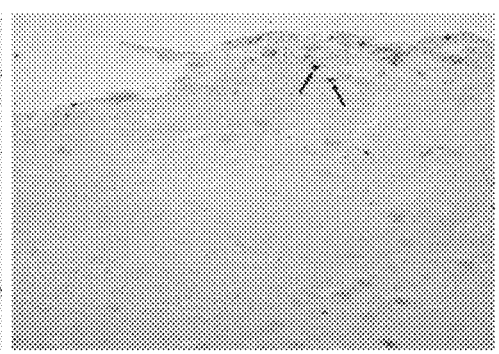
Figure 2D:
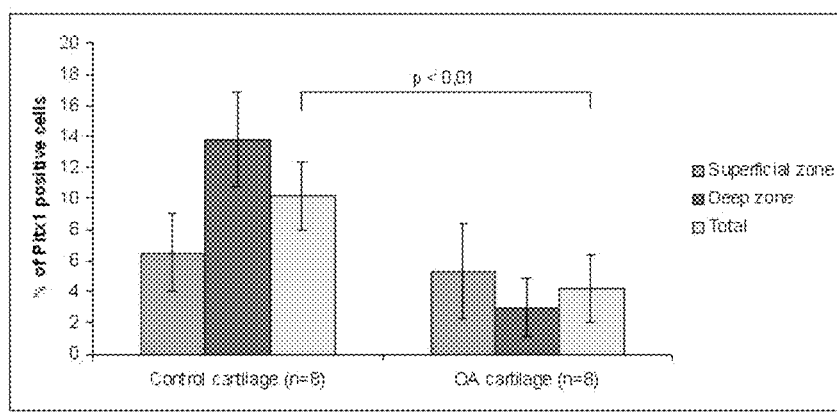

Comparison of Pitx1 Expression in Articular Chondrocytes of OA Subjects with that of in Articular Chondrocytes Matched Controls To determine whether pitx1 plays a role in the genetic control of OA onset, an expression analysis of pitx1 gene using RNA prepared from articular chondrocyte cultures derived from knee cartilage of OA patients (n=7) and age- and gender-matched control subjects (n=4) was performed. Pitx1 expression was detected only in articular chondrocytes derived from matched controls, while in OA articular chondrocytes, Pitx1 expression was abrogated or barely detectable by RT-PCR (FIG. 2A). Analysis of Pitx1 protein levels and distribution in human knee joint sections showed Pitx1 proteins only in control cartilages (n=8), while Pitx1 proteins were hardly detected in OA cartilage sections (n=8) (FIG. 2B-D).

Example 2

Identification of Pitx1 Promoter Mutation

To examine the mechanisms turning off pitx1 gene expression in OA patients, the 5' regulatory region of human pitx1 gene was examined for specific mutations leading to a progressive loss of Pitx1 expression during adulthood. Sequencing analysis of genomic DNA obtained from OA, rheumatoid arthritis (RA) and matched control subjects revealed, along a 10 kb promoter region of human pitx1 gene, a single homozygous mutation (−3727 C→T) (position corresponds to distance from transcription point) affecting only OA patients (11/43) with a high frequency (25%) while none of the RA patients (0/29) and matched control subjects (0/11) had the homozygous mutation. The specificity, the positive predictive values and negative predictive values of the mutation were calculated for each group as reported in Table 4 below. A statistically significant association between the mutation and diagnosis was calculated (two-tailed test) by comparing OA versus RA patients (p=0.002) or by combining RA and control subjects (p<0.001). Heterozygous mutation was present in OA patients (3/43), RA subjects (6/29) and control subjects (3/11) although the association between the heterozygous mutation and diagnosis was not statistically significant (p=0.14 for OA versus RA and p=0.09 for OA versus control).

TABLE 4

SENSITIVITY, SPECIFICITY, POSITIVE PREDICTIVE VALUE* (PPV) AND NEGATIVE PREDICTIVE VALUE** (NPV) OF PITX1 mutation (−3727 C→T) for OA

| Mutation | Sensitivity | Specificity | PPV | NPV |
| --- | --- | --- | --- | --- |
| Homozygous | 25.6 (13.8-39.5) | 100.0 (71.5-100.0) | 100.0 (71.5-100.0) | 25.6 (13.8-39.5) |
| OA-Control | | 100.0 (88.1-100.0) | 100.0 (71.5-100.0) | 47.5 (35.2-60.0) |
| OA-RA | | 100.0 (97.6-100.0) | 100.0 (71.5-100.0) | 55.6 (44.0-66.8) |
| OA-(Control & RA) | | | | |
| Heterozygous | 7.0 (1.4-16.4) | 72.7 (39.0-94.0) | | |
| OA-Control | | 79.3 (60.3-92.0) | | |
| OA-RA | | 77.5 (63.4-88.9) | | |
| OA-(Control & RA) | | | | |

Promoter sequence analysis performed with the ALGGEN PROMO™ search program (using TRANSFAC™ version 8.3; (35, 36) revealed that the homozygous mutation was localized within the core of an E2F-like site (10, 11). The sequence encompassing the E2F-like site found upstream of the human pitx1 gene is more distal although it shows an overlap with several functional E2F sites and also with an adjacent region termed cyclin homology region (CHR) found in promoter of genes involved in the regulation of cell cycle 12 (FIG. 3). The transcriptional relationship between pitx1 and E2Fs is further strengthened by the works of Muller et al. showing that E2F1, E2F2 and E2F3 up regulate Pitx1 expression by several fold in osteosarcoma cell line U2OS (13). To date, eight different mammalian E2Fs have been cloned; each of them can heterodimerize with either DP1 or DP2/3 proteins and bind with similar affinity to the same collection of target sites (14). These factors could be broadly divided into two classes: activators (E2F1-3) and repressors (E2F4-8) of transcription (15), which could explain why E2F sites on a promoter do not always indicate that it is induced by E2F but, on the contrary, that it can be repressed through those sites as well (16-18).

Example 3

Determination of Functional Consequences of Mutation in the E2F-like Site on Complex Binding To determine the functional consequences of the homozygous mutation found in OA patients, it was investigated whether E2Fs were able to bind this E2F-like site using nuclear extracts prepared with OA articular chondrocytes as described above. EMSA analysis using both radiolabeled E2F-like sites (wild-type FIG. 4A versus mutant FIG. 4B) showed no supershift of the bound complex with any antibodies against E2Fs, or their dimerization partners DP-1 or DP-2 (E2F2, E2F8 and DP2 data not shown). The Sp1 and Sp3 transcription factors were also analysed since they bind GC-rich regions such as the E2F-like site found in the human Pitx1 promoter. Unfortunately, there was no supershift with either anti-Sp1 or anti-Sp3 antibodies. Addition of BCoR antibodies generated the binding of an additional lower complex bound in presence of either probes although the binding was increased with the mutant one as is mostly apparent by comparing lanes 4 to 6. Functional analysis by EMSA revealed a slower dissociation rate when the complex was bound to the mutant E2F probe indicating that C→T mutation increased the stability of the bound complex.

Example 4

Identification of BCoR as a Member of the Pitx1 Repressor Complex

In order to characterize the nature of the complex identified in Example 3, bands corresponding to the bound complex were cut and extracted from an EMSA wet gel to perform a peptide sequencing analysis combined with tandem mass spectrometry.

This experiment led to the identification of peptides corresponding to BCoR, a known co-repressor (see FIG. 7). The presence of BCoR in the bound complex was confirmed also by the detection of an additional lower band in EMSA when BCoR antibodies were added (see Example 3 and FIG. 4A-B).

Example 5

Identification of PHB-1 and PHB-2 as Members of the Pitx1 Repressor Complex

Figure 8:
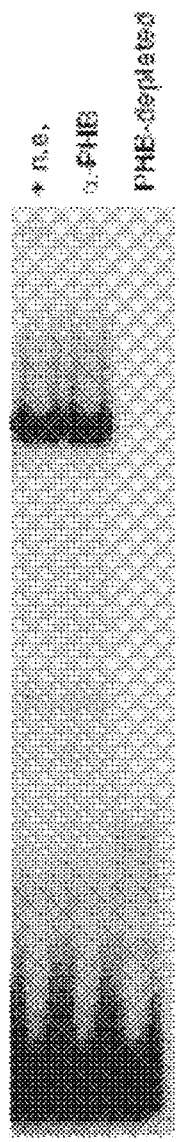
FIG. 8 shows EMSA using total nuclear extract (alone or with PHB-1 antibody (Prohibitin Ab-2 (RB-292-P0) Lab Vision Corp., Fremont, Calif.)) and PHB-1-depleted nuclear extract. The use of a PHB-1 antibody did not allow any supershift but depletion of PHB-1 in OA nuclear extract abrogated all the complexes formation bound to the wild-type radiolabeled probe.

A DNA-pull down method as described above was used with a biotinylated double-stranded oligonucleotide harboring the mutant E2F-like site to allow the identification of peptides corresponding to prohibitin (PHB-1) and prohibitone (PHB-2) (FIG. 7). To confirm the presence of PHB-1 in the bound complex, an immuno-depletion of PHB-1 in nuclear extracts prepared from OA articular chondrocytes was performed and no binding was observed in EMSA with PHB-1 depleted nuclear extracts using either radiolabeled probes (FIG. 8).

Example 6

Figure 10:
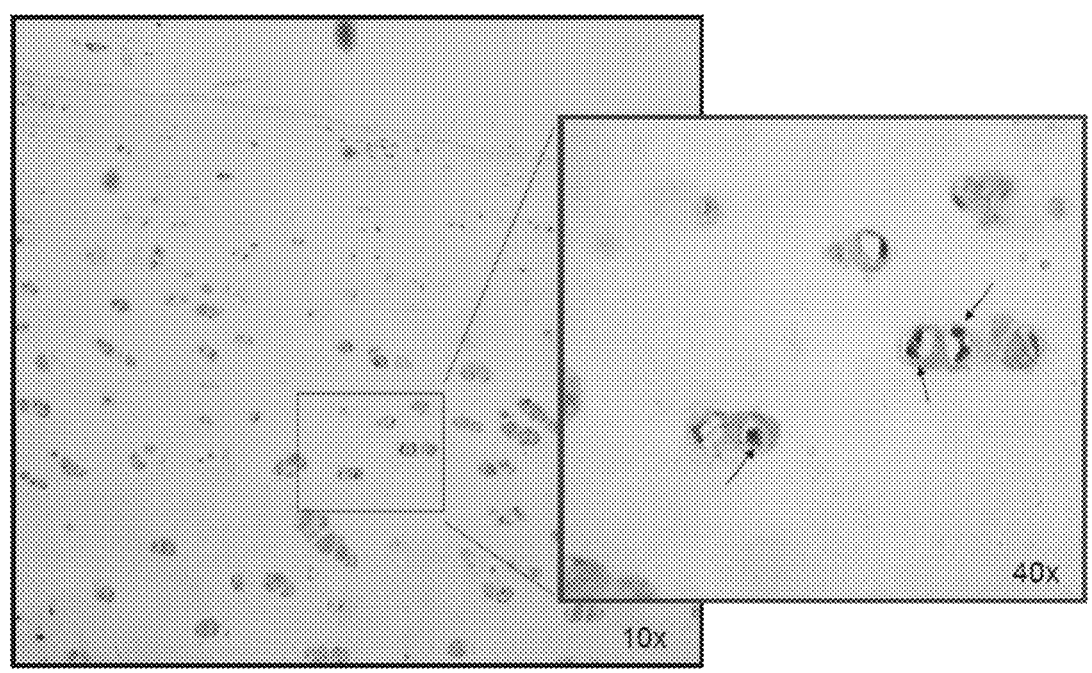
FIG. 10 shows the nuclear localization of PHB-1 in OA patients by immunohistochemistry using an anti-PHB-1 (Santa Cruz, sc-18196)

Identification of the PHB-1 and PHB-2 Nucleus Localization in OA and Normal Articular Chondrocytes The cellular localization of PHB-1 was compared in normal and OA articular chondrocytes by IHC assays using anti-PHB-1 antibodies. As may be seen in FIG. 6A-C, an increased nuclear localization of PHB-1 was observed in OA cartilages when compared to age-matched control cartilages. See also FIG. 10 for a larger magnification using different anti-PHB-1 antibodies. The cellular localization of PHB-2 is also compared in normal and OA articular chondrocytes by IHC assays using anti-PHB-2 antibodies.

Example 7

Co-immunoprecipitation Assay of PHB-1, PHB-2 and E2F1

Figure 5A:
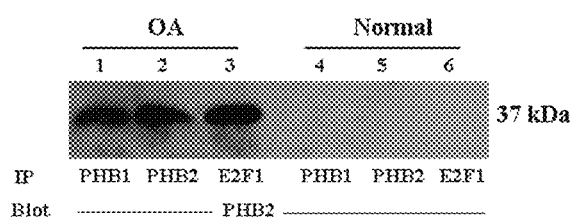
FIGS. 5A-B show in vitro and in vivo characterization of PHB-1, PHB-2 and BCoR interactions in primary OA articular chondrocytes.

Co-immunoprecipitation assay of PHB-1, PHB-2 and E2F1 were performed as described above. Physical interactions between PHB-1, PHB-2 and E2F1 were detected in nuclear extracts prepared from human OA articular chondrocytes while controls did not show any interaction with PHB-2 (FIG. 5A).

Example 8

Figure 5B:

Chip Assay to Demonstrate the Functionality of the EF2 Site in OA Chondrocytes and Co-occupancy of PHB-1 and BCoR Chromatin immunoprecipitation (ChIP) assays were performed as described above with primary OA articular chondrocytes cultures to examine the co-occupancy of PHB-1, BCoR and E2F1 on the E2F-responsive element identified in human pitx1 promoter. PHB-1 and BCoR co-localised in vivo only in OA chondrocytes confirming also the functionality and specificity of this E2F site although E2F1 was not detected (FIG. 5B). The interaction is however not dependent on the −3727 C→T mutation since wild-type also interacts with the repressor complex.

Example 9

Identification of the −3727 C to T Homozygous Mutation in a Subject Sample

Genomic DNA is isolated (directly using available commercial kits or after extraction of lymphocytes) from the subject saliva or blood. The human pitx1 promoter region harbouring the −3727 C→T homozygous mutation is then amplified by PCR using specific primers. Amplified products are identified by direct sequencing using genomic DNA extracted from lymphocytes. They may also be digested with either restriction enzyme AciI or Fnu4H to detect the presence of the mutation. Because replacement of C by T in OA patients abrogates AciI and Fnu4HI restriction sites normally present in the wild-type sequence, the presence of the mutation is assessed by absence of relevant restriction fragments.

Example 10

Assay to Identify Blood and Synovial Concentration Levels of PHB-1, PHB-2 or Native Peptide Agonists to Cell Surface PHB-1 in Subjects PHB-1 and PHB-2 are also found in the bloodstream (Mishra et al. 2006). Diet-induced obesity was successfully reversed in mice through subcutaneous injection of a chimeric proapoptotic peptide that binds to PHB-1 at the cell surface of white fat vasculature (57). The peptide cut off the blood supply to fat tissue leading to its reabsorption. Most of the OA patients are obese. Dosage of PHB-1 in biological fluids like plasma/serum, urine or synovial fluids are performed using an ELISA method (see for instance 58).

Example 11

Figure 9:
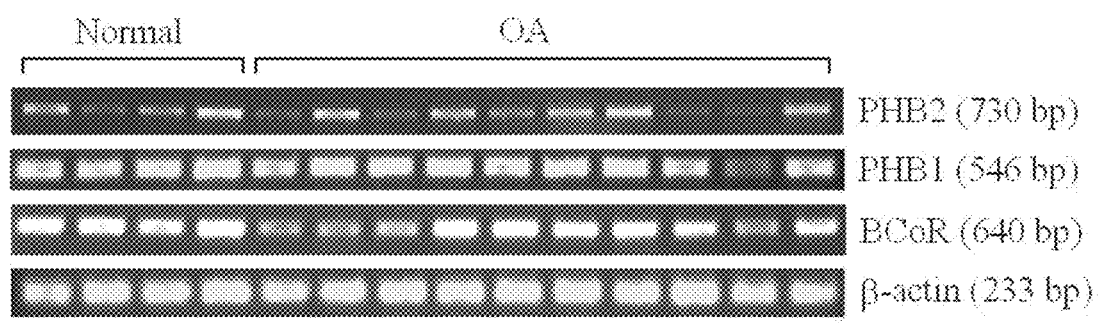
FIG. 9 shows an expression analysis by semi-quantitative RT-PCR of PHB2, PHB-1 and BCoR in human articular chondrocytes (normal vs. OA)

Assay to Identify RNA Levels of PHB-1, PHB-2 and BCoR Between Normal and OA Human Articular Chondrocytes Expression analysis was performed as described above by semi-quantitative RT-PCR of PHB-2, PHB-1 and BCoR in human articular chondrocytes (normal vs. OA). RNA was extracted from 4 normal patients and 10 OA patients. No significant change was observed between normal and OA articular chondrocytes as may be seen in FIG. 9.

Example 12

Detection of PHB-1 Immunoreactive Bands in Nuclear and Cytoplasm of Human Articular Chondrocyte Fractions from OA Subjects Co-immunoprecipitation of PHB-1 was performed as described above.

The detection using an anti-PHB-1 antibody revealed (FIG. 11A) a major PHB-1 immunoreactive band of 32 kDa, which corresponds to the molecular weight of the PHB-1 alone. PHB-1 immunoreactive bands of higher molecular weight suggest post-translational modifications of PHB-1 modifying its weight.

On FIG. 11A, a higher molecular weight bands pattern is detected mostly in the nuclear fraction of OA patients. This pattern is not found in the nuclear fraction of the control subject.

Example 13

Comparison of Sumoylation of PHB-1 Between Normal and OA Human Articular Chondrocytes Sumoylation is the binding of one or more small proteins of 12 kDa, designated SUMO, to another protein. SUMO proteins will lead to a laddering profile of the protein to which they are binding in a western blot. The hypothesis that the laddering of PHB-1 immunoreactive bands observed in FIG. 11A, was caused by sumoylation was thus tested.

SUMOsp (SUMOsp: a web server for sumoylation site prediction. Yu Xue, Fengfeng Zhou, Chuanhai Fu, Ying Xu, and Xuebiao Yao. Nucl Acids Res 34: W254-W257, 2006.) predicted that PHB-1 contains two putative sumoylation sites at proximity of a nuclear export sequence (NES), namely at positions 204 and 240. FIG. 11B presents the position of these putative sites and the sequence of the NES (SEQ ID NO: 68). The table in FIG. 11C presents the sequences of these sites, namely 204 (SEQ ID NO: 69) and 240 (SEQ ID NO: 70).

Total proteins of nuclear and cytoplasmic fractions from articular chondrocytes of OA patients (C73 and C74) and age-matched control patient (C75) were then analyzed by western blot against PHB-1 and Pan-SUMO. They were loaded and run on SDS-PAGE. Proteins were then transferred to a PVDF membrane at 100V for 70 minutes. The 3 markers used, namely lamine (nucleus), GAPDH (cytoplasm) and ATP-Synthase (mitochondria), show that the samples have been separated efficiently into a nuclear fraction (X-N) and a cytoplasmic fraction (Cyto). These antibodies were used for blotting: anti-PHB-1 (Santa Cruz, sc-28259), Pan SUMO antibodies (ABGENT, AP1299a), anti-Lamin A/C (Cell Signaling, #2032), anti-GAPDH (Santa Cruz, sc-20357) and anti-F1-ATPase (Santa Cruz, sc-16689).

Figure 12:
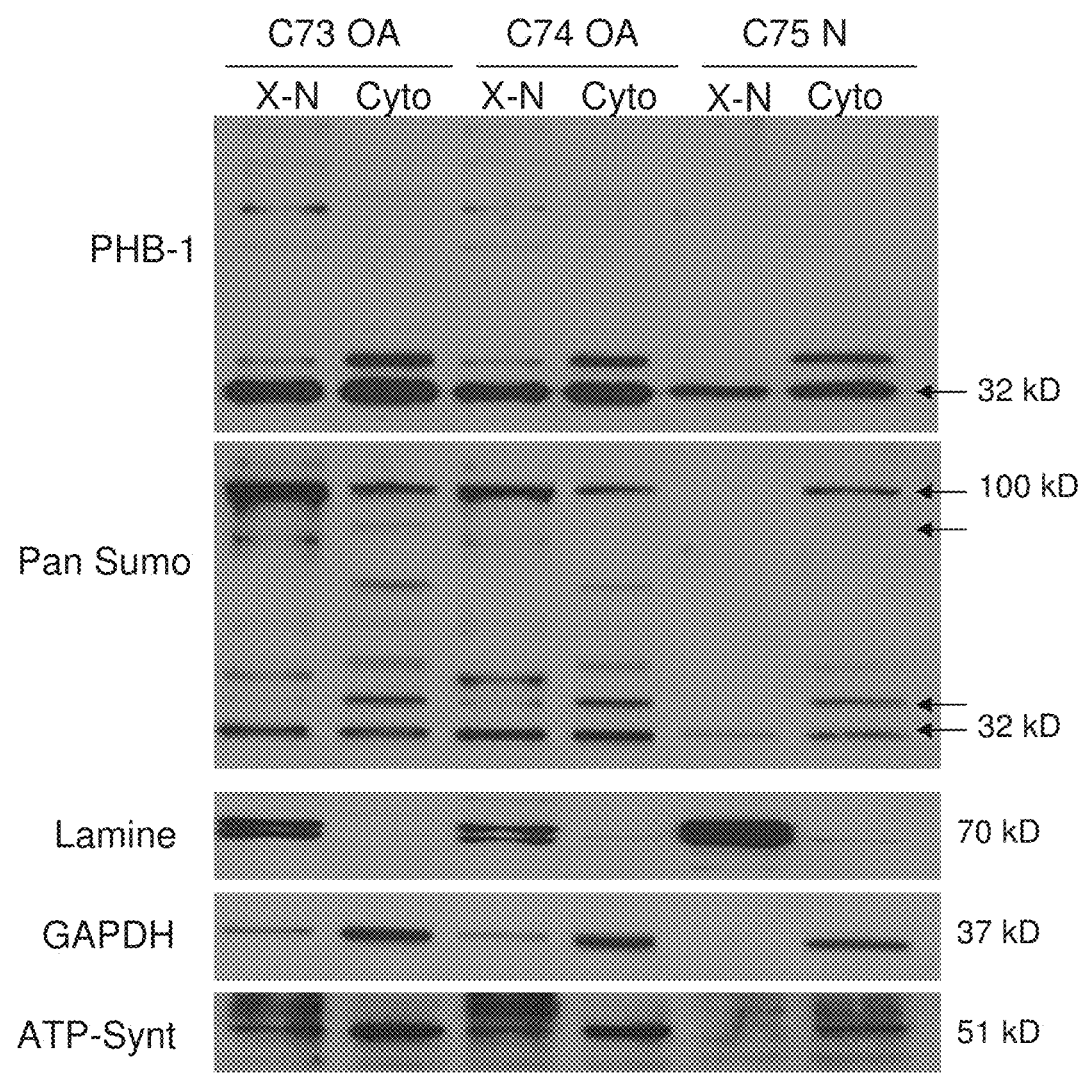
FIG. 12 presents the nuclear (n) and cytoplasmic (c) protein expression of PHB-1 and Pan-SUMO in articular chondrocytes of OA patients (C73 and C74) and control patient (C75) analyzed by western blot. 3 markers are presented: Lamine (nucleus), GAPDH (cytoplasm) and ATP-Synthase (mitochondria)

Pan-SUMO immunoreactive bands in FIG. 12 reveal proteins (different proteins or a single protein) modified by the binding of one or more SUMO proteins, as reflected by bands with increasing molecular weights.

FIG. 12 shows that the two OA subjects have the same sumoylation pattern in the nuclear fraction, and that this pattern is absent from the control subject. Arrows (except for the 32 kDa bands) point to bands that are immunoreactive to both PHB-1 and PAN SUMO, and are detected in the nuclear fraction of OA subjects but not in the control nuclear fraction. These results suggest that sumoylation contributes to PHB-1 nuclear localization in OA patients.

Clinically, this suggests that increased sumoylation is the primary event leading to PHB-1 nuclear accumulation and repression of Pitx1 in primary OA. The biological consequences of sumoylation include the increase of protein stability, increase targeting of proteins (including transcription factors) from the cytoplasm to the nucleus, regulates transcriptional activities of proteins, mediates the binding of the protein to other proteins and increases the repressor activity of certain transcription factors. Recent studies linked sumoylation of several proteins to important diseases (neurodegenerative diseases, acute promyelocytic leukemia, type I diabetes and other disorders). The regulation of these postranslational modifications may provide new targets for therapeutic intervention in several human diseases.

PHB-1 is a molecule having a molecular weight of less than 50 kDa and can passively penetrate the cell nucleus. In normal subjects, PHB-1 is quickly exported out of the cell nucleus through the exportin system by the recognition of a nucleus export signal (NES). Without being bound by such hypothesis, the proximity of the 2 sumoylation sites to the NES, could contribute to the nuclear retention of PHB-1 in OA subjects by hiding the NES and thereby prevent the recognition PHB-1 by exportin.

Example 14

Determination of Repression of mir20a Promoter by Co-Repressors PHB-1, PHB-2, BCoR and Combinations Thereof MG-63 cells were transfected as described above with Lipofectamine™ 2000 during 6 hours. After the transfection, fresh media was added to cells during 24 hours and $10^{-7}$ M 4-OH-Tamoxifen was added to cells during 24 hours.

Figure 13:
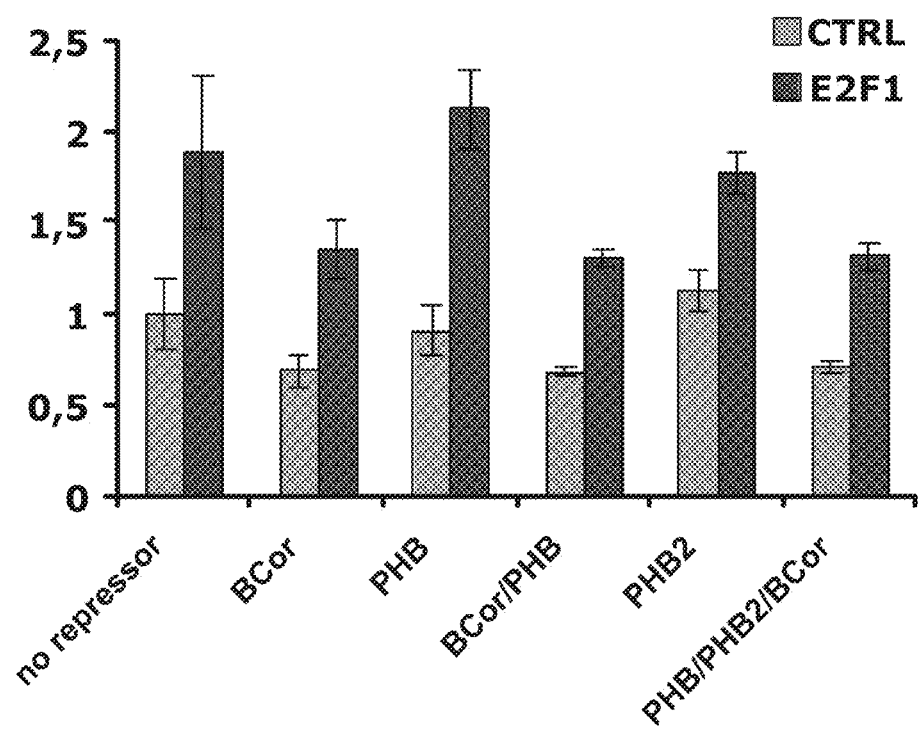
FIG. 13 graphically presents the repression of mir20a promoter by corepressors BCoR, PHB-1, PHB-2 and combinations thereof.

The luciferase assay was then performed. Results are presented in FIG. 13. Results are expressed by the fold induction of luciferase signal of reporter construct compared to that of a control. The control (CTRL) luciferase activity was that measured in osteoblastic MG-63 cells co-transfected with mir20A reporter promoter, known to be regulated by E2Fs, from Sylvestre Y et al. 2007, pBAPE-ER and pLPC NEP-Flag vectors. The E2F1 was the condition where cells were co-transfected with E2F1-ER over-expressing vector. All luciferase signal was normalized by a beta-gal reporter vector. The X-axis represents the names of each repressor co-overexpressed in the conditions tested. This transient transfection assay shows that BCoR alone or in combinations with PHB-1 (designated PHB in FIG. 13) and/or PHB-2 is sufficient to repress the induction of an E2F reporter construct like mir20a even in the presence of the mir20a agonist E2F1.

Example 15

Figure 14:
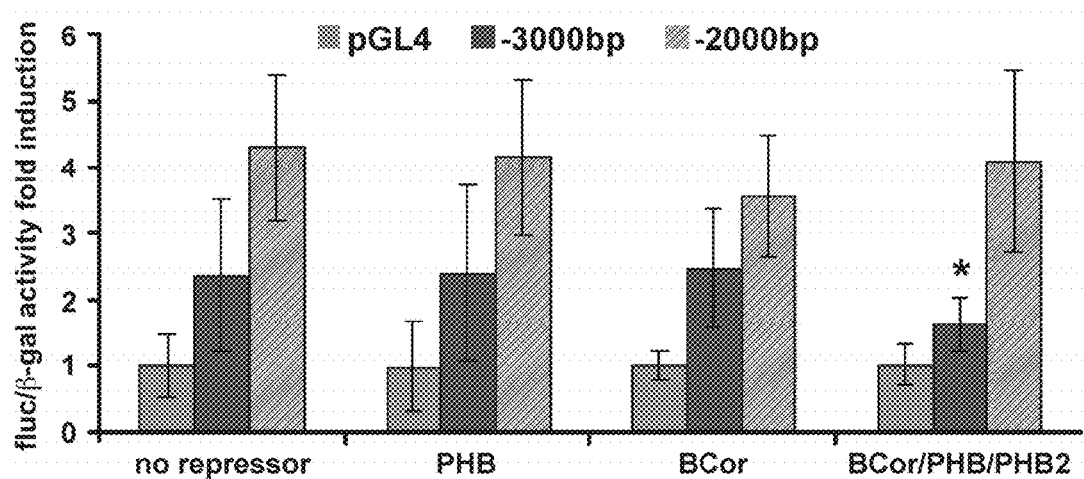
FIG. 14 graphically presents the repression of human PITX1 gene promoter promoter by corepressors BCoR, PHB-1, PHB-2 and combinations thereof.

Determination of Repression of PITX1 Promoter by Corepressors PHB-1, PHB-2, BCoR and Combinations Thereof MG-63 cells were transfected as described above with a vector containing 3000 or 2000 bp of PITX1 gene promoter upstream of a firefly luciferase gene. Cells were synchronised 16 h by serum starvation. Fresh serum was added during 48 h and the luciferase assay was performed. The luciferase signal was normalised against beta-gal. Results are expressed by the fold induction of luciferase signal compared to a luciferase signal from an empty vector. Results are presented in FIG. 14. These results show the repression driven when BCoR, PHB-1 and PHB2 are combined together using a fragment of human pitx1 promoter (fragment −3000 bp). This demonstrates the repressor activity of this complex. Without being bound by this hypothesis, it is suggested that more than one E2F-like sites may be present on the PITX1 gene.

Example 16

Analysis of Prohibitin-CRM-1 Interaction in Normal and OA Articular Chondrocytes PHB-1 physical interaction with CRM-1 is measured by co-IP assays as described above, while Western blot with anti-CRM-1 antibodies (Santa Cruz) are performed with nuclear extracts prepared with normal and OA articular chondrocytes to assess changes in CRM-1 levels in normal versus OA cartilage cells. In parallel, functionality of CRM-1 is tested by an immunostaining method. Cells are either untreated or treated with 30 µM camptothecin (Sigma) for 4 h, a topoisomerase I inhibitor that stimulates the nuclear export of PHB-1 through a CRM-1-dependent mechanism. Subcellular localisation of p53 is used as internal control since p53 normally co-localises with PHB-1 and migrate to the cytoplasm upon camptothecin treatment. Cells are fixed in 4% PFA for 5 min and blocked in 5% BSA in PBS buffer at RT for 1 h, followed by primary antibody incubations overnight at 4° C. After washing, secondary antibody incubation is performed with goat anti anti-mouse IgG Alexa™ Fluor-488 (green) and goat anti-rabbit IgG Alexa™ Fluor-546 (red) for 30 min at room temperature. Cells are visualised with a Zeiss™ LSM 510 confocal microscope. Finally, the contribution of TGF-β signalling to PHB-1 nuclear export is investigated since it was reported that TGF-β1 mediates the nuclear export of PHB-1 in a prostate cancer cell line.

Example 17

OA Genetic Association Studies

Genotyping of the (−3727 C→T) found in the promoter of human pitx1 gene is performed in a large cohort that currently comprises 1,400 cases (510 males and 890 females) and 750 controls (350 females and 400 males) well characterised. The cases have each undergone elective joint-replacement surgery (hip or knee) due to severe, end-stage primary OA. The controls have no symptoms of OA or of any other joint or musculoskeletal disease. The cases and controls are all aged 45 or over, they are unrelated to each other and are of UK Caucasian origin. The DNA from the cases and the controls are arrayed on to 96-well microtitre plates at concentrations of 100 ng/µl and 10 g/µl. Results are analysed in function of differences in genotype or allele frequencies between OA cases and controls. The cases are stratified by sex, age, by joint replaced or by sex combined with joint replaced or age combined with joint replaced.

Genetic association, and Hardy-Weinberg equilibrium for the distribution of genotypes, are tested by $X^2$ analysis with Yates's correction. Odds ratios are calculated with 95 percent confidence intervals. The pair wise linkage disequilibrium coefficient $(r2)^Z$ is calculated using the GOLD™ program (59). Haplotype frequencies between variants showing evidence of linkage disequilibrium at r2>0.2 is estimated using the EH-PLUS™ program (60). Haplotype frequency differences are then compared using $X^2$.

Example 13

Characterisation of Nuclear Factors Known to Interact with PHB-1 and/or PHB-2

Additional partners of PHB-1 and PHB-2 are expected to exist since there are no indications in the literature that either molecule can bind directly to the DNA to exert their transcriptional repression. It was shown that prohibitin recruits Brg-1/Brm to E2F-responsive promoters, and that this recruitment is required for the repression of E2F-mediated transcription by PHB-1. Although PHB-1 associates with, and recruits, Brg-1 and Brm independently of pRb, prohibitin/Brg-1/Brm-mediated transcriptional repression requires pRb. PHB-1 and PHB-2 mediated transcriptional repression required also histone-deacetylase activity (HDAC1), but unlike pRb, additional co-repressors like N-CoR are also involved (24,41). In addition, PHB-2 also associates with the class II histone deacetylase HDAC5. Finally, it was reported that PHB-2 specifically interacts with the chicken ovalbumin upstream binding transcription factors I and II (COUP-TFI and COUP-TF-II). The nuclear receptor chicken ovalbumin upstream binding transcription factor I was found to cooperate with PHB-2 and histone deacetylases in the repression of target genes. PHB-1 and PHB-2 thus appear to repress E2F-mediated transcription utilising different molecular mediators and facilitate channelling of specific signalling pathways to the cell cycle machinery.

Whether pitx1 repression is mediated by recruitment of Brg-1/Brm to this E2F site is investigated. The contribution of specific histone deacetylases (HDACs) is also investigated. To test whether Brg-1, Brm and prohibitin physically interact in OA nuclear extracts, co-immunoprecipitation studies are carried out using nuclear extracts from OA articular chondrocytes, which contain PHB-1 and PHB-2 endogenously. Immunoprecipitation are then performed with anti-cmyc (negative control), anti-Brg-1 or anti-Brm antibodies, and the precipitated proteins are then immunoblotted for PHB-1 or PHB-2. Normal articular chondrocytes obtained from control subjects or purchased (PromoCell) are tested in parallel as negative controls. Positive controls are generated with the use of anti-E2F1, anti-E2F2 and anti-E2F3 antibodies since E2F1 and E2F3 mRNA were detected in normal and OA articular chondrocytes.

The same approach is used to determine whether additional known partners of PHB-1 and PHB-2 are present in the repressor complex detected in OA patients (the candidate proteins are indicated in Table 1 above). Notably, the presence of pRb or of one of its family members (p107 and p130) are investigated since prohibitin/Brg-1/Brm-mediated transcriptional repression was shown to require pRb. To assess whether PHB-1 co-localises in vivo with Brg-1 and Brm to the E2F-responsive element found in the human pitx1 promoter, chromatin immunoprecipitation (ChIP) assays, using anti-Brg-1 and anti-Brm antibodies are performed. ChIP assays are performed with OA articular chondrocytes derived from at least ten distinct OA patients according to the manufacturer's specifications (ActiveMotif, Carlsbad Calif., USA). Articular chondrocyte cultures are obtained from distinct OA patients in order to investigate whether these factors and repressing mechanism are predominantly found only in a specific subset of OA patients or they are conserved among all primary OA patients (excluding secondary knee joint OA). Presence of the mutation is determined by direct sequencing of the promoter region harbouring the E2F-like site for each OA and control subjects to assess whether the mutation seen in human pitx1 promoter has effects in the recruitment of different nuclear interacting partners. Whether pRb or one of its family members (p107 and p-130) is also recruited in vivo with Brg-1 and Brm is investigated. Control experiments is carried out in parallel with normal human articular chondrocytes using anti-E2F1, anti E2F-2 and anti-E2F3 antibodies as positive controls to demonstrate that this E2F site is also subjected to a positive transcriptional regulation by E2Fs in normal cartilage cells. Negative controls will be provided by anti-PHB-1 and anti-PHB-2 antibodies.

Example 18

Determination of Mechanisms Modulating Prohibitins Interactions with Brg-1/Brm in OA Several reports showed that JNK1 promotes the association of PHB-1 with Brg-1 or Brm on E2F-responsive promoters and represses the transcriptional activity of E2F. The finding that JNK1 phosphorylates PHB-1 (in vitro) and regulates prohibitin/Brg1/Brm associations in vivo now adds a testable potential mechanistic link to this pathway. Furthermore, PHB-1 interacts with MLK2, a binding partner of, activator of, and substrate for JNK1. To determine whether JNK1 could affect the physical association between PHB-1 and Brg-1/Brm, co-IP methods are used with normal and OA articular chondrocyte cultures untreated or treated with 100 µM of SP600125, a specific inhibitor of JNK1 for two hours (Stressgene Bioreagents, Ann Arbor, Mich., USA). The effect of JNK1 on the recruitment of PHB-1, PHB-2, Brg-1 and Brm to the endogenous and mutant E2F site in the human pitx1 promoter is then tested by ChIP assays.

Akt subcellular localisation is compared in normal and OA chondrocytes by IHC methods as well as by Western blot analysis with corresponding cytoplasmic and nuclear extracts. Detection of Akt and phospho-Akt (pAkt) is preformed with specific antibodies (Santa Cruz). In the event that cytoplasmic Akt is predominantly detected in OA cells, Akt phosphorylation is stimulated by adding physiological doses of 17-β-estradiol ($10^{-10}$M, Sigma) since estrogenic stimulation was reported to promote accumulation of activated Akt in the nucleus (61).

Additional PHB-1 and PHB-2 interacting partners such as HDAC1 and HDAC5 are tested while others are determined by DNA-pull down method. The analysis of the proteins complexed is carried-out by peptide sequencing coupled to mass spectrometry as described above. The role of estrogens in Akt activation and nuclear localisation is of interest in OA pathogenesis because postmenopausal women are more affected by OA than males after 65 years.

Example 19

Determination of Post-translational Modifications Masking/interfering with NES of PHB-1

There is evidence that PHB-1 and PHB-2 can undergo post-translational modification such as phosphorylation and ubiquitination, but the role of post-translational modifications in modulating the various functions of the prohibitins has yet to be determined. In-silico analysis revealed that PHB-1 NES can be phosphorylated by tyrosine kinases MTOR, PAK, EGFR and JAK. The effect of individual kinases is tested by adding specific kinase inhibitors to the cells prior to analysing PHB-1 interaction with CRM-1 as described above.

Whether the NES of PHB-1 is a substrate for an unknown kinase or any other enzymatic action reducing its interaction with CRM-1 is also tested. A peptide corresponding to the NES of PHB-1 is synthesized and conjugated to a carrier peptide, Penetratin™ (Q-Biogene), for delivery into the cells (cytoplasm and nucleus). The effect of delivering this peptide on the nuclear export of PHB-1 is assessed by double immunofluorescence experiments. Conformation changes in PHB-1-PHB-2 heterodimers or homodimers are also examined by cross-linkage analyses and Western blot.

Although the present invention has been described hereinabove by way of specific embodiments thereof, it can be modified, without departing from the spirit and nature of the subject invention as defined in the appended claims.

REFERENCES

1. Loughlin, J. Genetic epidemiology of primary osteoarthritis. Curr. Opin. Rheumatol. 13, 111-116 (2001).
2. Spector, T. D. & MacGregor, A. J. Risk factors for osteoarthritis: genetics. Osteoarthritis. Cartilage. 12 Suppl A, S39-S44 (2004).

3. Peach, C. A., Carr, A. J., & Loughlin, J. Recent advances in the genetic investigation of osteoarthritis. Trends Mol. Med. 11, 186-191 (2005).
4. Reginato, A. M. & Olsen, B. R. The role of structural genes in the pathogenesis of osteoarthritic disorders. Arthritis Res. 4, 337-345 (2002).
5. Loughlin, J. Polymorphism in signal transduction is a major route through which osteoarthritis susceptibility is acting. Curr. Opin. Rheumatol. 17, 629-633 (2005).
6. Drouin, J., Lanctot, C., & Tremblay, J. J. La famille Ptx des facteurs de transcription a homeodomaine. Médecine/Sciences 14, 335-339 (1998).
7. Drouin, J., Lamolet, B., Lamonerie, T., Lanctot, C., & Tremblay, J. J. The PTX family of homeodomain transcription factors during pituitary developments. Mol. Cell Endocrinol. 140, 31-36 (1998).
8. Lanctôt, C., Lamolet, B., & Drouin, J. The bicoid-related homeoprotein Ptx1 defines the most anterior domain of the embryo and differentiates posterior from anterior lateral mesoderm. Development 124, 2807-2817 (1997).
9. Lanctôt, C., Moreau, A., Chamberland, M., Tremblay, M. L., & Drouin, J. Hindlimb patterning and mandible development require the Ptx1 gene. Development 126, 1805-1810 (1999).
10. Messeguer, X. et al. PROMO: detection of known transcription regulatory elements using species-tailored searches. Bioinformatics. 18, 333-334 (2002).
11. Farre, D. et al. Identification of patterns in biological sequences at the ALGGEN server: PROMO and MAL-GEN. Nucleic Acids Res. 31, 3651-3653 (2003).
12. Tommasi, S. & Pfeifer, G. P. Constitutive protection of E2F recognition sequences in the human thymidine kinase promoter during cell cycle progression. J. Biol. Chem. 272, 30483-30490 (1997).
13. Muller, H. et al. E2Fs regulate the expression of genes involved in differentiation, development, proliferation, and apoptosis. Genes Dev. 15, 267-285 (2001).
14. Zheng, N., Fraenkel, E., Pabo, C. O., & Pavletich, N. P. Structural basis of DNA recognition by the heterodimeric cell cycle transcription factor E2F-DP. Genes Dev. 13, 666-674 (1999).
15. Takahashi, Y., Rayman, J. B., & Dynlacht, B. D. Analysis of promoter binding by the E2F and pRB families in vivo: distinct E2F proteins mediate activation and repression. Genes Dev. 14, 804-816 (2000).
16. Bremner, R. et al. Direct transcriptional repression by pRB and its reversal by specific cyclins. Mol. Cell Biol. 15, 3256-3265 (1995).
17. Hamel, P. A., Gill, R. M., Phillips, R. A., & Gallie, B. L. Transcriptional repression of the E2-containing promoters EIIaE, c-myc, and RB1 by the product of the RB1 gene. Mol. Cell Biol. 12, 3431-3438 (1992).
18. Lam, E. W. & Watson, R. J. An E2F-binding site mediates cell-cycle regulated repression of mouse B-myb transcription. EMBO J 12, 2705-2713 (1993).
19. McClung, J. K., Jupe, E. R., Liu, X. T., & Dell'Orco, R. T. Prohibitin: potential role in senescence, development, and tumor suppression. Exp. Gerontol. 30, 99-124 (1995).
20. Dell'Orco, R. T., McClung, J. K., Jupe, E. R., & Liu, X. T. Prohibitin and the senescent phenotype. Exp. Gerontol. 31, 245-252 (1996).
21. Rastogi, S. et al. Prohibitin facilitates cellular senescence by recruiting specific corepressors to inhibit E2F target genes. Mol. Cell Biol. 26, 4161-4171 (2006).
22. Campisi, J. Cellular senescence as a tumor-suppressor mechanism. Trends Cell Biol. 11, S27-S31 (2001).
23. Martin, J. A. & Buckwalter, J. A. The role of chondrocyte senescence in the pathogenesis of osteoarthritis and in limiting cartilage repair. J Bone Joint Surg Am 85-A Suppl 2, 106-110 (2003).
24. Wang, S., Fusaro, G., Padmanabhan, J., & Chellappan, S. P. Prohibitin co-localizes with Rb in the nucleus and recruits N-CoR and HDAC1 for transcriptional repression. Oncogene 21, 8388-8396 (2002).
25. Altman, R. et al. Development of criteria for the classification and reporting of osteoarthritis. Classification of osteoarthritis of the knee. Diagnostic and Therapeutic Criteria Committee of the American Rheumatism Association. Arthritis Rheum. 29, 1039-1049 (1986).
26. Roy-Beaudry, M. et al. Endothelin 1 promotes osteoarthritic cartilage degradation via matrix metalloprotease 1 and matrix metalloprotease 13 induction. Arthritis Rheum. 48, 2855-2864 (2003).
27. Mankin, H. J., Dorfman, H., Lippiello, L., & Zarins, A. Biochemical and metabolic abnormalities in articular cartilage from osteo-arthritic human hips. II. Correlation of morphology with biochemical and metabolic data. J. Bone Joint Surg. Am. 53, 523-537 (1971).
28. Moreau, A., Yotov, W. V., Glorieux, F. H., & St Arnaud, R. Bone-specific expression of the alpha chain of the nascent polypeptide-associated complex, a coactivator potentiating c-Jun-mediated transcription. Mol. Cell Biol. 18, 1312-1321 (1998).
29. Deeks, J. J. & Altman, D. G. Sensitivity and specificity and their confidence intervals cannot exceed 100%. BMJ 318, 193-194 (1999).
30. Mishra S., Murphy L. C., The Prohibitins: emerging roles in diverse functions. J Cell Mol Med. 10(2): 353-63 (2006).
31. Nijtmans L G, Artal S M, Grivell L A, Coates P J. The mitochondrial PHB complex: roles in mitochondrial respiratory complex assembly, ageing and degenerative disease. Cell Mol Life Sci 2002; 59(1):143-155.
32. Mishra S, Murphy L C, Nyomba B L, Murphy L J. Prohibitin: a potential target for new therapeutics. Trends Mol Med 2005; 11(4):192-197.
33. Lawrence R C, Hochberg M C, Kelsey J L, McDuffie F C, Medsger T A Jr, Felts W R, et al. Estimates of the prevalence of selected arthritic and musculoskeletal diseases in the United States. J Rheumatol 1989; 16:427-41.
34. Felson D T, Zhang Y. An update on the epidemiology of knee and hip osteoarthritis with a view to prevention. Arthritis Rheum 1998; 41:1343-55.
35. Xavier Messeguer, Ruth Escudero, Domenec Farre, Oscar Nunez, Javier Martinez, M. Mar Albà. PROMO: detection of known transcription regulatory elements using species-tailored searches. Bioinformatics, 18, 2, 333-334, 2002;
36. Domènec Farré, Roma Roset, Mario Huerta, José E. Adsuara, Llorenc Rosellé), M. Mar Albà, Xavier Messeguer. Identification of patterns in biological sequences at the ALGGEN server: PROMO and MAL-GEN. Nucleic Acids Res, 31, 13, 3651-3653, 2003.
37. Gamble S C, Odontiadis M, Waxman J et al. Androgens target prohibitin to regulate proliferation of prostate cancer cells. Oncogene 2004; 23(17):2996-3004.
38. Sun L, Liu L, Yang X J, Wu Z. Akt binds prohibitin 2 and relieves its repression of MyoD and muscle differentiation. J Cell Sci 2004; 117(Pt 14):3021-3029.
39. Wang S, Zhang B, Faller D V. Prohibitin requires Brg-1 and Brm for the repression of E2F and cell growth. EMBO J 2002; 21(12):3019-3028.

40. Montano M M, Ekena K, age-Mourroux R, Chang W, Martini P, Katzenellenbogen B S. An estrogen receptor-selective coregulator that potentiates the effectiveness of antiestrogens and represses the activity of estrogens. Proc Natl Acad Sci USA 1999; 96(12):6947-6952.
41. Kurtev V, Margueron R, Kroboth K, Ogris E, Cavailles V, Seiser C. Transcriptional regulation by the repressor of estrogen receptor activity via recruitment of histone deacetylases. J Biol Chem 2004; 279(23):24834-24843.
42. Rastogi S, Joshi B, Fusaro G, Chellappan S. Camptothecin induces nuclear export of prohibitin preferentially in transformed cells through a CRM-1-dependent mechanism. J Biol Chem 2006; 281(5):2951-2959.
43. Wang S, Nath N, Fusaro G, Chellappan S. Rb and prohibitin target distinct regions of E2F1 for repression and respond to different upstream signals. Mol Cell Biol 1999; 19(11):7447-7460.
44. Wang S, Zhang B, Faller D V. BRG1/BRM and prohibitin are required for growth suppression by estrogen antagonists. EMBO J 2004; 23(11):2293-2303.
45. Wang S, Fusaro G, Padmanabhan J, Chellappan S P. Prohibitin co-localizes with Rb in the nucleus and recruits N-CoR and HDAC1 for transcriptional repression. Oncogene 2002; 21(55):8388-8396.
46. Bacher S, Achatz G, Schmitz M L, Lamers M C. Prohibitin and prohibitone are contained in high-molecular weight complexes and interact with alpha-actinin and annexin A2. Biochimie 2002; 84:1205-1218.
47. Rastogi S, Joshi B, Dasgupta P, Morris M, Wright K, Chellappan S. Prohibitin facilitates cellular senescence by recruiting specific corepressors to inhibit E2F target genes. Mol Cell Biol 2006; 26(11):4161-4171.
48. Rasmussen R K, Ji H, Eddes J S et al. Two-dimensional electrophoretic analysis of mixed lineage kinase 2 N-terminal domain binding proteins. Electrophoresis 1998; 19(5):809-817.
49. Fusaro G, Dasgupta P, Rastogi S, Joshi B, Chellappan S. Prohibitin induces the transcriptional activity of p53 and is exported from the nucleus upon apoptotic signaling. J Biol Chem 2003; 278(48):47853-47861.
50. Rajalingam K, Wunder C, Brinkmann V et al. Prohibitin is required for Ras-induced Raf-MEK-ERK activation and epithelial cell migration. Nat Cell Biol 2005; 7(8): 837-843.
51. Wang S, Nath N, Adlam M, Chellappan S. Prohibitin, a potential tumor suppressor, interacts with RB and regulates E2F function. Oncogene 1999; 18(23):3501-3510.
52. Lyons P., 2003. Advances in spotted microarray ressources for expression profiling. Briefings in Functionnal Genomics and Proteomics 2, 21-30.
53. Ding G. and Cantor C. R., 2004. Quantitative analysis of nucleic acids—the last few years of progress. J Biochem Biol 37, 1-10.
54. Scheel J., Von Brevern M. C., Horlein A., Fisher A., Schneider A., Bach A. 2002. Yellow pages to the transcriptome. Pharmacogenomics 3, 791-807.
55. Lopez M. F., Pluskal M. G., 2003. Protein micro- and macroarrays: digitizing the proteome. J Chromatography B 787, 19-27.
56. Wood, W. I. et al. 1985. Base composition-independent hybridization in tetramethylammonium chloride: A method for oligonucleotide screening of highly complex gene library. *Proc. Natl. Acad. Sci. USA* 82. 1585-1588.
57. Kolonin et al. 2006, *Nature Medicine* Advance online publication of June issue.
58. U.S. Pat. No. 5,401,635.
59. Abecasis G R, Cookson W O., 2000. GOLD-graphical overview of linkage disequilibrium. *Bioinformatics* 16:182-3.
60. Ott, J. 2002. Predicting the range of linkage disequilibrium. *Proc. Natl Acad. Sci*. USA, 97, 2-3.
61. Camper-Kirby D, Welch S, Walker A et al. Myocardial Akt activation and gender: increased nuclear activity in females versus males. Circ Res 2001; 88(10):1020-1027.
62. Miller, 1988. *Ann. Reports Med. Chem.* 23:295.
63. Moran et al., 1987. *Nucleic Acids Res.,* 14:5019.
64. Sambrook, J., Fritsch, E. F. & Maniatis, T. (1989). *Molecular Cloning*: A Laboratory Manual, Cold Spring Harbor Laboratory Press, Cold Spring Harbor, N.Y.
65. Lanctot et al., 1999. *Development* 126, 1805-1810.

The invention claimed is:

1. A composition for determining the risk of developing osteoarthritis (OA), said composition comprising:
   (a) a cell sample from a subject suffering from knee or hip OA or at risk of developing early onset knee or hip OA, wherein said cell sample comprises primary cells and wherein said cell sample is an articular chondrocyte sample, a growth plate chondrocyte sample, an osteoblast sample, a skeletal myoblast sample, a synoviocyte sample or a blood cell sample; and
   (b) a non-naturally occurring antibody which specifically binds to PHB1 for detecting nuclear accumulation of PHB1.

2. The composition of claim 1, wherein said molecule comprises a detectable label.

3. The composition of claim 1, wherein the composition comprises a primary antibody which specifically binds to PHB1 and a detectably-labeled secondary antibody which binds to said primary antibody.

4. The composition of claim 3, wherein said detectably-labeled secondary antibody comprises a fluorescent label.

5. The composition of claim 1, wherein said cell sample is nuclear fraction or nuclear extract.

6. The composition of claim 5, further comprising (c) an antibody which specifically binds to lamin.

7. The composition of claim 1, wherein said subject is human.

8. The composition of claim 1, wherein said subject has primary OA.

9. The composition of claim 1, wherein said subject has early onset OA.

10. The composition of claim 1, wherein said subject is 40 years old or younger.

11. The composition of claim 1, further comprising (c) an antibody which specifically binds to PAN SUMO, BCoR and/or PHB2.

12. A composition for determining the risk of developing osteoarthritis (OA), said composition comprising:
   (c) a cell sample from a subject suffering from OA or at risk of developing early onset OA, wherein said cell sample comprises primary cells and wherein said cell sample is an articular chondrocyte sample, a growth plate chondrocyte sample, an osteoblast sample, a skeletal myoblast sample, a synoviocyte sample or a blood cell sample; and (d) a non-naturally occurring antibody which specifically binds to PHB1 for detecting nuclear accumulation of PHB1.

13. The composition of claim 12, wherein said osteoarthritis is knee or hip osteoarthritis.

* * * * *